US009329190B2

(12) United States Patent
Thadhani et al.

(10) Patent No.: US 9,329,190 B2
(45) Date of Patent: May 3, 2016

(54) ASSAYS AND METHODS OF TREATMENT RELATING TO VITAMIN D INSUFFICIENCY

(75) Inventors: Ravi Thadhani, Boston, MA (US); S. Ananth Karumanchi, Chestnut Hill, MA (US); Anders Hayden Berg, Dedham, MA (US); Ishir Bhan, West Newton, MA (US)

(73) Assignees: The General Hospital Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/978,193

(22) PCT Filed: Jan. 6, 2012

(86) PCT No.: PCT/US2012/020407
§ 371 (c)(1),
(2), (4) Date: Nov. 27, 2013

(87) PCT Pub. No.: WO2012/094550
PCT Pub. Date: Jul. 12, 2012

(65) Prior Publication Data
US 2014/0113885 A1 Apr. 24, 2014

Related U.S. Application Data

(60) Provisional application No. 61/430,643, filed on Jan. 7, 2011.

(51) Int. Cl.
*G01N 31/00* (2006.01)
*G01N 33/53* (2006.01)
*G01N 33/82* (2006.01)

(52) U.S. Cl.
CPC ...................................... *G01N 33/82* (2013.01)

(58) Field of Classification Search
CPC ........... C12Q 1/6883; C12Q 2600/158; G01N 33/6893; A61K 2300/00
See application file for complete search history.

(56) References Cited

U.S. PATENT DOCUMENTS

| | | | |
|---|---|---|---|
| 5,532,229 | A | 7/1996 | Vieth |
| 5,972,917 | A | 10/1999 | Bishop et al. |
| 7,700,365 | B2 | 4/2010 | Singh et al. |
| 2004/0132104 | A1 | 7/2004 | Sackrison et al. |
| 2010/0068725 | A1 | 3/2010 | Armbruster et al. |
| 2010/0105879 | A1 | 4/2010 | Katayose et al. |
| 2010/0285603 | A1 | 11/2010 | Kobold et al. |
| 2013/0324505 | A1 | 12/2013 | Thadhani et al. |

FOREIGN PATENT DOCUMENTS

| | | |
|---|---|---|
| EP | 2372365 | 10/2011 |
| JP | 2002-014095 | 1/2002 |
| JP | 2004-515763 | 5/2004 |
| JP | 2009-510415 | 3/2009 |
| JP | 2010-518369 | 5/2010 |
| WO | 89/01631 | 2/1989 |
| WO | WO 89/01631 | 2/1989 |
| WO | 02/057797 | 7/2002 |
| WO | 2007/001969 | 1/2007 |
| WO | 2007/039194 | 4/2007 |
| WO | 2008/092917 | 8/2008 |
| WO | 2010/100487 | 3/2010 |
| WO | WO 2010/100487 | 9/2010 |
| WO | WO 2011/122948 | 10/2011 |
| WO | 2011/144661 | 11/2011 |
| WO | 2012/094550 | 7/2012 |
| WO | 2013/102149 | 7/2013 |
| WO | 2014/179737 | 11/2014 |

OTHER PUBLICATIONS

International Search Report and Written Opinion in International Application No. PCT/US2012/020407, mailed Aug. 31, 2012, 9 pages.
Al-Aly et al., "Changes in serum 25-hydroxyvitamin D and plasma intact PTH levels following treatment with ergocalciferol in patients with CKD," Am J Kidney Dis., Jul. 1, 2007, 50(1):59-68.
Al-oanzi et al., "Vitamin D-binding protein gene microsatellite polymorphism influences BMD and risk of fractures in men," Osteoporos Int., 2008;19:951-60.
Al-oanzi et al., "Assessment of vitamin D status in male osteoporosis," Clin Chem., 2006, 52:248-54.
Aloia et al., "African Americans, 25-hydroxyvitamin D, and osteoporosis: a paradox," Am J Clin Nutr., 2008, 88:545S-50S.
Aloia et al., "The 25(OH)D/PTH threshold in black women," J Clin Endocrinol Metab., 2010, 95:5069-73 (Abstract Only).
Aloia et al., "A randomized controlled trial of vitamin D3 supplementation in African American women," Arch Intern Med., 2005, 165(14):1618-23.
Amsellem et al., "Cubilin is essential for albumin reabsorption in the renal proximal tubule," J Am Soc Nephrol., 2010, 21:1859-67.
Anderson et al., "Vitamin D-Related Genetic Variants, Interactions with Vitamin D Exposure and Breast Cancer Risk among Caucasian Women in Ontario," Cancer Epidemiol Biomarkers Prev., 2011, 20:1708-1717.
Anonymous "Correcting the calcium," Br Med J., Mar. 5, 1977, 1(6061):598.
Arnaud and Constans, "Affinity differences for vitamin D metabolites associated with the genetic isoforms of the human serum carrier protein (DBP)," Hum Genet., 1993, 92:183-8.
Autier and Gandini, "Vitamin D supplementation and total mortality: a meta-analysis of randomized controlled trials," Arch Intern Med., 2007, 167:1730-7.

(Continued)

*Primary Examiner* — Lisa Cook
(74) *Attorney, Agent, or Firm* — Fish & Richardson P.C.

(57) ABSTRACT

Described herein are assays directed to determining the level of bioavailable or free vitamin D in a blood sample in a subject. The values determined for bioavailable or free vitamin D indicate whether the subject suffers from insufficient levels of vitamin D. Also described herein are methods of treatment for vitamin D insufficiency.

8 Claims, 8 Drawing Sheets

(56) References Cited

OTHER PUBLICATIONS

Barrett et al., "Fracture risk in the U.S. Medicare population," J Clin Epidemiol., 1999, 52:243-9.
Bell et al., "Evidence for alteration of the vitamin D-endocrine system in blacks," J Clin Invest 1985;76:470-3.
Bhan et al., "Circulating levels of 25-hydroxyvitamin D and human cathelicidin in healthy adults," J Allergy Clin Immunol, May 2011, 127(5):1302-4.e1 (Author Manuscript).
Bhan et al., "Clinical measures identify vitamin D deficiency in dialysis," Clin J Am Soc Nephrol., Mar. 2010, 5(3):460-467.
Bhan et al., "Dietary vitamin D intake in advanced CKD/ESRD," Semin Dial., Jun. 2010, 23(4):407-410.
Bikle and Gee, "Free, and not total, 1,25-dihydroxyvitamin D regulates 25-hydroxyvitamin D metabolism by keratinocytes," Endocrinol., 1989, 124(2):649-54.
Bikle et al., "Assessment of the free fraction of 25-hydroxyvitamin D in serum and its regulation by albumin and the vitamin D-binding protein," J Clin Endocrinol Metab., 1986, 63(4):954-9.
Bikle et al., "Serum Protein Binding of 1,25-Dihydroxyvitamin D: A Reevaluation by Direct Measurement of Free Metabolite Levels," J Clin Endocrinol Metab., Nov. 1, 1985, 61(5):969-975.
Bischoff-Ferrari et al., "Estimation of optimal serum concentrations of 25-hydroxyvitamin D for multiple health outcomes," Am J Clin Nutr., 2006, 84:18-28.
Bischoff-Ferrari et al., "Fracture prevention with vitamin D supplementation: a meta-analysis of randomized controlled trials," JAMA, 2005, 293(18):2257-64.
Bischoff-Ferrari et al., "Positive association between 25-hydroxy vitamin D levels and bone mineral density: a population-based study of younger and older adults," Am J Med., 2004, 116(9):634-9.
Bischoff-Ferrari et al., "Positive association between serum 25-hydroxyvitamin D level and bone density in osteoarthritis," Arthritis Rheum., 2005, 53(6):821-6.
Bischoff-Ferrari et al., "Prevention of nonvertebral fractures with oral vitamin D and dose dependency: a meta-analysis of randomized controlled trials," Arch Intern Med., 2009, 169:551-61.
Bouillon et al., "Two direct (nonchromatographic) assays for 25-hydroxyvitamin D," Clin Chem., Nov. 1984, 30(11):1731-6.
Braun et al., "Molecular analysis of the gene for the human vitamin-D-binding protein (group-specific component): allelic differences of the common genetic GC types," Hum Genet 1992, 89:401-6.
Braunstein, In: Basic & Clinical Endocrinology. 5th ed. Stamford, Conn: Appleton & Lange; 1997, pp. 422-452.
Brent, "The molecular basis of thyroid hormone action," N Engl J Med., 1994, 331(13):847-53.
Breslau, "Southwestern Internal Medicine Conference: Normal and abnormal regulation of 1,25-(OH)2D synthesis," Am J Med Sci., 1988, 296:417-25.
Carpenter et al., "Vitamin D Binding Protein is a Key Determinnat of 25-Hydroxyvitatmin D Levels in Infants and Toddlers," J Bone Miner Res., 2012, 28(1):213-221.
Cauley et al., "Bone mineral density and the risk of incident nonspinal fractures in black and white women," JAMA, 2005, 293:2102-8.
Cauley et al., "Serum 25 hydroxyvitamin (OH)D and clinical fracture risk in a multiethnic Cohort of women: The Women's health initiative (WHI)," J Bone Miner Res., 2011, 26(10):2378-88.
Cauley et al., "Serum 25- hydroxyvitamin D concentrations and risk for hip fractures," Ann Intern Med., 2008, 149(4):242-50 (Author Manuscript).
Chapuy et al., "Vitamin D3 and calcium to prevent hip fractures in the elderly women," N Engl J Med., 1992, 327(23):1637-42.
Chonchol and Scragg, "25-Hydroxyvitamin D, insulin resistance, and kidney function in the Third National Health and Nutrition Examination Survey," Kidney Int., Jan. 1, 2007, 71(2):134-139.
Chun et al., "Vitamin D-binding protein directs monocyte responses to 25-hydroxy- and 1,25-dihydroxyvitamin D," J Clin Endocrinol Metab., 2010, 95(7):3368-76.
Clemens et al., "Increased skin pigment reduces the capacity of skin to synthesise vitamin D3," Lancet, 1982;1:74-6.
Compher et al., "Vitamin D and the bariatric surgical patient: a review," Obes Surg., 2008, 18:220-4.
Constans et al., "Population distribution of the human vitamin D binding protein: anthropological considerations," Am J Phys Anthropol., 1985, 68:107-22.
Dawson-Hughes et al., "Effect of calcium and vitamin D supplementation on bone density in men and women 65 years of age or older," N Engl J Med., 1997, 337(10):670-6.
Dawson-Hughes et al., "Rates of bone loss in postmenopausal women randomly assigned to one of two dosages of vitamin D," Am J Clin Nutr., 1995, 61:1140-5.
Diaz et al., "The association of vitamin D deficiency and insufficiency with diabetic nephropathy: implications for health disparities," J Am Board Fam Med., 2009, 22:521-7.
Drechsler et al., "Vitamin D deficiency is associated with sudden cardiac death, combined cardiovascular events, and mortality in haemodialysis patients," Eur Heart J., Sep. 2010, 31(18):2253-2261.
Drechsler et al., "Vitamin D status and clinical outcomes in incident dialysis patients: results from the NECOSAD study," Nephrol Dial Transplant., Mar. 2011, 26(3):1024-1032.
Efron et al., "Least angle regression," Ann Stat., 2004, 32:407-99.
Ekins et al., "Principles of free hormone measurement," J Endocrinol Invest., 1986, 9 Suppl 4:3-15.
Emadi-Konjin et al., "Evaluation of an algorithm for calculation of serum "bioavailable" testosterone (BAT)," Clin Biochem., 2003, 36:591-6.
Engelman et al., "Genetic and environmental determinants of 25-hydroxyvitamin D and 1,25-dihydroxyvitamin D levels in Hispanic and African Americans," J Clin Endocrinol Metab., 2008, 93(9):3381-8.
Fang et al., "Vitamin D binding protein genotype and osteoporosis," Calcif Tissue Int., 2009, 85:85-93.
Fiscella and Franks, "Vitamin D, race, and cardiovascular mortality: findings from a national US sample," Ann Fam Med., 2010, 8:11-8.
Forman et al., "Plasma 25-hydroxyvitamin D levels and risk of incident hypertension," Hypertension, May 2007,49(5):1063-1069.
Gerdhem et al., "Association between 25-hydroxy vitamin D levels, physical activity, muscle strength and fractures in the prospective population-based OPRA Study of Elderly Women," Osteoporos Int., 2005, 16(11):1425-31.
Ginde et al., "Association between serum 25-hydroxyvitamin D level and upper respiratory tract infection in the Third National Health and Nutrition Examination Survey." Arch Intern Med., 2009, 169(4):384-90.
Gloth, III et al., "Vitamin D deficiency in homebound elderly persons," Jama, 1995, 274:1683-6.
Gombart et al., "Low plasma level of cathelicidin antimicrobial peptide (hCAP18) predicts increased infectious disease mortality in patients undergoing hemodialysis," Clin.Infect. Dis., Feb. 15, 2009, 48(4):418-424.
González et al., "Vitamin D insufficiency and deficiency in chronic kidney disease. A single center observational study," Am J Nephrol., Aug. 2004, 24(5):503-510.
Grant et al., "Oral vitamin D3 and calcium for secondary prevention of low-trauma fractures in elderly people (Randomised Evaluation of Calcium Or vitamin D, RECORD): a randomised placebo-controlled trial," Lancet, 2005, 365(9471):1621-8.
Gutiérrez et al., "Racial differences in the relationship between vitamin D, bone mineral density, and parathyroid hormone in the National Health and Nutrition Examination Survey," Osteoporosis Int., Jun. 2011, 22(6):1745-1753 (Author Manuscript).
Hamilton et al., "Profound Vitamin D Deficiency in a Diverse Group of Women during Pregnancy Living in a Sun-Rich Environment at Latitude 32 degrees N," Int J Endocrinol., 2010, 2010:917428.
Hannan et al., "Serum 25-hydroxyvitamin D and bone mineral density in a racially and ethnically diverse group of men," J Clin Endocrinol Metab., 2008, 93(1):40-6.
Harris and Dawson-Hughes, "Reduced sun exposure does not explain the inverse association of 25-hydroxyvitamin D with percent body fat in older adults," J Clin Endocrinol Metab., 2007, 92:3155-7.
Harris and Dawson-Hughes, "Seasonal changes in plasma 25-hydroxyvitamin D concentrations of young American black and white women," Am J Clin Nutr., 1998, 67:1232-6.

(56) References Cited

OTHER PUBLICATIONS

Harris, "Vitamin D and African Americans," J Nutr., 2006, 136:1126-9.
Holick, "MrOs is D-ficient," J Clin Endocrinol Metab., 2009, 94:1092-3.
Holick, "Sunlight and vitamin D for bone health and prevention of autoimmune diseases, cancers, and cardiovascular disease," Am J Clin Nutr., 2004, 80:1678S-88S.
Holick, "Vitamin D deficiency," N Engl J Med., Jul. 19, 2007, 357(3):266-281.
Hooten et al., "microRNA expression patterns reveal differential expression of target genes with age," PLoS One, 2010, 5:e10724.
Hunter et al., "Genetic contribution to bone metabolism, calcium excretion, and vitamin D and parathyroid hormone regulation," J Bone Miner Res., 2001, 16:371-8.
Institute of Medicine. Dietary Reference Intakes for Calcium and Vitamin D. In: http://www.iom.edu/~/media/Files/Report%20Files/2010/Dietary-Reference-Intakes-for-Calcium-and-Vitamin-D/Vitamin%20D%20and%20Calcium%202010%20Report%20Brief.pdf, ed.; Nov. 2010:1-4.
Jackson et al., "Calcium plus vitamin D supplementation and the risk of fractures," N Engl J Med., 2006, 354(7):669-83.
Jean et al., "Vitamin D Deficiency and Associated Factors in Hemodialysis Patients," J Ren Nutr., Sep. 2008, 18(5):395-399.
Judd and Tangpricha, "Vitamin D deficiency and risk for cardiovascular disease," Am J Med Sci., 2009, 338:40-4.
Karagas et al., "Heterogeneity of hip fracture: age, race, sex, and geographic patterns of femoral neck and trochanteric fractures among the US elderly," Am J Epidemiol., 1996, 143:677-82.
Kremer et al., "Vitamin D status and its relationship to body fat, final height, and peak bone mass in young women," J Clin Endocrinol Metab., 2009, 94(1):67-73.
Lauridsen et al., "Mean serum concentration of vitamin D-binding protein (Gc globulin) is related to the Gc phenotype in women," Clin Chem., 2001, 47:753-6.
Lauridsen et al., "Plasma concentrations of 25-hydroxy-vitamin D and 1,25-dihydroxy-vitamin D are related to the phenotype of Gc (vitamin D-binding protein): a cross-sectional study on 595 early postmenopausal women," Calcif Tissue Int., 2005, 77(1):15-22.
Leheste et al., "Hypocalcemia and osteopathy in mice with kidney-specific megalin gene defect," FASEB J., 2003, 17:247-9.
London et al., "Arterial calcifications and bone histomorphometry in end-stage renal disease," J Am Soc Nephrol, Jul. 1, 2004, 15(7):1943-1951.
London et al., "Mineral metabolism and arterial functions in end-stage renal disease: potential role of 25-hydroxyvitamin D deficiency," J Am Soc Nephrol., Feb. 1, 2007, 18(2):613-620.
Martins et al., "Prevalence of cardiovascular risk factors and the serum levels of 25-hydroxyvitamin D in the United States: data from the Third National Health and Nutrition Examination Survey," Arch Intern Med., 2007, 167:1159-65.
Mathias and Jung, "Determination of drug-serum protein interactions via fluorescence polarization measurements," Anal Bioanal Chem., Jul. 2007, 388(5-6):1147-56.
Matsuoka et al., "Compensation for the interracial variance in the cutaneous synthesis of vitamin D," J Lab Clin Med., 1995, 126:452-7.
Matsuoka et al., "Sunscreens suppress cutaneous vitamin D3 synthesis," J Clin Endocrinol Metab., 1987, 64:1165-8.
Mendel, "Preliminary evaluation of a fluorescence polarization immunoassay (Abbott TDx) for estimating serum free thyroxine concentrations in patients with critical nonthyroid illness and low total thyroxine concentrations in serum," Clin Chem., 1992, 38(9):1916-7.
Mendel, "The free hormone hypothesis: a physiologically based mathematical model," Endocr Rev., 1989, 10(3):232-74.
Merewood et al., "Widespread vitamin D deficiency in urban Massachusetts newborns and their mothers," Pediatrics, 2010, 125:640-7.
Morris and Anderson, "Autocrine and paracrine actions of vitamin D," Clin Biochem Rev., 2010, 31:129-38.

Need et al., "Vitamin D status: effects on parathyroid hormone and 1,25-dihydroxyvitamin D in postmenopausal women," Am J Clin Nutr., 2000, 71:1577-81.
Nesby-O'Dell et al., "Hypovitaminosis D prevalence and determinants among African American and white women of reproductive age: third National Health and Nutrition Examination Survey, 1988-1994," Am J Clin Nutr., 2002, 76:187-92.
Nigwekar et al., "Nutritional vitamin D in dialysis patients: what to D-iscern? Nephrology Dialysis Transplantation," Mar. 2011, 26(3):764-766.
Nykjaer et al., "An endocytic pathway essential for renal uptake and activation of the steroid 25-(OH) vitamin $D_3$," Cell, 1999, 96:507-15.
Nykjaer et al., "Cubilin dysfunction causes abnormal metabolism of the steroid hormone 25(OH) vitamin D(3)," Proc Natl Acad Sci U S A, 2001, 98:13895-900.
Ooms et al., "Prevention of bone loss by vitamin D supplementation in elderly women: a randomized double-blind trial," J Clin Endocrinol Metab., 1995, 80(4):1052-8.
O'Riordan, "Rickets in the 17th Century," J Bone and Mineral Res., 2006, 21:1506-10.
Orwoll et al., "Vitamin D deficiency in older men," J Clin Endocrinol Metab., 2009, 94:1214-22.
Ott, "Review article: Bone density in patients with chronic kidney disease stages 4-5," Nephrol., Jun. 2009, 14(4):395-403.
Papiha et al., "Vitamin D binding protein gene in male osteoporosis: association of plasma DBP and bone mineral density with (TAAA)(n)-Alu polymorphism in DBP," Calcif Tissue Int., 1999, 65:262-6.
Parfitt, Osteomalacia and related disorders. In: Avioli LV, Krane, S.M., ed. Metabolic bone disease. 3rd ed. San Diego, CA: Academic Press; 1998:327-86.
Porthouse et al., "Randomised controlled trial of calcium and supplementation with cholecalciferol (vitamin D3) for prevention of fractures in primary care," BMJ, 2005, 330(7498):1003.
Powe et al., "First trimester vitamin D, vitamin D binding protein, and subsequent preeclampsia," Hypertension, Oct. 2010, 56(4):758-763.
Powe et al., "Vitamin D Binding Protein Modifies Relationship between Vitamin D and Calcium in Dialysis," In: American Society of Nephrology Annual Meeting; Denver, CO.; Nov 2010, Abstract TH-PO191, p. 155A.
Powe et al., "Vitamin D-binding protein modifies the vitamin D-bone mineral density relationship," J Bone Miner Res., Jul. 2011, 26(7):1609-1616.
Ravani et al., "Vitamin D levels and patient outcome in chronic kidney disease," Kidney Int., Jan. 1, 2009, 75(1):88-95.
Reis et al., "Differences in vitamin D status as a possible contributor to the racial disparity in peripheral arterial disease," Am J Clin Nutr., 2008, 88:1469-77.
Russo et al., "Progression of coronary artery calcification in predialysis patients," Am J Nephrol., 2007, 27:152-8 (Abstract Only).
Russo et al., "The normal kidney filters nephrotic levels of albumin retrieved by proximal tubule cells: retrieval is disrupted in nephrotic states," Kidney Int., 2007, 71:504-13.
Safadi et al., "Osteopathy and resistance to vitamin D toxicity in mice null for vitamin D binding protein," J Clin Invest., 1999, 103(2):239-51.
Sahota, "Osteoporosis and the role of vitamin D and calcium-vitamin D deficiency, vitamin D insufficiency and vitamin D sufficiency," Age Ageing, 2000, 29:301-4.
Sanders et al., "Annual high-dose oral vitamin D and falls and fractures in older women: a randomized controlled trial," JAMA, 2010, 303(18):1815-22.
Schneider et al., "Effects of vitamin D binding proteinmacrophage activating factor (DBP-MAF) infusion on bone resorption in two osteopetrotic mutations," Bone, 1995, 16(6):657-62.
Schottker et al., "Standardization of misleading immunoassay based 25-hydroxyvitamin D levels with liquid chromatography tandem-mass spectrometry in a large cohort study," PLoS One, 2012, 7:e48774.

(56) References Cited

OTHER PUBLICATIONS

Sherman et al., "Biochemical parameters associated with low bone density in healthy men and women," J Bone Miner Res., 1992, 7(10):1123-30.
Shimizu et al., "Synthesis of a reagent for fluorescence-labeling of vitamin D and its use in assaying vitamin D metabolites," Anal Biochem., Apr. 1991, 194(1):77-81.
Sinotte et al., "Genetic polymorphisms of the vitamin D binding protein and plasma concentrations of 25-hydroxyvitamin D in premenopausal women," Am J Clin Nutr., 2009, 89(2):634-40.
Smith et al., "Genome-Wide Association Studies of the PR Interval in African Americans," PLoS Genet., 2011, 7:EPub: e1001304.
Snijder et al., "Adiposity in relation to vitamin D status and parathyroid hormone levels: a population-based study in older men and women," J Clin Endocrinol Metab., 2005, 90(7):4119-23.
Stone et al., "Hormonal predictors of bone loss in elderly women: a prospective study. The Study of Osteoporotic Fractures Research Group," J Bone Miner Res., 1998, 13(7):1167-74.
Tangpricha et al., "Vitamin D insufficiency among free-living healthy young adults," Am J Med., 2002, 112:659-62 (Author Manuscript).
Thacher and Clarke, "Vitamin D insufficiency," Mayo Clin Proc., 2011, 86:50-60.
Thomas et al., "Hypovitaminosis D in medical inpatients," N Engl J Med., 1998, 338:777-83.
Tibrishani, "Regression shrinkage and section via the lasso," J Royal Stat Soc., 1996, 58:267-88.
Valimaki et al., "Vitamin D status as a determinant of peak bone mass in young Finnish men," J Clin Endocrinol Metab., 2004, 89(1):76-80.
van Driel et al., "Evidence for auto/paracrine actions of vitamin D in bone: 1 alphahydroxylase expression and activity in human bone cells," FASEB J., 2006, 20(13):2417-9.
van Hoof et al., "Determination of non-proteinbound plasma 1,25-dihydroxyvitamin D by symmetric (rate) dialysis," Anal Biochem., 1998, 258(2):176-83.
Vermeulen et al., "A critical evaluation of simple methods for the estimation of free testosterone in serum," J Clin Endocrinol Metab., 1999, 84(10):3666-72.
Vieth et al., "The urgent need to recommend an intake of vitamin D that is effective," Am J Clin Nutr., 2007, 85:649-50.
Wactawski-Wende et al., "Calcium plus vitamin D supplementation and the risk of colorectal cancer," N Engl J Med., 2006, 354(7):684-96.
Wang et al., "Common genetic determinants of vitamin D insufficiency: a genome-wide association study," Lancet, 2010, 376:180-8 (Author Manuscript).
Wang et al., "Systematic review: Vitamin D and calcium supplementation in prevention of cardiovascular events," Ann Intern Med., 2010, 152:315-23.
Wang et al., "Vitamin D deficiency and risk of cardiovascular disease," Circulation, 2008, 117(4):503-11.
Wolf et al., "First trimester insulin resistance and subsequent preeclampsia: a prospective study," J Clin Endocrinol Metab., 2002, 87:1563-8.
Wolf et al., "Impact of Activated Vitamin D and Race on Survival among Hemodialysis Patients," J Am Soc Nephrol., Apr. 9, 2008, 19(7):1379-1388.
Wolf et al., "Vitamin D levels and early mortality among incident hemodialysis patients," Kidney Int., Oct. 1, 2007, 72(8):1004-1013.
Wortsman et al., "Decreased bioavailability of vitamin D in obesity," Am J Clin Nutr., 2000, 72:690-3.
Zella et al., "Vitamin D-binding protein influences total circulating levels of 1,25-dihydroxyvitamin D3 but does not directly modulate the bioactive levels of the hormone in vivo," Endocrinolog., 2008, 149:3656-67.
Zisman et al., "Impact of Ergocalciferol Treatment of Vitamin D Deficiency on Serum Parathyroid Hormone Concentrations in Chronic Kidney Disease," Am J Nephrol., 2007, 27(1):36-43.
Zittermann et al., "Low vitamin D status: a contributing factor in the pathogenesis of congestive heart failure?" J Am Coll Cardiol., 2003, 41:105-12.
International Search Report from international application No. PCT/US2012/020407 mailed Aug. 31, 2012, 3 pgs.
Bhan et al., "Bioavailable vitamin D is more tightly linked to mineral metabolism than total vitamin D in incident hemodialysis patients," Kidney International, 82(1):84-89 (2012).
Supplementary European Search Report issued in EP12732092 on Mar. 12, 2015 (9 pages).
U.S. Appl. No. 14/709,315, filed May 11, 2015, Thadhani et al.
U.S. Appl. No. 14/888,765, filed Nov. 3, 2015, Thadhani.
Abbas et al., "The Gc2 Allele Of The Vitamin D Binding Protein Is Associated With A Decreased Postmenopausal Breast Cancer Risk, Independent Of The Vitamin D Status," Cancer Epidemiol Biomarkers Prev. 17(6):1339-1343 (2008).
English Translation of Office Action issued in JP2013-548558 issued on Sep. 29, 2015 (4 pages).
International Search Report and Written Opinion dated May 22, 2105 in international application No. PCT/US2014/036650, 19 pages.
International Preliminary Report on Patentability in International Application No. PCT/US2014/036650, dated Nov. 3, 2015, 13 pages.
International Preliminary Report on Patentability in International Application No. PCT/US2012/020407, dated Jul. 10, 2013, 6 pages.
Non-Final Office Action in U.S. Appl. No. 13/918,563, dated Sep. 30, 2014, 15 pages.

```
                              SEQUENCE LISTING

<160> NUMBER OF SEQ ID NOS: 6

<210> SEQ ID NO 1
<211> LENGTH: 474
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human VDBP Isoform 1, variant 1
      NCBI Ref: NP_000574

<400> SEQUENCE: 1

Met Lys Arg Val Leu Val Leu Leu Leu Ala Val Ala Phe Gly His Ala
 1               5                  10                  15

Leu Glu Arg Gly Arg Asp Tyr Glu Lys Asn Lys Val Cys Lys Glu Phe
                20                  25                  30

Ser His Leu Gly Lys Glu Asp Phe Thr Ser Leu Ser Leu Val Leu Tyr
            35                  40                  45

Ser Arg Lys Phe Pro Ser Gly Thr Phe Glu Gln Val Ser Gln Leu Val
        50                  55                  60

Lys Glu Val Val Ser Leu Thr Glu Ala Cys Cys Ala Glu Gly Ala Asp
65                  70                  75                  80
```

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 2
<211> LENGTH: 474

```
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human VDBP Isoform 1, variant 2
      NCBI Ref: NP_001191235

<400> SEQUENCE: 2
```

| | | | | | | | | | | | | | | |
|---|---|---|---|---|---|---|---|---|---|---|---|---|---|---|
|Met|Lys|Arg|Val|Leu|Val|Leu|Leu|Ala|Val|Ala|Phe|Gly|His|Ala|
|1| | | |5| | | | |10| | | | |15|
|Leu|Glu|Arg|Gly|Arg|Asp|Tyr|Glu|Lys|Asn|Lys|Val|Cys|Lys|Glu|Phe|
| | | |20| | | | |25| | | | |30| |
|Ser|His|Leu|Gly|Lys|Glu|Asp|Phe|Thr|Ser|Leu|Ser|Leu|Val|Leu|Tyr|
| | | |35| | | | |40| | | | |45| |
|Ser|Arg|Lys|Phe|Pro|Ser|Gly|Thr|Phe|Glu|Gln|Val|Ser|Gln|Leu|Val|
| |50| | | | |55| | | | |60| | | |
|Lys|Glu|Val|Val|Ser|Leu|Thr|Glu|Ala|Cys|Cys|Ala|Glu|Gly|Ala|Asp|
|65| | | | |70| | | | |75| | | | |80|
|Pro|Asp|Cys|Tyr|Asp|Thr|Arg|Thr|Ser|Ala|Leu|Ser|Ala|Lys|Ser|Cys|
| | | | |85| | | | |90| | | | |95| |
|Glu|Ser|Asn|Ser|Pro|Phe|Pro|Val|His|Pro|Gly|Thr|Ala|Glu|Cys|Cys|
| | | |100| | | | |105| | | | |110| |
|Thr|Lys|Glu|Gly|Leu|Glu|Arg|Lys|Leu|Cys|Met|Ala|Ala|Leu|Lys|His|
| | |115| | | | |120| | | | |125| | |
|Gln|Pro|Gln|Glu|Phe|Pro|Thr|Tyr|Val|Glu|Pro|Thr|Asn|Asp|Glu|Ile|
|130| | | | |135| | | | |140| | | | |
|Cys|Glu|Ala|Phe|Arg|Lys|Asp|Pro|Lys|Glu|Tyr|Ala|Asn|Gln|Phe|Met|
|145| | | | |150| | | | |155| | | | |160|
|Trp|Glu|Tyr|Ser|Thr|Asn|Tyr|Gly|Gln|Ala|Pro|Leu|Ser|Leu|Leu|Val|
| | | | |165| | | | |170| | | | |175| |
|Ser|Tyr|Thr|Lys|Ser|Tyr|Leu|Ser|Met|Val|Gly|Ser|Cys|Cys|Thr|Ser|
| | | |180| | | | |185| | | | |190| | |
|Ala|Ser|Pro|Thr|Val|Cys|Phe|Leu|Lys|Glu|Arg|Leu|Gln|Leu|Lys|His|
| | |195| | | | |200| | | | |205| | | |
|Leu|Ser|Leu|Leu|Thr|Thr|Leu|Ser|Asn|Arg|Val|Cys|Ser|Gln|Tyr|Ala|
| |210| | | | |215| | | | |220| | | | |
|Ala|Tyr|Gly|Glu|Lys|Lys|Ser|Arg|Leu|Ser|Asn|Leu|Ile|Lys|Leu|Ala|
|225| | | | |230| | | | |235| | | | |240|
|Gln|Lys|Val|Pro|Thr|Ala|Asp|Leu|Glu|Asp|Val|Leu|Pro|Leu|Ala|Glu|
| | | | |245| | | | |250| | | | |255| |
|Asp|Ile|Thr|Asn|Ile|Leu|Ser|Lys|Cys|Cys|Glu|Ser|Ala|Ser|Glu|Asp|
| | | |260| | | | |265| | | | |270| | |
|Cys|Met|Ala|Lys|Glu|Leu|Pro|Glu|His|Thr|Val|Lys|Leu|Cys|Asp|Asn|
| | |275| | | | |280| | | | |285| | | |
|Leu|Ser|Thr|Lys|Asn|Ser|Lys|Phe|Glu|Asp|Cys|Cys|Gln|Glu|Lys|Thr|
| |290| | | | |295| | | | |300| | | | |
|Ala|Met|Asp|Val|Phe|Val|Cys|Thr|Tyr|Phe|Met|Pro|Ala|Ala|Gln|Leu|
|305| | | | |310| | | | |315| | | | |320|
|Pro|Glu|Leu|Pro|Asp|Val|Glu|Leu|Pro|Thr|Asn|Lys|Asp|Val|Cys|Asp|
| | | | |325| | | | |330| | | | |335| |
|Pro|Gly|Asn|Thr|Lys|Val|Met|Asp|Lys|Tyr|Thr|Phe|Glu|Leu|Ser|Arg|
| | | |340| | | | |345| | | | |350| | |
|Arg|Thr|His|Leu|Pro|Glu|Val|Phe|Leu|Ser|Lys|Val|Leu|Glu|Pro|Thr|
| | |355| | | | |360| | | | |365| | | |

```
Leu Lys Ser Leu Gly Glu Cys Cys Asp Val Glu Asp Ser Thr Thr Cys
370                 375                 380

Phe Asn Ala Lys Gly Pro Leu Leu Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
        420                 425                 430

Ala Thr Pro Thr Glu Leu Ala Lys Leu Val Asn Lys His Ser Asp Phe
            435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu
465                 470

<210> SEQ ID NO 3
<211> LENGTH: 493
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human VDBP Isoform 2
      NCBI Ref: NP_001191236

<400> SEQUENCE: 3

Met Leu Trp Ser Trp Ser Glu Glu Arg Gly Gly Ala Ala Arg Leu Ser
1               5                   10                  15

Gly Arg Lys Met Lys Arg Val Leu Val Leu Leu Leu Ala Val Ala Phe
                20                  25                  30

Gly His Ala Leu Glu Arg Gly Arg Asp Tyr Glu Lys Asn Lys Val Cys
            35                  40                  45

Lys Glu Phe Ser His Leu Gly Lys Glu Asp Phe Thr Ser Leu Ser Leu
        50                  55                  60

Val Leu Tyr Ser Arg Lys Phe Pro Ser Gly Thr Phe Glu Gln Val Ser
65                  70                  75                  80

Gln Leu Val Lys Glu Val Val Ser Leu Thr Glu Ala Cys Cys Ala Glu
                85                  90                  95

Gly Ala Asp Pro Asp Cys Tyr Asp Thr Arg Thr Ser Ala Leu Ser Ala
                100                 105                 110

Lys Ser Cys Glu Ser Asn Ser Pro Phe Pro Val His Pro Gly Thr Ala
        115                 120                 125

Glu Cys Cys Thr Lys Glu Gly Leu Glu Arg Lys Leu Cys Met Ala Ala
130                 135                 140

Leu Lys His Gln Pro Gln Glu Phe Pro Thr Tyr Val Glu Pro Thr Asn
145                 150                 155                 160

Asp Glu Ile Cys Glu Ala Phe Arg Lys Asp Pro Lys Glu Tyr Ala Asn
                165                 170                 175

Gln Phe Met Trp Glu Tyr Ser Thr Asn Tyr Gly Gln Ala Pro Leu Ser
            180                 185                 190

Leu Leu Val Ser Tyr Thr Lys Ser Tyr Leu Ser Met Val Gly Ser Cys
        195                 200                 205

Cys Thr Ser Ala Ser Pro Thr Val Cys Phe Leu Lys Glu Arg Leu Gln
210                 215                 220

Leu Lys His Leu Ser Leu Leu Thr Thr Leu Ser Asn Arg Val Cys Ser
225                 230                 235                 240
```

Gln Tyr Ala Ala Tyr Gly Glu Lys Lys Ser Arg Leu Ser Asn Leu Ile
                245                 250                 255

Lys Leu Ala Gln Lys Val Pro Thr Ala Asp Leu Glu Asp Val Leu Pro
            260                 265                 270

Leu Ala Glu Asp Ile Thr Asn Ile Leu Ser Lys Cys Cys Glu Ser Ala
        275                 280                 285

Ser Glu Asp Cys Met Ala Lys Glu Leu Pro Glu His Thr Val Lys Leu
    290                 295                 300

Cys Asp Asn Leu Ser Thr Lys Asn Ser Lys Phe Glu Asp Cys Cys Gln
305                 310                 315                 320

Glu Lys Thr Ala Met Asp Val Phe Val Cys Thr Tyr Phe Met Pro Ala
                325                 330                 335

Ala Gln Leu Pro Glu Leu Pro Asp Val Glu Leu Pro Thr Asn Lys Asp
            340                 345                 350

Val Cys Asp Pro Gly Asn Thr Lys Val Met Asp Lys Tyr Thr Phe Glu
        355                 360                 365

Leu Ser Arg Arg Thr His Leu Pro Glu Val Phe Leu Ser Lys Val Leu
    370                 375                 380

Glu Pro Thr Leu Lys Ser Leu Gly Glu Cys Cys Asp Val Glu Asp Ser
385                 390                 395                 400

Thr Thr Cys Phe Asn Ala Lys Gly Pro Leu Leu Lys Lys Glu Leu Ser
                405                 410                 415

Ser Phe Ile Asp Lys Gly Gln Glu Leu Cys Ala Asp Tyr Ser Glu Asn
            420                 425                 430

Thr Phe Thr Glu Tyr Lys Lys Lys Leu Ala Glu Arg Leu Lys Ala Lys
        435                 440                 445

Leu Pro Asp Ala Thr Pro Thr Glu Leu Ala Lys Leu Val Asn Lys His
    450                 455                 460

Ser Asp Phe Ala Ser Asn Cys Cys Ser Ile Asn Ser Pro Pro Leu Tyr
465                 470                 475                 480

Cys Asp Ser Glu Ile Asp Ala Glu Leu Lys Asn Ile Leu
                485                 490

<210> SEQ ID NO 4
<211> LENGTH: 609
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human preproalbumin
      NCBI Ref: NP_000468

<400> SEQUENCE: 4

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

-continued

```
Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
```

```
                  515                 520                 525
Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu

<210> SEQ ID NO 5
<211> LENGTH: 591
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human proalbumin

<400> SEQUENCE: 5

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
                20                  25                  30

Phe Ala Gln Tyr Leu Gln Gln Cys Pro Phe Glu Asp His Val Lys Leu
            35                  40                  45

Val Asn Glu Val Thr Glu Phe Ala Lys Thr Cys Val Ala Asp Glu Ser
        50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
                85                  90                  95

Cys Ala Lys Gln Glu Pro Glu Arg Asn Glu Cys Phe Leu Gln His Lys
            100                 105                 110

Asp Asp Asn Pro Asn Leu Pro Arg Leu Val Arg Pro Glu Val Asp Val
        115                 120                 125

Met Cys Thr Ala Phe His Asp Asn Glu Glu Thr Phe Leu Lys Lys Tyr
130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
                165                 170                 175

Ala Ala Asp Lys Ala Ala Cys Leu Leu Pro Lys Leu Asp Glu Leu Arg
            180                 185                 190

Asp Glu Gly Lys Ala Ser Ser Ala Lys Gln Arg Leu Lys Cys Ala Ser
        195                 200                 205

Leu Gln Lys Phe Gly Glu Arg Ala Phe Lys Ala Trp Ala Val Ala Arg
    210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
                245                 250                 255
```

```
Leu Glu Cys Ala Asp Asp Arg Ala Asp Leu Ala Lys Tyr Ile Cys Glu
            260                 265                 270

Asn Gln Asp Ser Ile Ser Ser Lys Leu Lys Glu Cys Cys Glu Lys Pro
        275                 280                 285

Leu Leu Glu Lys Ser His Cys Ile Ala Glu Val Glu Asn Asp Glu Met
    290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
                325                 330                 335

Leu Tyr Glu Tyr Ala Arg Arg His Pro Asp Tyr Ser Val Val Leu Leu
            340                 345                 350

Leu Arg Leu Ala Lys Thr Tyr Glu Thr Thr Leu Glu Lys Cys Cys Ala
        355                 360                 365

Ala Ala Asp Pro His Glu Cys Tyr Ala Lys Val Phe Asp Glu Phe Lys
    370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
                405                 410                 415

Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
        435                 440                 445

Ala Lys Arg Met Pro Cys Ala Glu Asp Tyr Leu Ser Val Val Leu Asn
450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
                485                 490                 495

Leu Glu Val Asp Glu Thr Tyr Val Pro Lys Glu Phe Asn Ala Glu Thr
            500                 505                 510

Phe Thr Phe His Ala Asp Ile Cys Thr Leu Ser Glu Lys Glu Arg Gln
        515                 520                 525

Ile Lys Lys Gln Thr Ala Leu Val Glu Leu Val Lys His Lys Pro Lys
    530                 535                 540

Ala Thr Lys Glu Gln Leu Lys Ala Val Met Asp Asp Phe Ala Ala Phe
545                 550                 555                 560

Val Glu Lys Cys Cys Lys Ala Asp Asp Lys Glu Thr Cys Phe Ala Glu
                565                 570                 575

Glu Gly Lys Lys Leu Val Ala Ala Ser Gln Ala Ala Leu Gly Leu
            580                 585                 590

<210> SEQ ID NO 6
<211> LENGTH: 585
<212> TYPE: PRT
<213> ORGANISM: Homo sapien
<220> FEATURE:
<221> NAME/KEY: VARIANT
<222> LOCATION: (0)...(0)
<223> OTHER INFORMATION: Human albumin

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

```
            20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
            50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
            130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
            210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
            290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
```

-continued

```
Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```

ASSAYS AND METHODS OF TREATMENT RELATING TO VITAMIN D INSUFFICIENCY

CROSS REFERENCE

This application is a U.S. National Phase Application under 35 U.S.C. §371 of International Patent Application No. PCT/US2012/020407, filed on Jan. 6, 2012, which claims benefit of U.S. Provisional Patent Application Ser. No. 61/430,643 filed Jan. 7, 2011. The entire contents of the foregoing are hereby incorporated by reference.

GOVERNMENT SUPPORT

This invention was made with federal government support under Grant Number M01-(RR-01066)-Harvard Clinical and Translational Science Center awarded by the National Center for Research Resources and Grant K23 1K23DK081677 awarded by the National Institutes of Health. The U.S. Government has certain rights in the invention.

FIELD OF THE INVENTION

The invention is directed to assays and methods of treatment relating to vitamin D insufficiency.

BACKGROUND OF THE INVENTION

Vitamin D insufficiency (variously defined as <20 to 30 ng/mL of total serum 25(OH)D as currently measured) is highly prevalent, even in otherwise healthy individuals. Reported in >1 billion people worldwide, it is now recognized as one of the most common subclinical medical conditions in the world. Beyond rickets, a manifestation of severe vitamin D insufficiency recognized since the 17th century,[35] vitamin D deficiency (commonly defined as <10-25 ng/mL of total serum 25[OH]D)[21,34,36] has since been associated with an increased risk of osteoporosis, cancer, infectious disease, CVD disease, allergy, asthma, multiple sclerosis, muscle weakness, rheumatoid arthritis, and diabetes. Low vitamin D can arise from insufficient intake from nutritional sources, insufficient synthesis (via UV-B radiation of the skin), adiposity, age, physical activity, or other disease-related factors such as diabetes, bariatric surgery, fat malabsorption syndromes, and kidney disease.[14,37,38] The use of sunscreen with sun protection factor (SPF)≥30 reduces the ability of the skin to produce vitamin D by 99%, thus contributing to the pandemic.

One recent study found that vitamin D insufficiency was present in 72% of community-dwelling men older than 65 years of age, and in up to 86% of those men who were obese, lived at higher latitudes, or infrequently participated in outdoor activities.[17] Although vitamin D deficiency is less common, it is estimated to affect 26%-54% of community-dwelling older adults and 57% of hospitalized patients.[17,36,40] A recognized problem in older adults, people of all ages who live in diverse geographic locations are also susceptible, including sunny climate dwellers.[41] A study of younger adults with limited exposure to the outdoors in a northeastern urban setting reported that 32% of students and doctors aged 18-29 years were vitamin D deficient at the end of the winter.[42] In diseases including diabetes, rheumatoid arthritis, renal disease, as well as in individuals who are obese, hospitalized, pregnant, newborn, highly deficient levels of this hormone are common.[40,43-45] Current recommendations for vitamin D supplementation are largely inadequate.[17,46,47] According to Holick,[46] 25(OH)D is the most-ordered hormone assay in the US, used as the basis for treatment recommendations. However, assay results as well as cutoff levels of 25(OH)D to define the extent of vitamin D insufficiency are subject to considerable variation. Given the prevalence and breadth of illnesses potentially associated with low vitamin D, gaining a better understanding of vitamin D status to guide management of vitamin D insufficiency is a public health priority. The Institute of Medicine (IOM) has recognized that that assay variation and lack of consensus regarding cutoffs defining insufficiency/deficiency have caused confusion about the appropriate dietary intake of vitamin D.[33] The IOM has also cautioned against excessive intake due to the risks of kidney and tissue damage and have urged more targeted research in this area. Importantly, the method used to determine vitamin D status should be clinically relevant and applicable across diverse populations.

SUMMARY OF INVENTION

Described herein are methods, assays, methods of treatment, and systems related to determining the level of free and/or bioavailable vitamin D in a blood sample obtained from a subject.

In one aspect, the invention relates to an assay comprising a) analyzing a blood sample obtained from a subject to determine a level of VDBP (vitamin D binding protein) polypeptide, albumin polypeptide and total vitamin D; wherein a level of bioavailable vitamin D is:

$$= (K_{alb} \cdot [Alb] + 1) \cdot [\text{Free Vitamin } D]$$

and wherein a level of free vitamin D is:

$$= \{-\{K_{DBP} \cdot [\text{Total } DBP] - K_{DBP} \cdot [\text{Total Vitamin } D] + K_{alb} \cdot [Alb] + 1\} + \sqrt{\{(K_{DBP} \cdot [\text{Total } DBP] - K_{DBP} \cdot [\text{Total Vitamin } D] + K_{alb} \cdot [Alb] + 1)^2 + 4 \cdot (K_{DBP} \cdot K_{alb} \cdot [Alb] + K_{DBP}) \cdot ([\text{Total Vitamin } D])\}\} \div (2 \cdot \{K_{DBP} \cdot K_{alb} \cdot [Alb] + K_{DBP}\}).$$

In some embodiments, a level of bioavailable vitamin D lower than 25% of the mean value of bioavailable vitamin D in a population of healthy subjects can indicate that the subject has a vitamin D insufficiency. In some embodiments, the vitamin D can be selected from the group consisting of: 25-hydroxyvitamin D and 1,25-dihydroxyvitamin D.

In some embodiments, determining the level of VDBP polypeptide or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining the level of total vitamin D can comprise the use of a method selected from the group consisting of: radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

In some embodiments, the invention can further comprise the step of administering a vitamin D insufficiency treatment to a subject who is determined to have a vitamin D insufficiency. In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to an assay comprising; analyzing a blood sample obtained from a subject to determine a level of VDBP polypeptide, albumin polypeptide and total vitamin D; wherein a level of free vitamin D is:

$$=\{-\{K_{DBP} \cdot [\text{Total } DBP] - K_{DBP} \cdot [\text{Total Vitamin } D] + K_{alb} \cdot [Alb] + 1\} + \sqrt{\{(K_{DBP} \cdot [\text{Total } DBP] - K_{DBP} \cdot [\text{Total Vitamin } D] + K_{alb} \cdot [Alb] + 1)^2 + 4 \cdot (K_{DBP} \cdot K_{alb} \cdot [Alb] + K_{DBP}) \cdot ([\text{Total Vitamin } D])\}\} \div (2 \cdot \{K_{DBP} \cdot K_{alb} \cdot [Alb] + K_{DBP}\}).$$

In some embodiments, a level of free vitamin D lower than 25% of the mean value of free vitamin D in a population of healthy subjects can indicate that the subject has a vitamin D insufficiency. In some embodiments, the vitamin D can be selected from the group consisting of: 25-hydroxyvitamin D and 1,25-dihydroxyvitamin D.

In some embodiments, determining the level of VDBP polypeptide or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining the level of total vitamin D can comprise the use of a method selected from the group consisting of: radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

In some embodiments, the invention can further comprise the step of administering a vitamin D insufficiency treatment to a subject who is determined to have a vitamin D insufficiency. In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to a method for treating a vitamin D insufficiency in a subject comprising detecting a level of VDBP polypeptide, albumin polypeptide and total vitamin D in a blood sample obtained from a subject; wherein a level of bioavailable vitamin D is:

$$=(K_{alb} \cdot [Alb] + 1) \cdot [\text{Free Vitamin } D]$$

and wherein a level of free vitamin D is:

$$=\{-\{K_{DBP} \cdot [\text{Total } DBP] - K_{DBP} \cdot [\text{Total Vitamin } D] + K_{alb} \cdot [Alb] + 1\} + \sqrt{\{(K_{DBP} \cdot [\text{Total } DBP] - K_{DBP} \cdot [\text{Total Vitamin } D] + K_{alb} \cdot [Alb] + 1)^2 + 4 \cdot (K_{DBP} \cdot K_{alb} \cdot [Alb] + K_{DBP}) \cdot ([\text{Total Vitamin } D])\}\} \div (2 \cdot \{K_{DBP} \cdot K_{alb} \cdot [Alb] + K_{DBP}\})$$

and administering a treatment for vitamin D insufficiency to the subject if the level of bioavailable vitamin D is less than 25% of the mean value of bioavailable vitamin D in a population of healthy subjects.

In some embodiments, the vitamin D can be selected from the group consisting of: 25-hydroxyvitamin D and 1,25-dihydroxyvitamin D.

In some embodiments, determining the level of VDBP polypeptide or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining the level of total vitamin D can comprise the use of a method selected from the group consisting of: radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to a method for treating a vitamin D insufficiency in a subject comprising detecting a level of VDBP polypeptide, albumin polypeptide and total vitamin D in a blood sample obtained from a subject; wherein a level of free vitamin D is:

$$=\{-\{K_{DBP} \cdot [\text{Total } DBP] - K_{DBP} \cdot [\text{Total Vitamin } D] + K_{alb} \cdot [Alb] + 1\} + \sqrt{\{(K_{DBP} \cdot [\text{Total } DBP] - K_{DBP}}$$

$[\text{Total Vitamin } D] + K_{alb} \cdot [Alb] + 1)^2 + 4 \cdot (K_{DBP} \cdot K_{alb} \cdot [Alb] + K_{DBP}) \cdot ([\text{Total Vitamin } D])\} \} \div (2 \cdot \{K_{DBP} \cdot K_{alb} \cdot [Alb] + K_{DBP}\})$ and administering a treatment for vitamin D insufficiency to the subject if the level of free vitamin D is less than 25% of the mean value of free vitamin D in a population of healthy subjects.

In some embodiments, the vitamin D can be selected from the group consisting of: 25-hydroxyvitamin D and 1,25-dihydroxyvitamin D.

In some embodiments, determining the level of VDBP polypeptide or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining the level of total vitamin D can comprise the use of a method selected from the group consisting of: radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthma; multiple sclerosis; muscle weakness; rheumatoid arthritis and diabetes.

In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to a system for obtaining data from at least one blood sample obtained from at least one subject, the system comprising: a determination module configured to receive the at least one blood sample and perform at least one analysis on the at least one blood sample to determine a level of bioavailable or free vitamin D in the sample; a storage device configured to store data output from said determination module; and a display module for displaying a content based in part on the data output from said determination module, wherein the content comprises a signal indicative of the level of bioavailable or free vitamin D.

In some embodiments, the system further comprises a means of inputting a value for the level of one or more of VDBP polypeptide, albumin polypeptide, and total vitamin D determined to be in a test sample. In some embodiments, the content displayed on said display module further comprises a signal indicative of the subject having an increased likelihood of a vitamin D insufficiency if the level of bioavailable or free vitamin D is determined to be lower than 25% of the mean value of bioavailable vitamin D in a population of healthy subjects. In some embodiments, the content displayed on said display module further comprises a signal indicative of the subject being recommended to receive a treatment for vitamin D insufficiency.

In some embodiments, a level of free and/or bioavailable vitamin D lower than 25% of the mean value of free and/or bioavailable vitamin D in a population of healthy subjects can indicate that the subject has a vitamin D insufficiency. In some embodiments, the vitamin D can be selected from the group consisting of: 25-hydroxyvitamin D and 1,25-dihydroxyvitamin D.

In some embodiments, determining the level of VDBP polypeptide or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining the level of total vitamin D can comprise the use of a method selected from the group consisting of: radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthma; multiple sclerosis; muscle weakness; rheumatoid arthritis and diabetes.

In some embodiments, the invention can further comprise the step of administering a vitamin D insufficiency treatment to a subject who is determined to have a vitamin D insufficiency. In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to a method of treatment comprising: analyzing a blood sample obtained from a subject to determine a level of free or bioavailable vitamin D; wherein a level of free or bioavailable vitamin D lower than 25% of the mean value of free or bioavailable vitamin D in a population of healthy subjects indicates that the subject has a vitamin D insufficiency; and administering a vitamin D insufficiency treatment to a subject who is determined to have a vitamin D insufficiency.

In some embodiments, the vitamin D can be selected from the group consisting of: 25-hydroxyvitamin D and 1,25-dihydroxyvitamin D.

In some embodiments, determining of the level of free and/or vitamin D can comprise the use of a method selected from the group consisting of: immunoassay; two-step immunoassay with antibody capture; one-step immunoassay with immobilized antibody and competitive detection; one-step immunoassay with immobilized competitior and labeled antibody; fluorescence polarization immunoassay; differential precipitation (immunoprecipitation, affinity precipitation); immunodepletion; and affinity binding chromatography; and a method selected from the group consisting of: radioimmunoassay; chemiluminescent immunosorbent assay; electrochemiluminescent immunosorbent assay; fluorescent immunosorbent assay; dye linked immunosorbent assay; liquid chromatography tandem mass spectroscopy and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

In some embodiments, the treatment can comprise administering a compound selected from the group consisting of: calcitriol; dihydrotachysterol; doxercalciferol; paricalcitol; cholecalciferol and ergocalciferol.

In another aspect, the invention relates to an assay comprising analyzing a blood sample obtained from a subject to determine a level of free vitamin D and albumin polypeptide; wherein a level of bioavailable vitamin D is:

$$=(K_{alb}*[Alb]+1)*[\text{Free Vitamin } D].$$

In some embodiments, a level of bioavailable vitamin D lower than 25% of the mean value of bioavailable vitamin D in a population of healthy subjects can indicate that the subject has a vitamin D insufficiency. In some embodiments, the vitamin D can be selected from the group consisting of: 25-hydroxyvitamin D and 1,25-dihydroxyvitamin D.

In some embodiments, determining the level of albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

In some embodiments, determining of the level of free and/or vitamin D can comprise the use of a method selected from the group consisting of: immunoassay; two-step immunoassay with antibody capture; one-step immunoassay with immobilized antibody and competitive detection; one-step immunoassay with immobilized competitior and labeled antibody; fluorescence polarization immunoassay; differential precipitation (immunoprecipitation, affinity precipitation); immunodepletion; and affinity binding chromatography; and a method selected from the group consisting of: radioimmunoassay; chemiluminescent immunosorbent assay; electrochemiluminescent immunosorbent assay; fluorescent immunosorbent assay; dye linked immunosorbent assay; liquid chromatography tandem mass spectroscopy and high-pressure liquid chromatography.

In some embodiments, an insufficiency of vitamin D can indicate an increased risk of a condition selected from the group consisting of: decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

In some embodiments, the invention can further comprise the step of administering a vitamin D insufficiency treatment to a subject who is determined to have a vitamin D insufficiency. In some embodiments, the treatment can comprise administering a compound selected from the group consisting of: calcitriol; dihydrotachysterol; doxercalciferol; paricalcitol; cholecalciferol and ergocalciferol.

DETAILED DESCRIPTION OF THE INVENTION

Figure 1:
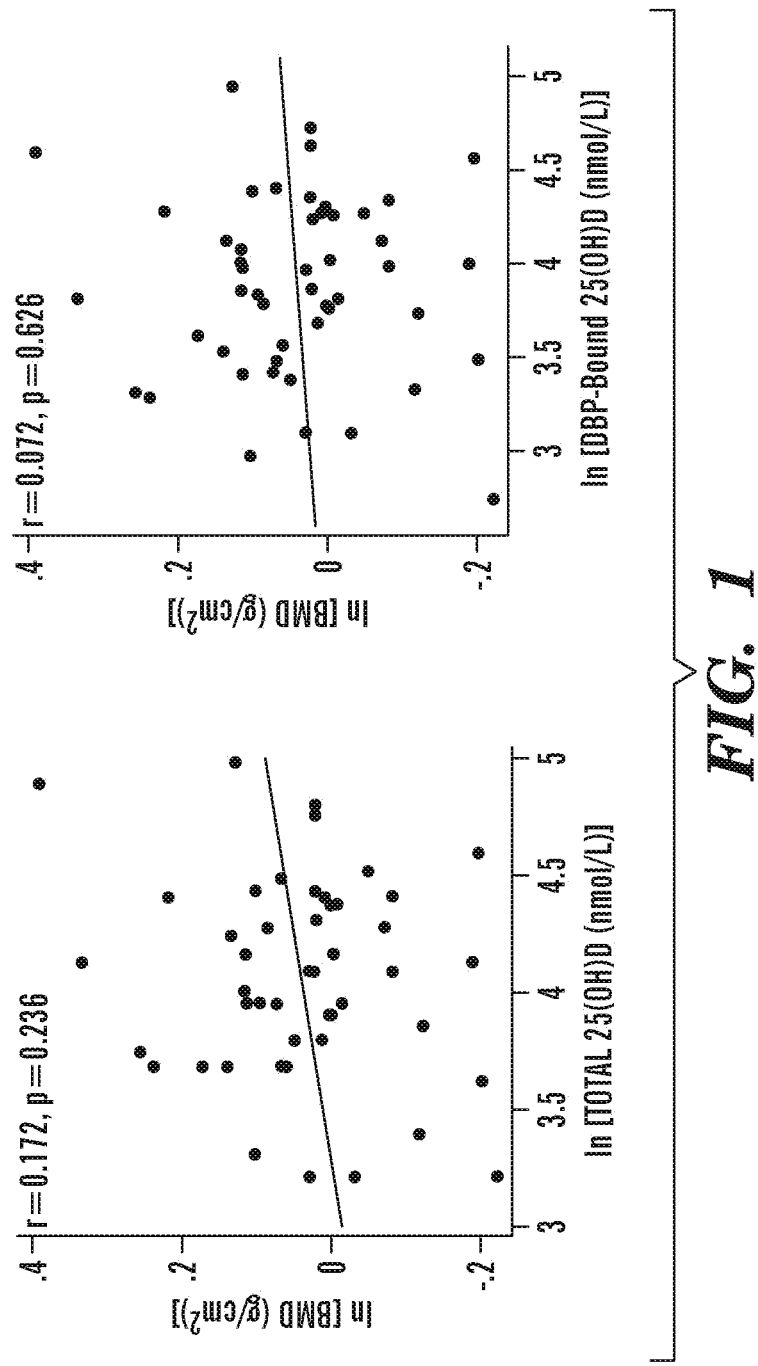
FIG. 1 depicts the relationship between total and free 25-hydroxyvitamin D and lumbar spine bone mineral density. DBP-Bound, Free, and Bioavailable 25-hydroxyvitamin D (25(OH)D) levels were calculated from measured total 25(OH)D and vitamin D binding protein (DBP) levels. Total 25(OH)D and DBP-bound 25(OH)D were not associated with lumbar spine bone mineral density (BMD). Free 25(OH)D and bioavailable 25(OH) D were positively correlated with lumbar spine BMD.
Figure 1:
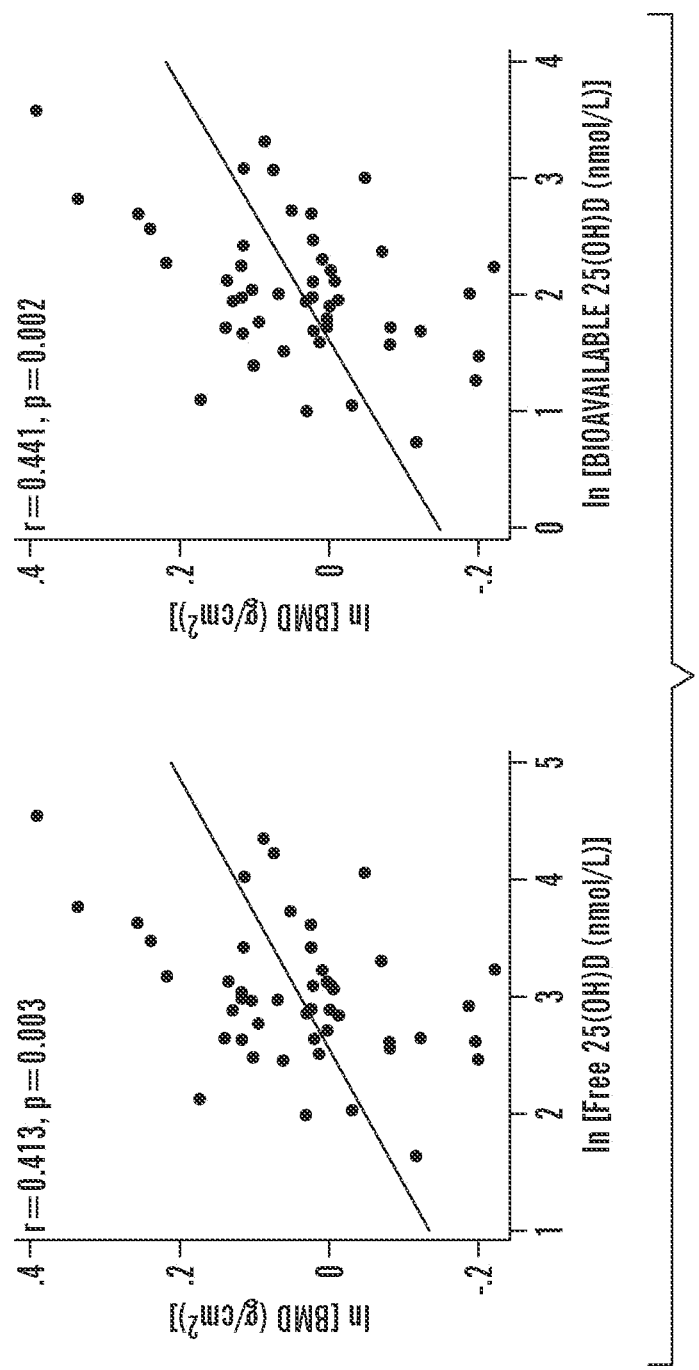

Aspects of the invention described herein include assays. Systems, and methods of treatment which are based on the inventors' discovery that total serum levels of vitamin D, the currently used clinical parameter, correlate poorly with measures of health such as bone mineral density and parathyroid hormone levels. The inventors have found that levels of bioavailable and free vitamin D correlate better with the same measures of health and are therefore more indicative of whether a subject has sufficient vitamin D levels. Described herein are assays for measuring bioavailable and free vitamin D and methods of treating subjects for vitamin D insufficiency.

Materials, procedures and considerations necessary to understand and use the disclosed methods are described in the following, as are experimental results and non-limiting examples that demonstrate and illustrate various embodiments of the methods and assays described.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word or is intended to include and unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to a reference level, or any decrease between 10-99% as compared to a reference level.

The terms "increased", "increase" or "enhance" or "activate" or "promote" are all used herein to generally mean an increase by a statically significant amount; for the avoidance of any doubt, the terms "increased", "increase" or "enhance" or "activate" or "promote" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "proteins" and "polypeptides" are used interchangeably herein to designate a series of amino acid residues connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "pharmaceutical composition" refers to the active agent in combination with a pharmaceutically acceptable carrier as commonly used in the pharmaceutical industry.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient or is toxic to the subject, use thereof in the therapeutic compositions is contemplated. Supplementary active ingredients can also be incorporated into the compositions.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above. In certain embodiments, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of vitamin D insufficiency. In addition, the methods described herein can be used to treat domesticated animals and/or pets. A subject can be male or female. A subject can be one who has been previously diagnosed with or identified as suffering from or having vitamin D insufficiency or one or more diseases or conditions associated with a vitamin D insufficiency, and optionally, but need not have already undergone treatment for vitamin D insufficiency or the one or more diseases or conditions associated with a vitamin D insufficiency. A subject can also be one who has been diagnosed with or identified as suffering from vitamin D insufficiency or one or more diseases or conditions associated with a vitamin D insufficiency, but who shows improvements in known vitamin D insufficiency risk factors as a result of receiving one or more treatments for vitamin D insufficiency or one or more diseases or conditions associated with a vitamin D insufficiency. Alternatively, a subject can also be one who has not been previously diagnosed as having vitamin D insufficiency or one or more diseases or conditions associated with a vitamin D insufficiency. For example, a subject can be one who exhibits one or more risk factors for vitamin insufficiency or one or more diseases or conditions associated with a vitamin D insufficiency or a subject who does not exhibit vitamin D insufficiency risk factors.

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a difference of at least two standard deviations (2SD).

Vitamin D Insufficiency

Aspects of the invention described herein include assays directed to determining whether a subject has a vitamin D insufficiency and methods of treating these conditions. As used herein, "vitamin D" refers to any of several forms of D vitamins including vitamin D1, D2, D3, D4 and isomers or derivatives thereof. Non-limiting examples of forms of vitamin D include vitamin D2 (ergocalciferol) which is produced by plants, vitamin D3 (cholecalciferol) which is produced by animals. Both vitamin D2 and D3 are hydroxylated in the liver to form, respectively, 25(OH)D2 (25-hydroxyvitamin D2) and 25(OH)D3 (25-hydroxyvitamin D3 or calcidiol), which can be referred to collectively as 25(OH)D. 25(OH)D is the primary transport form of vitamin D in the body and is the prohormone of the active vitamin D hormones. Further hydroxylation, primarily in the kidneys, converts 25(OH)D to 1,25(OH)$_2$D (including 1,25(OH)$_2$D3 (calcitriol) and 1,25 (OH)$_2$D2). All of the foregoing forms of vitamin D are encompassed by the term "vitamin D" as used herein. In some embodiments, the level of vitamin D that is determined is the level of 25-(OH)D. In some embodiments, the level of vitamin D that is determined is the level of 25-(OH)D2. In some embodiments, the level of vitamin D that is determined is the level of 25-(OH)D3. In some embodiments, the level of vitamin D that is determined is the level of 1,25-(OH)$_2$D. In some embodiments, the level of vitamin D that is determined is the level of 1,25-(OH)$_2$D2. In some embodiments, the level of vitamin D that is determined is the level of 1,25-(OH)$_2$D3.

Vitamin D hormones influence bone mineralization and a number of aspects of blood chemistry, including blood calcium levels and blood phosphorus levels. Diseases and conditions which are caused by or associated with insufficient levels of vitamin D are referred to herein as "vitamin D-associated diseases." Insufficient levels of vitamin D are associated with secondary hyperparathyroidism, parathyroid gland hyperplasia, elevated parathyroid hormone levels. hypocalcemia, chronic kidney disease (CKD), renal disease, end-stage renal disease, chronic kidney disease-associated mineral and bone disorder, psoriasis, low bone mineral density, bone resorption and metabolic bone diseases such as fibrogenesis imperfecta ossium, osteitis fibrosa cystica, osteomalacia, rickets, osteoporosis, osteosclerosis, non-traumatic fractures of the spine and hip, renal osteodystrophy, and extraskeletal calcification. Secondary hyperparathyroidism (SHPT) increases bone turnover, and if left untreated, can impair mineralization and decrease bone mass. Patients with SHPT have increased bone turnover and decreased bone mass that can eventually progress to osteomalacia. Osteomalacia is a severe defect in or absence of bone mineralization occurring when both vitamin D and dietary calcium levels are markedly reduced. Osteoporosis, defined as a deficiency of normal bone within bone tissue, can result either from a low calcium diet with replete vitamin D levels or with low vitamin D and adequate dietary calcium. Low serum 25(OH)D increases the risk of osteoporotic fractures, especially in older adults, and vitamin D and calcium supplementation at sufficient doses reduces the risk. A number of "non-classical" biologic effects have been reported for vitamin D beyond its "classical" effects on the parathyroid hormone system. Such effects have been reported in connection with cellular growth and differentiation, cellular proliferation, red blood cell formation, hair growth, muscular function, blood pressure, fibrosis, the immune system and the cardiovascular system, including the renin-angiotensin system. Vitamin D insufficiency has been implicated in the development or progression of, for example, infection, cardiovascular disease, allergy, asthama obesity, diabetes, muscle weakness, multiple sclerosis, rheumatoid arthritis and cancer.

Vitamin D insufficiency can be caused by insufficient exposure to sunlight, insufficient dietary intake of vitamin D, or conditions or clinical procedures, such as bariatric surgery, that result in reduced intestinal absorption of fat soluble vitamins such as vitamin D. Vitamin D levels are traditionally measured as the level of total serum 25(OH)D. Although total serum 25(OH)D is currently the most widely accepted assay for determining vitamin D status, it is subject to tremendous variation in results and interpretation, and may not be clinically relevant across all populations. Aspects of the invention described herein are directed to an assay for determining whether a subject is vitamin D insufficient by measuring the levels of bioavailable or free vitamin D, as opposed to total serum vitamin D.

As used herein, "vitamin D insufficiency" refers to suboptimal levels of vitamin D that can be associated with an increased risk of developing one or more of the conditions or diseases in which low vitamin D levels have been implicated, which are described above herein. Subjects with a vitamin D insufficiency may not have any symptoms, markers or signs of a vitamin D-associated disease or may have symptoms, markers or signs of one or more vitamin D-associated diseases. A subject who has a vitamin D insufficiency can be a subject who has a level of bioavailable or free vitamin D which is 25% or lower than the mean level of that form of vitamin D measured in a healthy population of subjects. For example, a subject who has a level of bioavailable or free vitamin D which is 25%, or 20% or 15% or 10% or 5% or lower than the mean level of that form of vitamin D in a population of healthy subjects has an insufficient level of vitamin D.

A healthy subject can be one who does not display any markers, signs or symptoms of a vitamin D-associated disease or condition and who is not at risk of having a vitamin D insufficiency. By way of non-limiting example, a healthy subject will not exhibit signs or symptoms of rickets, which include, for example delayed growth, pain in the spine, pelvis or legs, muscle weakness, or skeletal deformities such as bowed legs, abnormal curvature of the spine, thickened wrists and ankles, and/or projection of the breastbone. Risk factors for vitamin D insufficiency are well-known in the art and can include, but are not limited to, not drinking vitamin D fortified milk (e.g. lactose intolerant subjects, subjects with milk allergies, some vegetarians, and breast-fed infants); dark skin; old age (e.g. the elderly have a reduced ability to synthesize vitamin D and can be more likely to stay indoors), chronic or acute or severe illness (conditions which make it likely the subject will stay indoors, in hospitals, in intensive care facilities, or institutional and assisted-care facilities, including subjects with Alzheimer's disease or who are mentally ill); covering all exposed skin (such as members of certain religions or cultures); regular use of sunscreen (e.g., the application of sunscreen with a Sun Protection Factor (SPF) value of 8 reduces production of vitamin D by 95%, and higher SPF values may further reduce vitamin D); having or having been diagnosed with a fat malabsorption syndrome (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); having had small bowel resections; taking medications that increase the catabolism of vitamin D, including phenytoin, fosphenytoin, phenobarbital, carbamazepine, and rifampin; taking medications that reduce absorption of vitamin D, including cholestyramine, colestipol, orlistat, mineral oil, and fat substitutes; taking medications that inhibit activation of vitamin D, including ketoconazole; taking medications that decrease calcium absorption, including corticosteroids; having or having been diagnosed as having gum disease, diabetes mellitus, insulin resistance syndrome, endothelial dysfunction (vitamin D deposited in body fat stores is less bioavailable) cardiovascular disease, artherosclerosis heart failure or osteoporosis; being obese; or being a postmenopausal woman.

Bioavailable Vitamin D

The assays and methods of treatments described herein are based on the inventors' discovery that the level of bioavailable and/or free vitamin D in the blood of a subject has a more significant correlation to measures of health such as bone mineral density and parathyroid hormone levels than does the level of total serum vitamin D.

In the blood stream, vitamin D can exist in one of three states; 1) bound by vitamin D binding protein, 2) bound by albumin protein or 3) unbound. As used herein, "vitamin D binding protein", "VDBP" or "DBP" refers to a polypeptide of any of SEQ ID NO: 1, 2 or 3 (NCBI Gene ID No: 2638) and naturally occurring variants (e.g. alleles), homologs and functional derivatives thereof. VDBP binds vitamin D tightly, with a $K_D=0.7\times10^9$ $M^{-1}$ (for human VDBP). The fraction of vitamin D which is bound to VDBP is referred to herein as "$D_{VDBP}$", "$D_{DBP}$", "Vitamin $D_{DBP}$" or "Vitamin $D_{VDBP}$." As used herein, "albumin" refers to the polypeptide of any of SEQ ID NO: 4, 5 or 6 (NCBI Gene ID No: 213) and naturally occurring variants (e.g. alleles), homologs and functional derivatives thereof. Albumin binds vitamin D less tightly than VDBP, with a $K_D=6\times10^5$ $M^{-1}$ (for human albumin). The fraction of vitamin D which is bound to albumin is referred to herein as "$D_{albumin}$", "$D_{Alb}$", "vitamin $D_{albumin}$" or "vitamin $D_{Alb}$." Unbound vitamin D is also referred to herein as "free vitamin D" or "D." As used herein, "bioavailable vitamin D" refers to, collectively, free vitamin D and vitamin D bound to albumin. Bioavailable vitamin D does not comprise the fraction of vitamin D which is bound to VDBP. Bioavailable vitamin D is interchangeably referred to herein as "$V_{Bio}$" and "Vitamin $D_{Bio}$".

An Assay for Bioavailable Vitamin D

Aspects of the invention described herein are directed to assays to determine the level of bioavailable and/or free vitamin D in a blood sample obtained from a subject.

In some embodiments, the level of bioavailable and/or free vitamin D is determined by first determining the level of VDBP polypeptide, albumin polypeptide and total vitamin D in a blood sample obtained from a subject. The level of free and bioavailable vitamin D can then be calculated using these values and the binding constants of VDBP and albumin for vitamin D. For human proteins, the binding constants are, respectively, $0.7\times10^9$ $M^{-1}$ and $6\times10^5$ $M^{-1}$.

As used herein a "blood sample" refers to any amount of blood or a fraction thereof that has been obtained from a subject. In some embodiments, the blood sample can comprise whole blood or a fraction thereof, e.g. serum or plasma. In some embodiments, the blood sample is contacted with an anticoagulant or preservative prior to performing an assay as described herein. Non-limiting examples of anticoagulants and preservatives include CPD, CP2D (Citrate Phosphate Double Dextrose), CPDA-1, CDP/ADSOL®, CDP/Optisol®, AS-3 (Additive Solution 3, Haemonetics Corp Braintree Mass.) and SAG-M.

In some embodiments, a blood sample can be stored prior to being used in an assay as described herein. In some embodiments the blood sample can be stored for any given period of time, e.g. minutes, hours, days, weeks, up to months, prior to use in an assay as described herein. In one embodiment, the blood sample is frozen. In one embodiment, the blood sample is not frozen.

In some embodiments, the assays described herein are performed on a whole blood sample. In some embodiments, the assays described herein are performed on the plasma fraction of a blood sample. In some embodiments, the assays described herein are performed on the serum fraction of a blood sample.

The level of VDBP and/or albumin polypeptide present in the blood sample obtained from a subject can be determined by any method for determining the level of a specific polypeptide known in the art. In some embodiments, the assay is performed on an automated analyzer. Non-limiting examples of methods that can be used in the methods and assays described herein include enzyme linked immunosorbent assay; dye-based photometric assay; western blot; immunoprecipitation; radioimmunological assay (RIA); radioimmunometric assay; chemiluminescent immunosorbent assay; electrochemiluminescent immunosorbent assay; fluorescent immunosorbent assay; dye linked immunosorbent assay; immunoturbidimetric assay; immunonephelometric assay; immunofluorescence assay and mass spectroscopy. Various methods of producing antibodies with a known antigen (e.g. a peptide comprised by the polypeptides of SEQ ID Nos. 1-6) are well-known to those ordinarily skilled in the art (see Antibodies: A Laboratory Manual (Harlow & Lane eds., 1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art. Antibodies specific for albumin and VDBP are commercially available (e.g. Cat. #ab112888 and ab23484, respectively, Abcam; Cambridge, Mass.).

In some embodiments, albumin levels can be determined by dye-based photometric assays on an automated analyzer. Dye-based photometric assays are commercially available (e.g. the Albumin FS™ kits; DiaSys Diagnostic Systems Gmb; Holzheim, Germany or the Albumin reagent, Cat #OSR6102; Beckman Coulter; Brea, Calif.). Automated analyzers are commercially available (e.g. the AU2700 or AU5400 from Beckman Coulter; Brea, Calif.). Systems which are designed specifically for the determination of serum albumin levels are also available commercially (e.g. the Careside Analyzer™, Careside Inc., Culver City, Calif.). In some embodiments, the level of albumin levels can be determined using immunoassays, e.g. the Human Serum Albumin ELISA Kit (Cat #1190; Alpha Diagnostic International; San Antonio, Tex.).

In some embodiments, VDBP levels can be determined by ELISA. ELISA assays for VDBP are commercially available (e.g. Cat #DVDBP0; R&D Systems; Minneapolis, Minn.). In some embodiments, the assay is conducted after diluting serum samples 1 to 2,000 in Calibrator Diluent RD6-11 (R&D Systems Part Number 895489). ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904; which are incorporated by reference herein in their entirety.

The level of total vitamin D present in the blood sample obtained from a subject can be determined by any method known in the art. Non-limiting examples of methods that can be used in the methods and assays described herein include radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography. In some embodiments, the level of total vitamin D in a sample is determined by liquid chromatography tandem mass spectrometry (LC-MS). In some embodiments, the level of total vitamin D in a sample is determined by high performance liquid chromatography/mass spectrophotometry. In some embodiments, the level of total vitamin D in a sample is determined by radioimmunoassay. In some embodinents, the level of total vitamin D in a sample is determined using a commercially available radioimmunoassay (e.g. DiaSorin Inc, Stillwater, Minn., USA). In some embodiments, the level of total vitamin D in a sample is determined using a commercially available immunluminometric assay (e.g. Cat No 310600; DiaSorin Inc.; Stillwater MN.). The method of measuring total vitamin D in a blood sample obtained from a subject can also include liquid chromatography tandem mass spectroscopy as described in U.S. Pat. No. 7,700,365, which is included by reference herein in its entirety.

Mass spectroscopy methods are well known in the art and have been used to quantify and/or identify biomolecules. In some embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra.

In some embodiments, the level of total vitamin D which is determined can comprise one or more forms of vitamin D selected from the group consisting of 25-hydroxyvitamin D (25(OH)D); 1,25-dihydroxyvitamin D (1,25-(OH)$_2$D); 25(OH)D2; 25(OH)D3; 1,25(OH)$_2$D2; 1,25-(OH)$_2$D3; vitamin D1; vitamin D2; vitamin D3; vitamin D4; ergocalciferol; cholecalciferol; calcidiol and calcitriol. In some embodiments, the level of total vitamin D which is determined can comprise 25-hydroxyvitamin D (25(OH)D). In some embodiments, the level of total vitamin D which is determined can comprise 25-hydroxyvitamin D2 (25(OH)D2). In some embodiments, the level of total vitamin D which is determined can comprise 25-hydroxyvitamin D3 (25(OH)D3). In some embodiments, the level of total vitamin D which is determined can comprise 1,25-dihydroxyvitamin D (1,25-(OH)$_2$D). In some embodiments, the level of total vitamin D which is determined can comprise 1,25-dihydroxyvitamin D2 (1,25-(OH)$_2$D2). In some embodiments, the level of total vitamin D which is determined can comprise 1,25-dihydroxyvitamin D3 (1,25-(OH)$_2$D3).

In some embodiments, once the levels of VDBP polypeptide, albumin polypeptide and total vitamin D in a blood sample obtained from a subject are determined, the level of free and/or bioavailable vitamin D can be determined. The level of free vitamin D can be calculated using Equation 8, the derivation of which is described in Example 1 herein.

$$\text{Free Vitamin } D = \{-\{K_{DBP} \cdot [\text{Total } DBP] - K_{DBP} \cdot [\text{Total Vitamin } D] + K_{alb} \cdot [Alb] + 1\} + \sqrt{\{(K_{DBP} \cdot [\text{Total } DBP] - K_{DBP} \cdot [\text{Total Vitamin } D] + K_{alb} \cdot [Alb] + 1)^2 + 4 \cdot (K_{DBP} \cdot K_{alb} \cdot [Alb] + K_{DBP}) \cdot ([\text{Total Vitamin } D])\}\} \div (2 \cdot \{K_{DBP} \cdot K_{alb} \cdot [Alb] + K_{DBP}\}).$$ (Eq. 8)

The level of bioavailable vitamin D can be calculated using Equation 9, the derivation of which is described in Example 1 herein.

$$\text{Bioavailable Vitamin } D = (K_{alb} \cdot [Alb] + 1) \cdot [\text{Free Vitamin } D]$$ (Eq. 9)

In some embodiments, the level of free (unbound) and/or bioavailable vitamin D can be determined directly. In some embodiments, the level of free vitamin D can be determined directly and used to calculate the level of bioavailable vitamin D. In some embodiments, the level of free vitamin D and the level of albumin polypeptide can be determined directly and used to calculate the level of bioavailable vitamin D. As used herein "determined directly" refers to determining the level of a first form of a vitamin or polypeptide by measuring or detecting the level of the first form of a vitamin or polypeptide as opposed to calculating the level of the first form of a vitamin or polypeptide using the level of a second or further form of a vitamin or polypeptide which was directly determined.

Direct measurement of the level of free and/or bioavailable vitamin D can be accomplished by a number of methods. Non-limiting examples of methods for direct measurement of the level of free vitamin D include the following. 1) Vitamin D complexed with VDBP can be depleted from a sample using immunodepletion or affinity binding chromatography to deplete VDPB from the sample. The remaining vitamin D (the bioavailable fraction) can then be measured according to any of the methods described elsewhere herein. 2) Vitamin D complexed with VDBP can be depleted from a sample using differential precipitation of VDBP with antibodies (immunoprecipitation), actin (affinity precipitation) with or without precipitating buffers (e.g. polyethylene glycol, ammonium sulfate) followed by centrifugal separation from free and/or bioavailable vitamin D and measurement of remaining vitamin D fraction according to any of the methods described elsewhere herein. 3) Immunoassays can also be used (see for example, Ekins et al. J Endocrinol Invest. 9 Suppl 4:3-15. 1986; which is incorporated by reference herein in its entirety). Immunoassays capitalize on the idea that free analyte may be measured using lower affinity antibodies which do not "strip" the vitamin from its high affinity binding protein. Free and/or bioavailable vitamin D can be measured directly using several competitive immunoassay approaches described below and in (Christofides, Nic D. *The Immunoassay Handbook,* 3$^{rd}$ Ed. Editor David Wild, Elsevier Ltd, 2005; which is incorporated by reference herein in its entirety) These methods are all based upon two principals: (1) Antibodies will differentiate between free and protein-bound analytes if the reaction conditions (pH, temperature, buffers) do not interfere with binding between the vitamin and its binding protein, and (2) The total antibody binding capacity (affinity constant times antibody concentration) does not significantly deplete the total vitamin D concentration and thus does not "strip" the protein-bound vitamin D. This may be achieved using an antibody with relatively low affinity ($\sim 10^{10}$ L/M) for the vitamin D ligand and/or limited assay reaction times which allow for binding of free and albumin-bound vitamin D but are too short to allow dissociation of VDBP-bound vitamin D.

Specific immunoassay designs that can be used include the following: A) Two-step measurement of free and/or bioavailable vitamin D with antibody capture—(1) capture of free and/or bioavailable vitamin D with immobilized vitamin D-binding antibody, (2) wash away unbound vitamin D and VDBP, (3) detection of bound vitamin D by competitive binding with labeled vitamin D (or labeled vitamin D analog that also binds the antibody). B) One-step measurement of free and/or bioavailable vitamin D with immobilized vitamin D-binding antibody and competitive detection using labeled vitamin D (or labeled vitamin D analog). C) One-step measurement of free and/or bioavailable vitamin D with immobilized vitamin D or vitamin D analog and labeled vitamin D-binding antibody. Free and/or bioavailable vitamin D from a sample competes with the immobilized vitamin D for binding to the labeled antibody. D) One-step measurement of free and/or bioavailable vitamin D with fluorescence polarization immunoassay (Mendel C M. Clin Chem. 38(9):1916-7. 1992; which is incorporated by reference herein in its entirety). Free and/or bioavailable vitamin D and fluorescently labeled vitamin D analog compete for binding to antibody and polarized fluorescence indicates relative amount of free and/or bioavailable vitamin D competing for binding sites.

In some embodiments, determining of the level of free and/or vitamin D can comprise the use of a method selected from the group consisting of: immunoassay; two-step immunoassay with antibody capture; one-step immunoassay with immobilized antibody and competitive detection; one-step immunoassay with immobilized competitior and labeled antibody; fluorescence polarization immunoassay; differential precipitation (immunoprecipitation, affinity precipitation); immunodepletion; and affinity binding chromatography; and a method selected from the group consisting of: radioimmunoassay; chemiluminescent immunosorbent assay; electrochemiluminescent immunosorbent assay; fluorescent immunosorbent assay; dye linked immunosorbent assay; liquid chromatography tandem mass spectroscopy and high-pressure liquid chromatography.

In some embodiments, when the level of bioavailable or free vitamin D determined to be in the blood sample of a subject is less than 25% of the mean value of bioavailable or free vitamin D in a population of healthy subjects, the subject is likely to have a vitamin D insufficiency. In some embodiments, when the level of bioavailable or free vitamin D determined to be in the blood sample of a subject is less than 25% of the mean value of bioavailable or free vitamin D in a population of healthy subjects, the subject is indicated to have a vitamin D insufficiency. In some embodiments, when the level of bioavailable or free vitamin D determined to be in the blood sample of a subject is less than 25% of the mean value of bioavailable or free vitamin D in a population of healthy subjects, the subject has an increased likelihood of having or developing a vitamin D-associated disease. In some embodiments, when the level of bioavailable or free vitamin D determined to be in the blood sample of a subject is less than 25% of the mean value of bioavailable or free vitamin D in a population of healthy subjects, the subject is in need of a treatment for vitamin D insufficiency. In some embodiments, when the level of bioavailable or free vitamin D determined to be in the blood sample of a subject is less than 25% of the mean value of bioavailable or free vitamin D in a population of healthy subjects, the subject has a greater likelihood of being in need of a treatment for vitamin D insufficiency.

In some embodiments, when the level of bioavailable or free vitamin D determined to be in the blood sample of a subject is more than 25% of the mean value of bioavailable or free vitamin D in a population of healthy subjects, the subject is not treated for vitamin D insufficiency.

Methods of Treating Vitamin D Insufficiency

Aspects of the invention described herein are directed to methods of treating a vitamin D insufficiency comprising detecting the level of bioavailable or free vitamin D in a blood sample obtained from a subject and administering a treatment for vitamin D insufficiency if the level of bioavailable vitamin D is below 25% of the mean value of bioavailable vitamin D in a population of healthy subjects. In some embodiments, the level of bioavailable or free vitamin D is determined by determining the level of VDBP polypeptide, albumin polypeptide and total vitamin D in a blood sample obtained from a subject and calculating the level of free and/or bioavailable vitamin D as described above herein. In some embodiments, the level of free (unbound) and/or bioavailable vitamin D can be determined directly. In some embodiments, the level of free vitamin D can be determined directly and used to calculate the level of bioavailable vitamin D. In some embodiments, the level of free vitamin D and the level of albumin polypeptide can be determined directly and used to calculate the level of bioavailable vitamin D.

In some embodiments, a treatment for vitamin D insufficiency can include, for example, compounds which increase the level of vitamin D, bioavailable vitamin D and/or free vitamin D in the subject by providing one or more forms of vitamin D, stimulating the endogenous production of vitamin D, stimulating the production of active forms of vitamin D and/or inhibiting the metabolism of vitamin D. Many naturally-occurring forms of vitamin D, derivatives and analogs thereof can be administered to subjects in need of a vitamin D insufficiency treatment. In some embodiments, any form of vitamin D or a derivative or analog thereof may be used provided that it exhibits one or more activities of naturally-occurring active vitamin D (e.g. increases intestinal calcium absorption, serum calcium levels or bone mineralization) or is metabolized to a compound that exhibits such activity. Non-limiting examples of such compounds include alfacalcidol; calcifediol; calcipotriene; calcidiol; calcitriol (Rocaltrol; Roche); dihydrotachysterol (DHT™ and DHT Intensol™; Roxane Laboratories); doxercalciferol (Hectorol®; Genzyme); paricalcitol (Zemplar®; Abbott Laboratories); cholecalciferol (Delta D3™; Freeda Vitamins Inc.) and ergocalciferol (Drisdol; Sanofi). Cholecalciferol and ergocalciferol are available as dietary supplements. Further non-limiting examples include 5,6-trans-cholecalciferols; 5,6-trans-ergocalciferols; fluorinated cholecalciferols; side chain homologated cholecalciferols; side chain-truncated cholecalciferols; 19-nor cholecalciferols and ergocalciferols; 10,19-dihydovitamin D compounds; 25-hydroxyvitamin D3; 25-hydroxyvitamin D2; 24, 24-difluoro-25-hydroxyvitamin D3; 24-fluoro-25-hydroxyvitamin D3; 26,26,26,27,27,27hexafluoro-25-hydroxyvitamin D3; 24-25-dihydroxyvitamin D3; d5,26dihydroxyvitamin D3; 23,25,26-trihydroxyvitamin D3; 25-hydroxyvitamin D3; the side chain, nor, dinor, trinor and tetranoranalogs of 25-hydroxyvitamin D3, 24-homo-1,25-dihydroxyvitamin D3; 24-dihomo-1,25-dihydroxyvitamin D3; 24-trihomo-1,25-dihydroxyvitamin D3; as well as the corresponding 19-nor compounds of those listed above.

Vitamin D activity can be assayed by a number of methods known in the art. A non-limiting example of an assay to determine if a compound has vitamin D activity or is metabolized in the subject's body to a compound having vitamin D activity is described in U.S. Pat. No. 5,532,229 which is incorporated by reference herein in its entirety. Briefly, the compound is administered and the levels of serum calcium are determined by chemical colorimetry or by treating with nitric acid and measuring atomic absorption. Administration of a compound having vitamin D activity or that is metabolized to a compound having vitamin D activity will increase the serum calcium levels. Other non-limiting examples of assays for vitamin D activity include bone mineral density as measured by x-ray absorptiometry (DEXA) or measurement of serum osteocalcin (see U.S. Pat. No. 5,972,917 which is incorporated by reference herein in its entirety).

The dosage of a treatment for vitamin D insufficiency can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen.

The dosage ranges for the administration of a treatment for vitamin D insufficiency depend upon the form of the treatment for vitamin D insufficiency, and its potency, as described further herein, and are amounts large enough to produce the desired effect in which the symptoms, markers, or signs of vitamin D insufficiency are reduced. In some embodiments, the symptoms, markers, or signs of vitamin D insufficiency can include the level of bioavailable or free vitamin D determined according to the methods described herein. The dosage should not be so large as to cause substantial adverse side effects. Generally, the dosage can vary with the age, condition, and sex of the patient and can be determined by one of ordinary skill in the art. The dosage can also be adjusted by the individual physician in the event of any complication or based upon the subject's sensitivity to the treatment. By way of non-limiting example, forms of vitamin D or a derivative or analog thereof are typically administered in a therapeutically effective amount of from about 0.1 μg to about 2 mg per day depending upon the compound being administered.

In some embodiments, a vitamin D insufficiency treatment can be administered over a period of time, such as over a 5 minute, 10 minute, 15 minute, 20 minute, or 25 minute period. In some embodiments, the administration can be repeated, for example, on a regular basis, such as hourly for 3 hours, 6 hours, 12 hours or daily or longer or such as biweekly (i.e., every two weeks) for one month, two months, three months, four months or longer. In some embodiments, when multiple doses are administered, the doses can be separated from one another by, for example, six hours, one day, two days, one week, two weeks, one month, or two months.

After an initial treatment regimen, the treatments can be administered on a less frequent basis. For example, after administration biweekly for three months, administration can be repeated once per month, for six months or a year or longer. In some embodiments, administration can be chronic, e.g., one or more doses daily over a period of weeks or months.

Administration of a treatment for vitamin D insufficiency can reduce levels of a marker or symptom of vitamin D insufficiency or a disease or condition associated with vitamin D insufficiency by at least 10%, at least 15%, at least 20%, at least 25%, at least 30%, at least 40%, at least 50%, at least 60%, at least 70%, at least 80% or at least 90% or more. As used herein, the phrase "therapeutically effective amount", "effective amount" or "effective dose" refers to an amount that provides a therapeutic benefit in the treatment or management of vitamin D insufficiency. Vitamin D insufficiency can be determined according to the methods described herein and a therapeutically effective amount can be an amount that provides a statistically significant improvement in the level of bioavailable or free vitamin D as determined according to the methods described herein. Determination of a therapeutically effective amount is well within the capability of those of ordinary skill in the art. Generally, a therapeutically effective amount can vary with the subject's history, age, condition, and gender, as well as the severity and type of the medical condition in the subject, and administration of other pharmaceutically active agents.

In some embodiments, the administration is repeated until the level of bioavailable or free vitamin D, as determined according to the methods described herein, no longer indicates that the subject is vitamin D insufficient.

It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

Alternative methods of treating a subject for a vitamin D insufficiency can include, by way of non-limiting example, exposure to sunlight or administration of a CYP24 inhibitor (see U.S. patent application Ser. No. 12/935,139); dentonin peptides (see U.S. patent application Ser. No. 10/360,202); IL-10 or IL-4 polypeptides or TNF-α inhibitors (see U.S. patent application Ser. No. 10/170,746); or PHEX polypeptides as described in U.S. patent application Ser. No. 10/360, 202.

With respect to the therapeutic methods of the invention, unless otherwise specified, it is not intended that the administration of the vitamin D insufficiency treatment be limited to a particular mode of administration, dosage, or frequency of dosing; the present invention contemplates all modes of administration, including intramuscular, intravenous, intraperitoneal, intravesicular, intraarticular, topically, subcutaneous, orally or any other route sufficient to provide a dose adequate to treat the vitamin D insufficiency.

Systems

In some aspects, the invention described herein is directed to systems (and computer readable media for causing computer systems) for obtaining data from at least one blood sample obtained from at least one subject, the system comprising 1) a determination module configured to receive the at least one blood sample and perform at least one analysis on the at least one blood sample to determine the level of bioavailable or free vitamin D in the sample; 2) a storage device configured to store data output from the determination module; and 3) a display module for displaying a content based in part on the data output from the determination module, wherein the content comprises a signal indicative of the level of bioavailable or free vitamin D.

Figure 6:
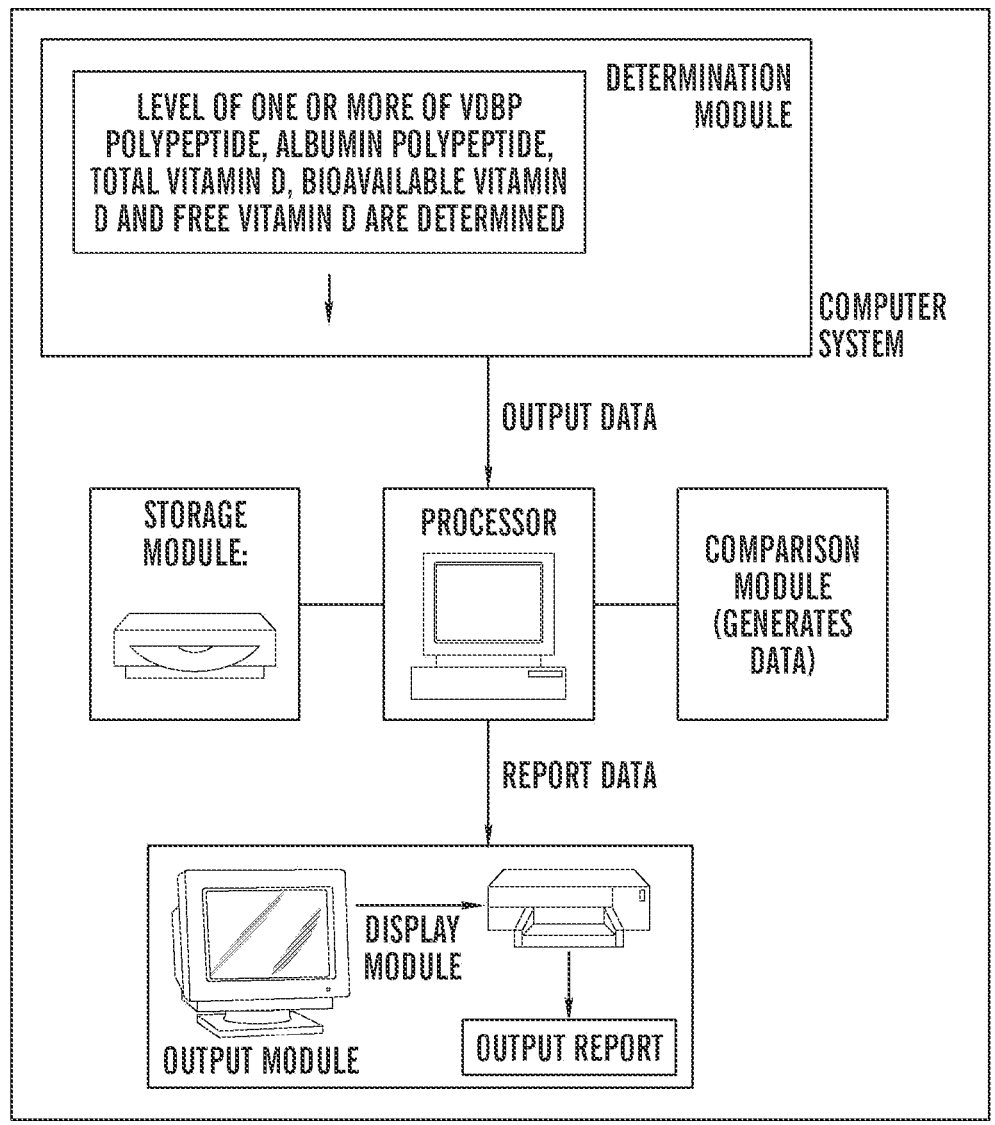
FIG. 6 is a diagram of an embodiment of a system for performing an assay for determining the level of bioavailable or free vitamin D in a blood sample obtained from a subject.

In one embodiment, provided herein is a system comprising: (a) at least one memory containing at least one computer program adapted to control the operation of the computer system to implement a method that includes (i) a determination module configured to receive the at least one blood sample and perform at least one analysis on the at least one blood sample to determine the level of bioavailable or free vitamin D in the sample (e.g. determining the level of one or more of VDBP polypeptide, albumin polypeptide, total vitamin D; bioavailable vitamin D; and free vitamin D); (ii) a storage module configured to store output data from the determination module; (iii) a computing module adapted to identify from the output data whether the level of VDBP polypeptide, albumin polypeptide, total vitamin D, bioavailable vitamin D or free vitamin D in a blood sample obtained from a subject indicates that the level of bioavailable or free vitamin D is lower than 25% of the mean value of bioavailable or free vitamin D in a population of healthy subjects and (iv) a display module for displaying a content based in part on the data output from the determination module, wherein the content comprises a signal indicative of the level of bioavailable or free vitamin D and (b) at least one processor for executing the computer program (see FIG. 6).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term a "computer system" may refer to a system having a computer, where the computer comprises a computer-readable medium embodying software to operate the computer.

The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a determination module, a storage module, a computing module, and a display module. The functional modules can be executed on one, or multiple, computers, or by using one, or multiple, computer networks. The determination module has computer executable instructions to provide e.g., levels of expression products etc in computer readable form.

The determination module can comprise any system for detecting a signal elicited from an assay to determine the level of any of a VDBP polypeptide, an albumin polypeptide, bioavailable vitamin D, free vitamin D, or total vitamin D as described above herein. In some embodiments, such systems can include an instrument, e.g., AU2700 (Beckman Coulter Brea, Calif.) as described herein for quantitative measurement of polypeptides. In another embodiment, the determination module can comprise multiple units for different functions, such as quantitative measurement of polypeptides (e.g. dye-based photometric assay or quantitative ELISA) and a mass spectroscopy system for the measurement of vitamin D. In one embodiment, the determination module can be configured to perform the methods described elsewhere herein, e.g. dye-based photometric assays for albumin, ELISA assays for VDBP polypeptide levels or mass spectroscopy to determine vitamin D levels. In some embodiments, such systems can include an instrument, e.g., the AU2700 (Beckman Coulter Brea, Calif.).

In some embodiments, the determination system or a further module can be configured to process whole blood samples, e.g. to separate serum from whole blood for use in the assays described herein.

The information determined in the determination system can be read by the storage module. As used herein the "storage module" is intended to include any suitable computing or processing apparatus or other device configured or adapted for storing data or information. Examples of electronic apparatus suitable for use with the present invention include standalone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of bioavailable or free vitamin D in healthy subjects and/or a population of healthy subjects.

Figure 7:
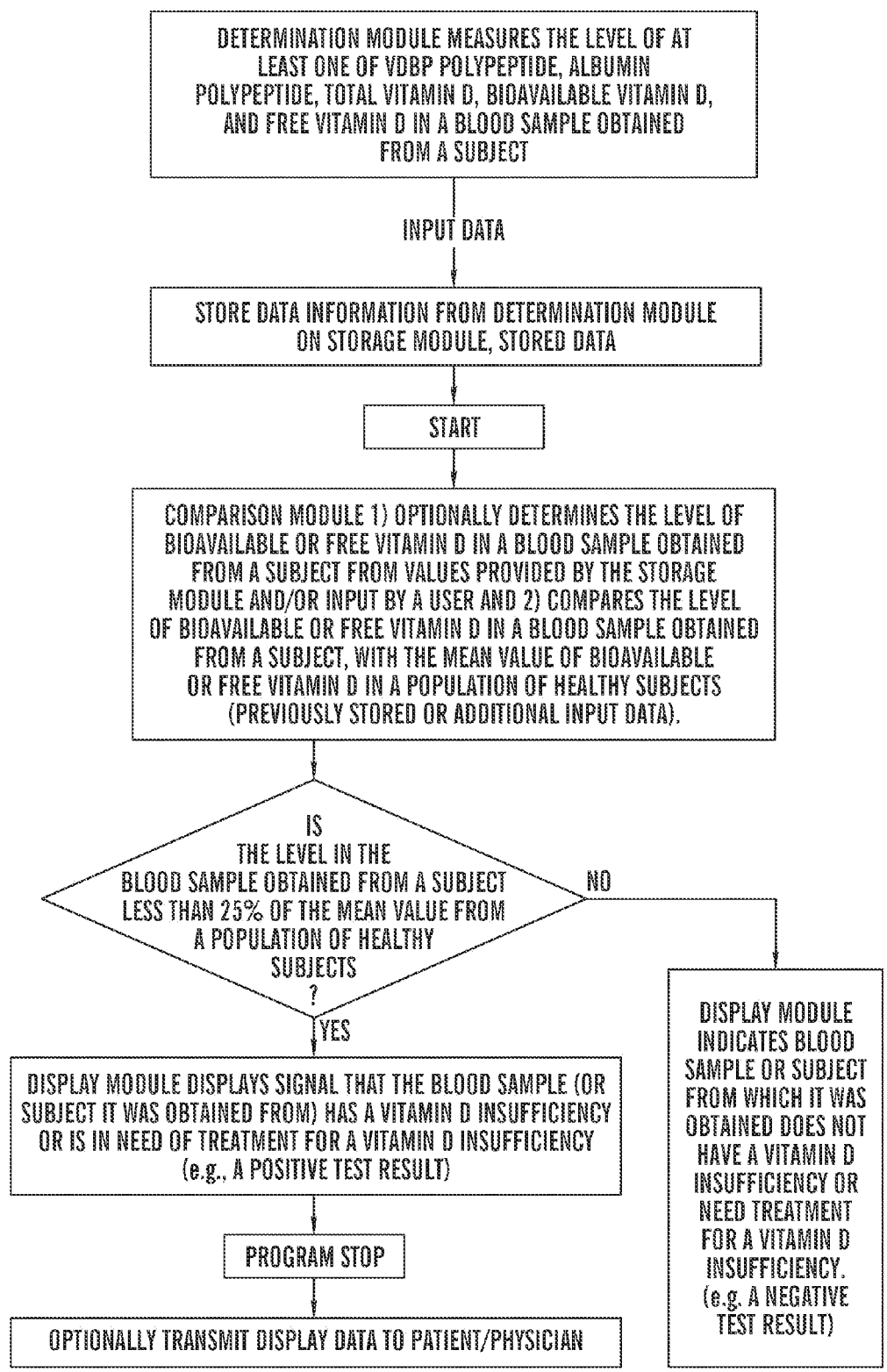
FIG. 7 is a diagram of an embodiment of a comparison module as described herein.

The "computing module" can use a variety of available software programs and formats for computing the level of bioavailable or free vitamin D. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of bioavailable or free vitamin D in a blood sample obtained from a subject as described herein with the mean value of bioavailable or free vitamin D in a population of healthy subjects (FIG. 7). By way of an example, when the value of bioavaible vitamin D in a blood sample obtained from a subject is measured, a comparison module can compare or match the output data—with the mean value of bioavailable vitamin D in a population of healthy subjects. In certain embodiments, the mean value of bioavailable or free vitamin D in a population of healthy subjects can be pre-stored in the storage module. During the comparison or matching process, the comparison module can determine whether the level of bioavailable or free vitamin D in the blood sample obtained from a subject is less than 25% of the mean value of bioavailable or free vitamin D in a population of healthy subjects. In various embodiments, the comparison module can be configured using existing commercially-available or freely-available software for comparison purpose, and may be optimized for particular data comparisons that are conducted.

Figure 8:
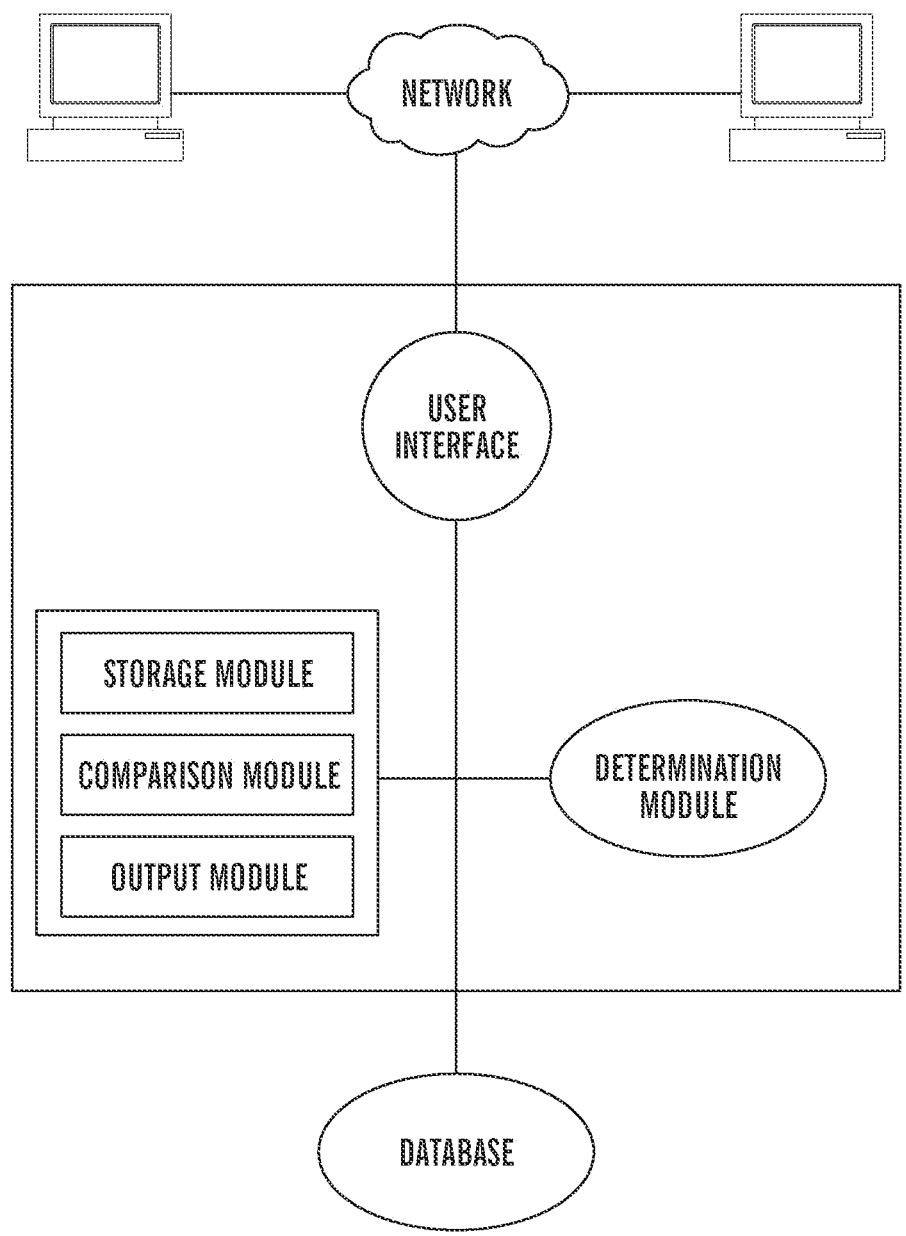
FIG. 8 is a diagram of an embodiment of an operating system and applications for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 8).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of bioavailable or free vitamin D in the blood sample obtained from a subject. In some embodiments, the content displayed on the display module can be the relative level of bioavailable or free vitamin D in the blood sample obtained from a subject as compared to the mean level of bioavailable or free vitamin D in a population of healthy subjects. In some embodiments, the content displayed on the display module can indicate whether the level of bioavailable or free vitamin D in the blood sample obtained from a subject is less or more than 25% of the mean value of bioavailable or free vitamin D in a population of healthy subjects. In some embodiments, the content displayed on the display module can indicate whether the subject has an insufficient level of vitamin D. In some embodiments, the content displayed on the display module can indicate whether the subject is in need of a treatment for vitamin D insufficieny. In some embodiments, the content displayed on the display module can indicate whether the subject has an increased risk or likelihood of having or developing a vitamin D-associated disease. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having a vitamin D-associated disease. In some embodiments, the content displayed on the display module can be single word or phrases to qualitatively indicate a risk or probability. For example, a word "unlikely" can be used to indicate a lower risk for having or developing a vitamin D-associated disease, while "likely" can be used to indicate a high risk for having or developing a vitamin D-associated disease.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

In some embodiments, the system further comprises a means of inputting a value for the level of one or more of VDBP polypeptide, albumin polypeptide, and total vitamin D determined to be in a blood sample obtained from a subject. By way of non-limiting example, the level of albumin polypeptide can be determined by the determination module of the system while the level of VDBP polypeptide is determined by an ELISA assay performed separately from the system described herein. When the level of VDBP polypeptide is determined, the value for this level can be entered into the computing module of the system and used to determine the level of bioavailable or free vitamin D in the blood sample obtained from the subject. In some embodiments, the inputting means comprises a keyboard or touchscreen which allows a user to type a value which is accepted by the computing module.

Systems and computer readable media described herein are merely illustrative embodiments of the invention for determining the level of bioavailable or free vitamin D in a blood sample obtained from a subject, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments can perform functions in a different order, or functions can be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments can also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

Some embodiments of the present invention can be defined as any of the following numbered paragraphs:

I. An assay comprising:
analyzing a blood sample obtained from a subject to determine a level of VDBP (vitamin D binding protein) polypeptide, albumin polypeptide and total vitamin D;
wherein a level of bioavailable vitamin D is:

$$=(K_{alb}*[Alb]+1)*[\text{Free Vitamin }D]$$

and wherein a level of free vitamin D is:

$$=\{-\{K_{DBP}\cdot[\text{Total }DBP]-K_{DBP}\cdot[\text{Total Vitamin }D]+K_{alb}\cdot[Alb]+1\}+\sqrt{\{(K_{DBP}\cdot[\text{Total }DBP]-K_{DBP}\cdot[\text{Total Vitamin }D]+K_{alb}\cdot[Alb]+1)^2+4\cdot(K_{DBP}\cdot K_{alb}\cdot[Alb]+K_{DBP})\cdot([\text{Total Vitamin }D])\}\}\div(2\cdot\{K_{DBP}\cdot K_{alb}\cdot[Alb]+K_{DBP}\}).$$

II. The assay of paragraph I, wherein a level of bioavailable vitamin D lower than 25% of the mean value of bioavailable vitamin D in a population of healthy subjects indicates that the subject has a vitamin D insufficiency.

III. The assay of any of paragraphs I-II, wherein the vitamin D is selected from the group consisting of: 25-hydroxyvitamin D and 1,25-dihydroxyvitamin D.

IV. The assay of any of paragraphs I-III, wherein the determining of the level of VDBP polypeptide or albumin polypeptide comprises use of a method selected from the group consisting of:
enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

V. The assay of any of paragraphs I-IV, wherein the determining of the level of total vitamin D comprises the use of a method selected from the group consisting of:
radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

VI. The assay of any of paragraphs I-V, wherein an insufficiency of vitamin D indicates an increased risk of a condition selected from the group consisting of:
decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy; asthama; multiple sclerosis; muscle weakness; rheumatoid arthritis and diabetes.

VII. The assay of any of paragraphs I-VI, further comprising the step of administering a vitamin D insufficiency treatment to a subject who is determined to have a vitamin D insufficiency.

VIII. The assay of any of paragraphs I-VII, wherein the treatment comprises administering a compound selected from the group consisting of:
calcitriol; dihydrotachysterol; doxercalciferol; paricalcitol; cholecalciferol and ergocalciferol.

IX. An assay comprising:
analyzing a blood sample obtained from a subject to determine a level of VDBP polypeptide, albumin polypeptide and total vitamin D;
wherein a level of free vitamin D is:

$$=\{-\{K_{DBP}\cdot[\text{Total }DBP]-K_{DBP}\cdot[\text{Total Vitamin }D]+K_{alb}\cdot[Alb]+1\}+\sqrt{\{(K_{DBP}\cdot[\text{Total }DBP]-K_{DBP}\cdot[\text{Total Vitamin }D]+K_{alb}\cdot[Alb]+1)^2+4\cdot(K_{DBP}\cdot K_{alb}\cdot[Alb]+K_{DBP})\cdot([\text{Total Vitamin }D])\}\}\div(2\cdot\{K_{DBP}\cdot K_{alb}\cdot[Alb]+K_{DBP}\}).$$

X. The assay of paragraph IX, wherein a level of free vitamin D lower than 25% of the mean value of free vitamin D in a population of healthy subjects indicates that the subject has a vitamin D insufficiency.

XI. The assay of any of paragraphs IX-X, wherein the vitamin D is selected from the group consisting of: 25-hydroxyvitamin D and 1,25-dihydroxyvitamin D.

XII. The assay of any of paragraphs IX-XI, wherein the determining of the level of VDBP polypeptide or albumin polypeptide comprises the use of a method selected from the group consisting of:
enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

XIII. The assay of any of paragraphs IX-XII, wherein the determining of the level of total vitamin D comprises the use of a method selected from the group consisting of:
radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

XIV. The assay of any of paragraphs IX-XIII, wherein an insufficiency of vitamin D indicates an increased risk of a condition selected from the group consisting of:
decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

XV. The assay of any of paragraphs IX-XIV, further comprising the step of administering a vitamin D insufficiency treatment to a subject who is determined to have a vitamin D insufficiency.

XVI. The assay of any of paragraphs IX-XV, wherein the treatment comprises administering a compound selected from the group consisting of:
calcitriol; dihydrotachysterol; doxercalciferol; paricalcitol; cholecalciferol and ergocalciferol.

XVII. A method for treating a vitamin D insufficiency in a subject comprising detecting a level of VDBP polypeptide, albumin polypeptide and total vitamin D in a blood sample obtained from a subject;
wherein a level of bioavailable vitamin D is:

$$=(K_{alb}*[Alb]+1)*[Free\ Vitamin\ D]$$

and wherein a level of free vitamin D is:

$$=\{-\{K_{DBP}\cdot[Total\ DBP]-K_{DBP}\cdot[Total\ Vitamin\ D]+K_{alb}\cdot[Alb]+1\}+\sqrt{\{(K_{DBP}\cdot[Total\ DBP]-K_{DBP}\cdot[Total\ Vitamin\ D]+K_{alb}\cdot[Alb]+1)^2+4\cdot(K_{DBP}\cdot K_{alb}\cdot[Alb]+K_{DBP})\cdot([Total\ Vitamin\ D])\}\}\div(2\cdot\{K_{DBP}\cdot K_{alb}\cdot[Alb]+K_{DBP}\})$$

and administering a treatment for vitamin D insufficiency to the subject if the level of bioavailable vitamin D is less than 25% of the mean value of bioavailable vitamin D in a population of healthy subjects.

XVIII. A method for treating a vitamin D insufficiency in a subject comprising detecting a level of VDBP polypeptide, albumin polypeptide and total vitamin D in a blood sample obtained from a subject;
wherein a level of free vitamin D is:

$$=\{-\{K_{DBP}\cdot[Total\ DBP]-K_{DBP}\cdot[Total\ Vitamin\ D]+K_{alb}\cdot[Alb]+1\}+\sqrt{\{(K_{DBP}\cdot[Total\ DBP]-K_{DBP}\cdot[Total\ Vitamin\ D]+K_{alb}\cdot[Alb]+1)^2+4\cdot(K_{DBP}\cdot K_{alb}\cdot[Alb]+K_{DBP})\cdot([Total\ Vitamin\ D])\}\}\div(2\cdot\{K_{DBP}\cdot K_{alb}\cdot[Alb]+K_{DBP}\})$$

and administering a treatment for vitamin D insufficiency to the subject if the level of free vitamin D is less than 25% of the mean value of free vitamin D in a population of healthy subjects.

XIX. A system for obtaining data from at least one blood sample obtained from at least one subject, the system comprising:
a determination module configured to receive the at least one blood sample and perform at least one analysis on the at least one blood sample to determine a level of bioavailable or free vitamin D in the sample;
a storage device configured to store data output from said determination module; and
a display module for displaying a content based in part on the data output from said determination module, wherein the content comprises a signal indicative of the level of bioavailable or free vitamin D.

XX. The system of paragraph XIX, wherein the system further comprises a means of inputting a value for the level of one or more of VDBP polypeptide, albumin polypeptide, and total vitamin D determined to be in a test sample.

XXI. The system of any of paragraphs XIX-XX, wherein the content displayed on said display module further comprises a signal indicative of the subject having an increased likelihood of a vitamin D insufficiency if the level of bioavailable or free vitamin D is determined to be lower than 25% of the mean value of bioavailable vitamin D in a population of healthy subjects.

XXII. The system of any of paragraphs XIX-XXI, wherein the content displayed on said display module further comprises a signal indicative of the subject being recommended to receive a treatment for vitamin D insufficiency.

XXIII. A method of treatment comprising:
analyzing a blood sample obtained from a subject to determine a level of free or bioavailable vitamin D;
wherein a level of free or bioavailable vitamin D lower than 25% of the mean value of free or bioavailable vitamin D in a population of healthy subjects indicates that the subject has a vitamin D insufficiency; and
administering a vitamin D insufficiency treatment to a subject who is determined to have a vitamin D insufficiency.

XXIV. The method of paragraph XXIII, wherein the vitamin D is selected from the group consisting of:
25-hydroxyvitamin D and 1,25-dihydroxyvitamin D.

XXV. The method of any of paragraphs XXIII-XXIV, wherein the determining of the level of free or bioavailable vitamin D comprises use of a method selected from the group consisting of:
immunoassay; two-step immunoassay with antibody capture; one-step immunoassay with immobilized antibody and competitive detection; one-step immunoassay with immobilized competitior and labeled antibody; fluorescence polarization immunoassay; differential precipitation (immunoprecipitation, affinity precipitation); immunodepletion; and affinity binding chromatography;
and a method selected from the group consisting of:
radioimmunoassay; chemiluminescent immunosorbent assay; electrochemiluminescent immunosorbent assay; fluorescent immunosorbent assay; dye linked immunosorbent assay; liquid chromatography tandem mass spectroscopy and high-pressure liquid chromatography.

XXVI. The method of any of paragraphs XXIII-XXIV, wherein an insufficiency of vitamin D indicates an increased risk of a condition selected from the group consisting of:
decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

XXVII. The method of any of paragraphs XXIII-XXVI, wherein the treatment comprises administering a compound selected from the group consisting of:
calcitriol; dihydrotachysterol; doxercalciferol; paricalcitol; cholecalciferol and ergocalciferol.

XXVIII. An assay comprising:
analyzing a blood sample obtained from a subject to determine a level of free vitamin D and albumin polypeptide;

wherein a level of bioavailable vitamin D is:

$=(K_{alb}*[Alb]+1)*[\text{Free Vitamin }D]$

XXIX. The assay of paragraph XXVIII, wherein a level of bioavailable vitamin D lower than 25% of the mean value of bioavailable vitamin D in a population of healthy subjects indicates that the subject has a vitamin D insufficiency.

XXX. The assay of any of paragraphs XXVIII-XXIX, wherein the vitamin D is selected from the group consisting of:
25-hydroxyvitamin D and 1,25-dihydroxyvitamin D.

XXXI. The assay of any of paragraphs XXVIII-XXX, wherein the determining of the level of albumin polypeptide comprises use of a method selected from the group consisting of:
enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

XXXII. The assay of any of paragraphs XXVIII-XXXI, wherein the determining of the level of free vitamin D comprises the use of a method selected from the group consisting of:
immunoassay; two-step immunoassay with antibody capture; one-step immunoassay with immobilized antibody and competitive detection; one-step immunoassay with immobilized competitior and labeled antibody; fluorescence polarization immunoassay; differential precipitation (immunoprecipitation, affinity precipitation); immunodepletion; and affinity binding chromatography;
and a method selected from the group consisting of:
radioimmunoassay; chemiluminescent immunosorbent assay; electrochemiluminescent immunosorbent assay; fluorescent immunosorbent assay; liquid chromatography tandem mass spectroscopy and high-pressure liquid chromatography.

XXXIII. The assay of any of paragraphs XXVIII-XXXII, wherein an insufficiency of vitamin D indicates an increased risk of a condition selected from the group consisting of:
decreased bone density; decreased bone mineral density; bone fractures; bone resorption; rickets; osteitis fibrosa cystica; fibrogenesis imperfect ossium; osteosclerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthama; multiple sclerosis; muscle weakness; rheumatoid arthritis and diabetes.

XXXIV. The assay of any of paragraphs XXVIII-XXXIII, further comprising the step of administering a vitamin D insufficiency treatment to a subject who is determined to have a vitamin D insufficiency.

XXXV. The assay of any of paragraphs XXVIII-XXXIV, wherein the treatment comprises administering a compound selected from the group consisting of: calcitriol; dihydrotachysterol; doxercalciferol; paricalcitol; cholecalciferol and ergocalciferol.

EXAMPLES

Example 1

Bioavailable Vitamin D and Bone Mineral Density

Studies examining the relationship between total circulating 25-hydroxyvitamin D (25(OH)D) levels and bone mineral density (BMD) have yielded mixed results. Vitamin D binding protein (DBP), the major carrier protein for 25(OH)D, may alter the biologic activity of circulating vitamin D. Demonstrated herein is a test of the hypothesis that free and bioavailable 25(OH)D, calculated from total 25(OH)D, DBP and serum albumin levels, is more strongly associated with BMD than levels of total 25(OH)D.

Total 25(OH)D, DBP, and serum albumin levels were measured in 49 healthy young adults enrolled in the Metabolic Abnormalities in College-Aged Students (MACS) study. Lumbar spine BMD was measured in all subjects using dual X-ray absorptiometry. Clinical, diet, and laboratory information was also gathered at this time. Free and bioavailable (free+albumin bound) 25(OH)D was determined and their associations with BMD were examined.

BMD was not associated with total 25(OH)D levels (r=0.172 p=0.236). In contrast, free and bioavailable 25(OH)D levels were positively correlated with BMD (r=0.413 p=0.003 for free, r=0.441 p=0.002 for bioavailable). Bioavailable 25(OH)D levels remained independently associated with BMD in multivariate regression models adjusting for age, sex, body mass index, and race (p=0.03). Free and bioavailable 25(OH)D are more strongly correlated with BMD than total 25(OH)D. These findings have important implications for vitamin D supplementation in vitamin D deficient states.

Introduction

Vitamin D insufficiency is associated with decreased calcium absorption and elevated levels of parathyroid hormone (PTH), (1) which may lead to excessive bone resorption. (2) In some observational studies, higher levels of 25-hydroxyvitamin D (25(OH)D) have been linked to increased bone mineral density (BMD) and decreased risk of fracture. (3-7) Additionally, several randomized control trials suggest that vitamin D supplementation reduces the risk of fracture and increases BMD. (8-14) However, not all observational studies have confirmed the relationship between 25-hydroxyvitamin D (25(OH)D) and BMD, especially in younger populations or racial minorities. (15-19) Moreover, in several randomized trials, the effect of vitamin D supplementation on BMD or fracture risk has been modest, (8) absent, (20-22) or reversed. (23)

The free hormone hypothesis postulates that only hormones liberated from binding proteins enter cells and produce biological action. (24) 25(OH)D and 1,25-dihydroxyvitamin D (1,25(OH)2D) circulate bound to vitamin D binding protein (85-90%) and albumin (10-15%) with less than 1% of circulating hormone in its free form. (25) In mice, vitamin D binding protein (DBP) prolongs the serum half life of 25(OH)D and protects against vitamin D insufficiency by serving as a vitamin D reservoir. (26) However, DBP also limits the biological activity of injected 1,2 (OH)2D in mice (26) and inhibits the action of vitamin D on monocytes and keratinocytes in vitro. (27-28) The significance of circulating DBP levels with regards to vitamin D's biological action in humans is unclear.

The free fraction of 25(OH)D and the binding affinity constants for 25(OH)D's interaction with DBP and albumin have previously been measured. (29) Formulae for the calculation of free 25(OH)D levels based on serum concentrations of total 25(OH)D, DBP, albumin, and have been developed based on this data. Measured and calculated values of free 25(OH)D are highly correlated. (29)

Materials and Methods

Subject Recruitment.

A cross-sectional study was conducted in a subset of healthy young adults enrolled in the Metabolic Abnormalities in College Students study (MACS), a study designed to evaluate the prevalence of metabolic abnormalities in university students. (30) Subjects were healthy 18-31 year old male and female students from private universities in the Boston area. 170 subjects were recruited through flyers posted throughout the Massachusetts Institute of Technology (MIT) campus and through targeted emails to random members of the student population. All subjects provided written informed consent. The study was approved by the MIT Committee on the Use of Humans as Experimental Subjects. 49 subjects had sufficient sample for inclusion in this analysis and their characteristics are presented in Table 1.

Study Visit.

Subjects were instructed to fast for 12 hours prior to admission to the MIT Clinical Research Center as outpatients and underwent a baseline evaluation including a blood sample collection and various physiologic measurements. Structured interviews were conducted by study nurses to collect standard clinical information, minutes of exercise per week (in 30 minute increments), and medication/supplement use. Height was measured using a standing stadiometer (Holton Ltd, Crymych, Dyfed, UK). Weight was measured using a calibrated scale (SECA, Hanover, Md., USA). Body mass index (BMI) was calculated as weight(kg)/[height(m)]$^2$.

Dietary Information.

Subjects completed a written food record 1 week prior to the day of study, recording 4 full days of food intake, including one weekend day. During the study visit to the MIT CRC, a registered dietitian reviewed the food record with the subject to clarify the quantities and sources of food consumed. Dietary intake data were then analyzed using Nutrition Data System for Research software version 2006/2007 (Nutrition Coordinating Center, University of Minnesota, Minneapolis, Minn.).

Bone Density Measurement.

Subjects underwent total-body dual-energy x-ray absorptiometry (DEXA) (Hologic QDR-4500A; Hologic, Waltham, Mass., USA) to determine total and regional BMD. (31) Hologic phantoms were used to calibrate the instrument. Lumbar spine BMD was used in this study as the measure of BMD. Lumbar spine BMD is a preferred site for the diagnosis of osteoporosis and the prediction of fracture. No hip BMD measurements were available. (32-33)

Biochemical Analysis.

Baseline blood samples were frozen at −80° C. and stored for later analysis. 25(OH)D, serum calcium, albumin, and levels of PTH were measured in the Massachusetts General Hospital (MGH) clinical laboratories. 25(OH)D2 and 25(OH)D3 levels were measured by liquid chromatography tandem mass spectrometry (LC-MS), with interassay CV's of 9.1% for 25(OH)D$_2$ and 8.6% for 25(OH)D$_3$. Total 25(OH)D level was calculated as the sum of 25(OH)D$_2$ level and 25(OH)D$_3$ level. Intact PTH was measured by electrochemiluminescense immunoassay on the Cobas E160 automated analyzer (Roche Diagnostics, Indianapolis, Ind.). Interassay CV for intact PTH measurement was 4.2%. Calcium and albumin levels were measured by dye-based photometric assays on an automated analyzer. DBP was measured in duplicate by commercial enzyme linked immunosorbent assay (ELISA) (R&D Systems, Minneapolis, Minn., Catalog Number DVDBP0) according to the manufacturer's instructions. The assay was conducted after diluting serum samples 1 to 2,000 in Calibrator Diluent RD6-11 (R&D Systems Part Number 895489). Inter-assay CV was 8.5% at a concentration of 40 ug/ml. The assay recovered between 93 and 110% of a 100-200 ug/mL dose of exogenous vitamin D binding protein added to human serum samples containing between 25-200 ug/mL of endogenous vitamin D binding protein. The manufacturer reports no significant cross-reactivity with human albumin, vitamin D3, or alpha-fetoprotein. In a subset of patients in whom adequate serum was available (N=45), total 1,25(OH)$_2$D was measured by LC-MS/MS in the Mayo Clinic Medical Laboratories (Rochester, Minn., USA).

Calculation of Unbound 25(OH)D.

Free levels of 25(OH)D were calculated using two methods. Both methods used the binding affinity constants between albumin and DBP and 25(OH)D measured in a previous study which used centrifugal ultrafiltration to determine the free fraction of 25(OH)D. (29)

Method 1:

Free levels of 25(OH)D were calculated using the following equation:

$$\text{Free } 25(OH)D = \frac{\text{Total } 25(OH)D}{1 + (6 \times 10^5 \times \text{Albumin}) + (7 \times 10^8 \times DBP)}. \quad (29)$$

The reported correlation coefficient between calculated free 25(OH)D using this equation and measured free 25(OH)D by centrifugal ultrafiltration is 0.925. (29) Free 1,25(OH)D levels were also calculated using this method. (25)

Method 2:

Free, bioavailable, and DBP-bound 25(OH)D were calculated using equations described in Appendix 1 of this Example below. These methods define bioavailable hormone as the fraction that is both free and albumin-bound, i.e. the fraction not bound to circulating binding proteins such as DBP.

Both calculation methods used the same affinity binding constants. Applied to the same measurements of total 25(OH)D, DBP, and albumin, they produce calculated free 25(OH)D values that are highly correlated (Spearman r=1), however the equations produce values that are an average of 1.4% higher (data not shown). Because the equations also provide for separate calculation of free, bioavailable, and DBP-bound 25(OH)D, Method 2 procedures were used for subsequent analyses of 25(OH)D levels.

Statistical Analysis.

Subject characteristics are reported as mean±SD unless otherwise noted. Non-normal variables including 25(OH)D levels, DBP levels, BMD, and dietary calcium intake levels showed skewed distributions and were natural log transformed in order to meet the assumptions of parametric statistical techniques. Exercise amount was dichotomized at 120 minutes per week. Pearson's correlation coefficients were calculated to assess the relationships between 25(OH)D levels, BMD, and other continuous variables. Independent samples t-tests were used to compare 25(OH)D levels, DBP levels, and BMD among subgroups defined by race, sex, exercise amount, and oral contraceptive use. Linear regression analysis was used to test for the presence of an independent relationship between 25(OH)D levels, DBP, and BMD after adjustment for factors previously reported to be associated with bone density including age, sex, BMI and race. (5, 8, 12, 35-36) All analyses were conducted using STATA Statistical Software (College Station, Tex.) version 11. Two sided p-values <0.05 were considered statistically significant.

Results

Subject characteristics are shown in Table 1. There was wide variation in levels of DBP, with concentrations ranging from 0.66 to 11.2 umol/L. Accordingly, calculated free and bioavailable 25(OH)D levels ranged widely (Table 2). Total 25-hydroxyvitamin D levels were positively correlated with DBP levels (r=0.335, p=0.019).

Total 25(OH)D levels were not correlated with BMD (r=0.172 p=0.236, FIG. 1). Similarly, levels of DBP-bound 25(OH)D were not correlated with BMD (r=0.072, p=0.626). In contrast, free and bioavailable 25(OH)D levels were both strongly correlated with BMD (r=0.413 p=0.003 for free and r=0.441 p=0.002 for bioavailable, FIG. 1). Bioavailable and free 25(OH)D levels were highly correlated with each other (r=0.985, p<0.001), but bioavailable 25(OH)D made up a larger portion of the total 25(OH)D with approximately 350-fold higher concentrations of bioavailable 25(OH)D compared to free 25(OH)D. (Table 2) Total and calculated free levels of $1,25(OH)_2D$ were not correlated with BMD (p>0.05). Total levels of $1,25(OH)_2D$ were not associated with free or bioavailable 25(OH)D levels (p>0.05), nor was sex-adjusted alkaline phosphatase associated with total, free, or bioavailable 25(OH) D (p>0.05) Neither total nor bioavailable 25(OH)D levels were correlated with serum calcium or PTH levels (p>0.05). Of note, PTH levels fell between 15 and 51 ng/L (all within the normal range) and were not associated with BMD (r=-0.024, p=0.869).

Both total 25(OH)D and DBP levels were inversely associated with BMI (r=-0.300, p=0.036 for total and r=-0.542, p<0.001 for DBP). Bioavailable 25(OH)D was positively correlated with BMI (r=0.302, p=0.035). However, in this population, BMI was not correlated with BMD (r=0.160, p=0.271). Dietary calcium intake was correlated with total 25(OH)D (r=0.339, p=0.021), but was not correlated with DBP, bioavailable 25(OH)D, or BMD (p>0.05). Levels of total and bioavailable 25(OH)D, DBP and BMD among selected subgroups are shown in Table 3. Females had greater average total 25(OH)D levels than males, but average DBP levels, bioavailable 25(OH)D levels and BMD did not differ between males and females. Females reporting use of oral contraceptive pills (OCP) had higher average total 25(OH)D compared with females who did not report OCP use, but average DBP and bioavailable 25(OH)D levels were not significantly different based on OCP use. Subjects with BMI greater than or equal to 25 kg/m² (overweight subjects) had lower DBP levels than subjects with BMI less than 25 kg/m² (normal weight subjects). Subjects who reported exercising 120 minutes a week or more had higher average total 25(OH)D levels than subjects who did not, but no significant difference was found in average DBP levels, bioavailable 25(OH)D levels, and BMD. Average DBP levels in non-white subjects were lower than in white subjects (Table 3).

In multivariate models adjusting for age, sex, BMI and race, bioavailable 25(OH)D remained independently associated with BMD(p=0.03, Table 4). Bioavailable 25(OH)D was the only significant predictor of BMD in multivariate models. As the level of calculated bioavailable 25(OH)D is dependent on the concentrations of total 25(OH)D, albumin, and DBP, it was separately assessed whether albumin or DBP was associated with BMD. DBP level was inversely correlated with BMD (r=-0.296, p=0.039) while serum albumin showed no association with BMD (r=0.156, p=0.285). In a multivariate linear regression model, total 25(OH)D became a significant predictor of BMD only after adjustment for DBP level (B=0.089, p=0.040). Albumin was not associated with BMD in a multivariate model including DBP and total 25(OH)D (p=0.150).

Discussion

In light of conflicting reports concerning the relationship between circulating levels of 25(OH)D and BMD, serum levels of total 25(OH)D, DBP, and albumin were measured in a group of young healthy adults and assessed relationships between free 25(OH)D, bioavailable 25(OH)D, total 25(OH)D and BMD. Without meaning to be limiting, the results described herein are consistent with the free hormone hypothesis and suggest that circulating DBP is an inhibitor of the biological action of vitamin D in humans. The similar associations between free and bioavailable vitamin levels and BMD imply that, unlike binding to DBP, binding to albumin does not inhibit the action of 25(OH)D. These results are consistent with prior basic and clinical studies on DBP.

The results described herein support the hypothesis that DBP behaves similarly to other serum hormone carrier proteins and have broad clinical applications. Like thyroid hormone binding globulin and sex hormone binding globulin, DBP may act as a serum carrier and reservoir, prolonging the circulating half-life of vitamin D, while at the same time regulating its immediate bioavailability to target tissues. (24). In contrast to the megalin-mediated endocytosis described in renal tubular cells, our results imply that 25(OH)D gains access to some target cells by diffusion across cell membranes, similar to these other steroid hormones. (24) Thus hormonal activity and sufficiency may be reflected by the amounts of bioavailable vitamin, not by total serum levels. Currently, clinical testing for vitamin D insufficiency is based upon measurement of total serum concentrations of 25(OH) D. (2) Yet, the data described herein suggests that concentrations of total serum vitamin D may not be the best measure of vitamin D sufficiency. For example, patients with high levels of DBP may appear to be 25(OH)D sufficient, but may actually be deficient in bioavailable vitamin. Conversely, in patients with low levels of DBP, total 25(OH)D will be low, but these patients may actually have sufficient bioavailable vitamin. The maintenance of bioavailable 25(OH)D levels in obese and non-white subjects, despite lower levels of total 25(OH)D raise the possibility that variation in circulating DBP explains the apparent paradox of low 25(OH)D levels and higher BMD in black and overweight patients seen in several previous studies, (5, 15-16, 35, 44-45).

The results described herein contrast with results of some prior studies linking total 25(OH)D levels to BMD, but are consistent with other studies which failed to find such a relationship. (4-5, 15-18) In these prior studies, DBP levels were not measured. Of note, total 25(OH)D and free/bioavailable 25(OH)D levels are associated, and it is possible that a larger sample size would have enabled detection of a weak relationship between total 25(OH)D and BMD. Prior studies that found this relationship generally had sample sizes greater than 200 and when correlation coefficients between 25(OH)D and BMD were reported, they were less than 0.2. (4-5, 16, 19)

A relationship between $1,25(OH)_2D$ levels and BMD was not found. While $1,25(OH)_2D$ is thought to be the active form of vitamin D, many tissues express 1-α hydroxylase, and may be able to convert circulating 25(OH)D to its active form locally. (46) Circulating 25(OH)D levels are generally considered to better reflect overall vitamin D stores. (2) The results describe herein are in agreement with this, suggesting that total circulating total or free $1,25(OH)_2D$ levels are not good measures of vitamin D activity. This is analogous to the accepted model for the measurement of thyroid hormone action, where free T4 levels are a better measure of thyroid hormone action than circulating free T3 levels, even though T3 is the active form of the hormone. (47)

The use of standardized immunoassays for vitamin D, DBP, and albumin combined with standard calculation methods would allow the approach described herein to be adopted with more confidence by other clinical laboratories.

A wide distribution of DBP levels among our subjects and observed that DBP was negatively associated with both high BMI and black race, both of which have been associated with low 25(OH)D levels. Without wishing to be limiting, one potential explanation is that 25(OH)D might itself regulate the production of DBP. Lowering DBP levels would allow a higher fraction of DBP to be bioavailable in situations where total levels are low. Other possible explanations for the observed associations between race, BMI, and DBP levels include genetic factors and uptake of circulating DBP by adipose tissue.

Described herein is evidence that DBP modifies the relationship between 25(OH)D and BMD in humans. Our data suggest that bioavailable 25(OH)D levels are a better of measure of vitamin D activity than total 25(OH)D levels, at minimum, with respect to bone metabolism. It is therefore possible that by using total 25(OH)D levels as a measure of vitamin D sufficiency, individuals may be misclassified as vitamin D sufficient or insufficient. This may explain conflicting results of prior studies of the relationship between serum 25(OH)D concentrations and BMD. Determining which individuals have a true deficit in vitamin D may allow future vitamin D supplementation interventions to be targeted to those individuals most likely to benefit. Additionally, use of bioavailable 25(OH)D levels may further elucidate the nature of the relationship between vitamin D and a wide range of outcomes including fracture, (7) infection, (49) cancer, (50) and cardiovascular disease. (51)

Appendix. Derivation of Calculated Free and Bioavailable 25-Hydroxyvitamin D

DEFINITIONS

D=25-hydroxyvitamin D (calcidiol), sum of both D2 and D3
Alb=albumin
DBP=Vitamin D binding protein, also known as Group-specific component or Gc
$[D_{Alb}]$=concentration of albumin-bound vitamin D
$[D_{DBP}]$=concentration of DBP-bound vitamin D
[D]=concentration of free (unbound) D
[Total]=concentration of Total 25OH-D=$[D_{DBP}]+[D_{Alb}]+[D]$
[Bio]=concentration of Bioavailable D (Bioavailable=sum of free and albumin-bound vitamin)=$[D]+[D_{Alb}]$
$K_{alb}$=affinity constant between vitamin D and albumin=$6\times 10^5$ $M^{-1}$
$K_{DBP}$=affinity constant between vitamin D and DBP=$0.7\times 10^9$ $M^{-1}$ Equations
Total 25(OH)-Vitamin D

[Total]=concentration of 25(OH)-Vitamin D in g/mol÷400.5 g/mole

Given that $[Total]=[D]+[D_{Alb}]+[D_{DBP}]$ thus $[D_{DBP}]=[Total]-[D_{Alb}]-[D]$ (Eq. 1)

Albumin

[Alb]=serum albumin concentration in g/L÷66,430 g/mole $[D]+[Alb] \leftrightarrow [D_{Alb}]$ Albumin association constant $K_{alb}=[D_{Alb}]\div([D]\cdot[Alb])$ Thus $[D_{Alb}]=K_{alb}\cdot[Alb]\cdot[D]$ (Eq. 2)

(NB: [Alb] in this example denotes the concentration of free non-vitamin bound albumin. However, given the low affinity between albumin and Vit. D, the concentrations of total albumin and unbound albumin are effectively equivalent ([Total Albumin]≈[Alb]). As a result, [Alb] may be estimated accurately by measurements of total serum albumin.)

DBP

[Total DBP]=concentration of serum DBP in g/L 58,000 g/mole

[DBP]=free unbound DBP and $[D_{DBP}]$=vitamin-bound DBP

Given that $[D]+[DBP] \leftrightarrow [D_{DBP}]$

And DBP association constant $K_{DBP}=[D_{DBP}]\div([DBP]\cdot[D])$

Thus $[D]=[D_{DBP}]\div K_{DBP}\div[DBP]$ (Eq. 3)

Since [Total DBP]=sum of bound and unbound DBP=$[DBP]+[D_{DBP}]$

Therefore $[DBP]=[Total\ DBP]-[D_{DBP}]$ (Eq. 4)

Solving for Free 25(OH)-Vitamin D
From Eqs. 3 and 4 we see that:

$[D]=[D_{DBP}]\div K_{DBP}\div([Total\ DBP]-[D_{DBP}])$ (Eq. 5)

If we substitute Eq. 1 into Eq. 2, we find that:

$[D_{DBP}]=[Total]-(K_{alb}\cdot[Alb]+1)\cdot[D]$ (Eq. 6)

Substituting Eq. 6 into Eq. 5 produces the following:

$[D]=\{[Total]-(K_{alb}\cdot[Alb]+1)\cdot[D]\}\div K_{DBP}\div([Total\ DBP]-\{[Total]-(K_{alb}\cdot[Alb]+1)\cdot[D]\})$ The equation is now limited to known constants ($K_{DBP}$ and $K_{alb}$), measured values ([Total DBP], [Alb], and [Total]) and the dependent variable for free vitamin D [D]. After propagating products and several rearrangements we can further simplify this to fit the form of a second-degree polynomial:

$ax^2+bx+c=0$

Where x=[D]=the concentration of free 25(OH)-Vitamin D
$a=K_{DBP}\cdot K_{alb}\cdot[Alb]+K_{DBP}$
$b=K_{DBP}\cdot[Total\ DBP]-K_{DBP}\cdot[Total]+K_{alb}\cdot[Alb]+1$
c=−[Total]
This polynomial may be solved for [D] using the quadratic equation:

$[D]=[-b+\sqrt{b2-4ac}]\div 2a$

After solving for free 25(OH)-vitamin D, we may then use Eq. 2 to calculate the concentration of bioavailable (non-DBP bound vitamin):

$[Bio]=[D]+[D_{Alb}]=(K_{alb}\cdot[Alb]+1)\cdot[D]$ (Eq. 7)

Example Calculation
Total 25(OH)-vitamin D=[Total]=40 ng/mL=$1.0\times 10^{-7}$ mol/L Total serum DBP=[Total DBP]=250 ug/mL=4.3×10⁻⁶ mol/L Total serum albumin=[Alb]=4.3 g/dL=6.4×10⁻⁴ mol/L $K_{alb}=6\times10^5 M^{-1}$ $K_{DBP}=7.0\times10^8 M^{-1}$ $a=2.7\times10^{11}$ $b=3325$ $c=-1\times10^{-7}$ Calculated concentration of free 25(OH)D=3.01×10⁻¹¹ mol/L=12.1 pg/mL Calculated concentration of bioavailable 25(OH)D=1.09× 10⁻⁸ mol/L=4.6 ng/mL

REFERENCES

1. Thomas M K, Lloyd-Jones D M, Thadhani R I, Shaw A C, Deraska D J, Kitch B T, Vamvakas E C, Dick I M, Prince R L, Finkelstein J S 1998 Hypovitaminosis D in medical inpatients. N Engl J Med 338(12):777-83.
2. Holick M F 2007 Vitamin D deficiency. N Engl J Med 357(3):266-81.
3. Bischoff-Ferrari H A, Zhang Y, Kiel D P, Felson D T 2005 Positive association between serum 25-hydroxyvitamin D level and bone density in osteoarthritis. Arthritis Rheum 53(6):821-6.
4. Valimaki V V, Alfthan H, Lehmuskallio E, Loyttyniemi E, Sahi T, Stenman U H, Suominen H, Valimaki M J 2004 Vitamin D status as a determinant of peak bone mass in young Finnish men. J Clin Endocrinol Metab 89(1):76-80.
5. Bischoff-Ferrari H A, Dietrich T, Orav E J, Dawson-Hughes B 2004 Positive association between 25-hydroxy vitamin D levels and bone mineral density: a population-based study of younger and older adults. Am J Med 116 (9):634-9.
6. Stone K, Bauer D C, Black D M, Sklarin P, Ensrud K E, Cummings S R 1998 Hormonal predictors of bone loss in elderly women: a prospective study. The Study of Osteoporotic Fractures Research Group. J Bone Miner Res 13(7):1167-74.
7. Cauley J A, Lacroix A Z, Wu L, Horwitz M, Danielson M E, Bauer D C, Lee J S, Jackson R D, Robbins J A, Wu C, Stanczyk F Z, LeBoff M S, Wactawski-Wende J, Sarto G, Ockene J, Cummings S R 2008 Serum 25-hydroxyvitamin D concentrations and risk for hip fractures. Ann Intern Med 149(4):242-50.
8. Jackson R D, LaCroix A Z, Gass M, Wallace R B, Robbins J, Lewis C E, Bassford T, Beresford S A, Black H R, Blanchette P, Bonds D E, Brunner R L, Brzyski R G, Caan B, Cauley J A, Chlebowski R T, Cummings S R, Granek I, Hays J, Heiss G, Hendrix S L, Howard B V, Hsia J, Hubbell F A, Johnson K C, Judd H, Kotchen J M, Kuller L H, Langer R D, Lasser N L, Limacher M C, Ludlam S, Manson J E, Margolis K L, McGowan J, Ockene J K, O'Sullivan M J, Phillips L, Prentice R L, Sarto G E, Stefanick M L, Van Horn L, Wactawski-Wende J, Whitlock E, Anderson G L, Assaf A R, Barad D 2006 Calcium plus vitamin D supplementation and the risk of fractures. N Engl J Med 354(7):669-83.
9. Dawson-Hughes B, Harris S S, Krall E A, Dallal G E, Falconer G, Green C L 1995 Rates of bone loss in postmenopausal women randomly assigned to one of two dosages of vitamin D. Am J Clin Nutr 61(5):1140-5.
10. Bischoff-Ferrari H A, Willett W C, Wong J B, Giovannucci E, Dietrich T, Dawson-Hughes B 2005 Fracture prevention with vitamin D supplementation: a meta-analysis of randomized controlled trials. JAMA 293(18):2257-64.
11. Dawson-Hughes B, Harris S S, Krall E A, Dallal G E 1997 Effect of calcium and vitamin D supplementation on bone density in men and women 65 years of age or older. N Engl J Med 337(10):670-6.
12. Chapuy M C, Arlot M E, Duboeuf F, Brun J, Crouzet B, Arnaud S, Delmas P D, Meunier P J 1992 Vitamin D3 and calcium to prevent hip fractures in the elderly women. N Engl J Med 327(23):1637-42.
13. Ooms M E, Roos J C, Bezemer P D, van der Vijgh W J, Bouter L M, Lips P 1995 Prevention of bone loss by vitamin D supplementation in elderly women: a randomized double-blind trial. J Clin Endocrinol Metab 80(4):1052-8.
14. Bischoff-Ferrari H A, Willett W C, Wong J B, Stuck A E, Staehelin H B, Orav E J, Thoma A, Kiel D P, Henschkowski J 2009 Prevention of nonvertebral fractures with oral vitamin D and dose dependency: a meta-analysis of randomized controlled trials. Arch Intern Med 169(6):551-61.
15. Kremer R, Campbell P P, Reinhardt T, Gilsanz V 2009 Vitamin D status and its relationship to body fat, final height, and peak bone mass in young women. J Clin Endocrinol Metab 94(1):67-73.
16. Hannan M T, Litman H J, Araujo A B, McLennan C E, McLean R R, McKinlay J B, Chen T C, Holick M F 2008 Serum 25-hydroxyvitamin D and bone mineral density in a racially and ethnically diverse group of men. J Clin Endocrinol Metab 93(1):40-6.
17. Sherman S S, Tobin J D, Hollis B W, Gundberg C M, Roy T A, Plato C C 1992 Biochemical parameters associated with low bone density in healthy men and women. J Bone Miner Res 7(10):1123-30.
18. Gerdhem P, Ringsberg K A, Obrant K J, Akesson K 2005 Association between 25-hydroxy vitamin D levels, physical activity, muscle strength and fractures in the prospective population-based OPRA Study of Elderly Women. Osteoporos Int 16(11):1425-31.
19. Gutierrez O M, Farwell W R, Kermah D, Taylor E N 2010 Racial differences in the relationship between vitamin D, bone mineral density, and parathyroid hormone in the National Health and Nutrition Examination Survey. Osteoporos Int.
20. Grant A M, Avenell A, Campbell M K, McDonald A M, MacLennan G S, McPherson G C, Anderson F H, Cooper C, Francis R M, Donaldson C, Gillespie W J, Robinson C M, Torgerson D J, Wallace W A 2005 Oral vitamin D3 and calcium for secondary prevention of low-trauma fractures in elderly people (Randomised Evaluation of Calcium Or vitamin D, RECORD): a randomised placebo-controlled trial. Lancet 365(9471):1621-8.
21. Porthouse J, Cockayne S, King C, Saxon L, Steele E, Aspray T, Baverstock M, Birks Y, Dumville J, Francis R, Iglesias C, Puffer S, Sutcliffe A, Watt I, Torgerson D J 2005 Randomised controlled trial of calcium and supplementation with cholecalciferol (vitamin D3) for prevention of fractures in primary care. BMJ 330(7498):1003.
22. Aloia J F, Talwar S A, Pollack S, Yeh J 2005 A randomized controlled trial of vitamin D3 supplementation in African American women. Arch Intern Med 165(14):1618-23.
23. Sanders K M, Stuart A L, Williamson E J, Simpson J A, Kotowicz M A, Young D, Nicholson G C 2010 Annual high-dose oral vitamin D and falls and fractures in older women: a randomized controlled trial. JAMA 303(18): 1815-22.
24. Mendel C M 1989 The free hormone hypothesis: a physiologically based mathematical model. Endocr Rev 10(3): 232-74.
25. Bikle D D, Siiteri P K, Ryzen E, Haddad J G 1985 Serum protein binding of 1,25-dihydroxyvitamin D: a reevaluation by direct measurement of free metabolite levels. J Clin Endocrinol Metab 61(5):969-75.
26. Safadi F F, Thornton P, Magiera H, Hollis B W, Gentile M, Haddad J G, Liebhaber S A, Cooke N E 1999 Osteopathy and resistance to vitamin D toxicity in mice null for vitamin D binding protein. J Clin Invest 103(2):239-51.
27. Chun R F, Lauridsen A L, Suon L, Zella L A, Pike J W, Modlin R L, Martineau A R, Wilkinson R J, Adams J, Hewison M 2010 Vitamin D-binding protein directs monocyte responses to 25-hydroxy- and 1,25-dihydroxyvitamin D. J Clin Endocrinol Metab 95(7):3368-76.
28. Bikle D D, Gee E 1989 Free, and not total, 1,25-dihydroxyvitamin D regulates 25-hydroxyvitamin D metabolism by keratinocytes. Endocrinology 124(2):649-54.
29. Bikle D D, Gee E, Halloran B, Kowalski M A, Ryzen E, Haddad J G 1986 Assessment of the free fraction of 25-hydroxyvitamin D in serum and its regulation by albumin and the vitamin D-binding protein. J Clin Endocrinol Metab 63(4):954-9.
30. Shaham O, Wei R, Wang T J, Ricciardi C, Lewis G D, Vasan R S, Can S A, Thadhani R, Gerszten R E, Mootha V K 2008 Metabolic profiling of the human response to a glucose challenge reveals distinct axes of insulin sensitivity. Mol Syst Biol 4:214.
31. Mazess R B, Barden H S, Bisek J P, Hanson J 1990 Dual-energy x-ray absorptiometry for total-body and regional bone-mineral and soft-tissue composition. Am J Clin Nutr 51(6):1106-12.
32. Marshall D, Johnell O, Wedel H 1996 Meta-analysis of how well measures of bone mineral density predict occurrence of osteoporotic fractures. BMJ 312(7041):1254-9.
33. Hans D, Downs R W, Jr., Duboeuf F, Greenspan S, Jankowski L G, Kiebzak G M, Petak S M 2006 Skeletal sites for osteoporosis diagnosis: the 2005 ISCD Official Positions. J Clin Densitom 9(1):15-21.
34. Vermeulen A, Verdonck L, Kaufman J M 1999 A critical evaluation of simple methods for the estimation of free testosterone in serum. J Clin Endocrinol Metab 84(10):3666-72.
35. Liel Y, Edwards J, Shary J, Spicer K M, Gordon L, Bell N H 1988 The effects of race and body habitus on bone mineral density of the radius, hip, and spine in premenopausal women. J Clin Endocrinol Metab 66(6):1247-50.
36. Halioua L, Anderson J J 1989 Lifetime calcium intake and physical activity habits: independent and combined effects on the radial bone of healthy premenopausal Caucasian women. Am J Clin Nutr 49(3):534-41.
37. Schneider G B, Benis K A, Flay N W, Ireland R A, Popoff S N 1995 Effects of vitamin D binding protein-macrophage activating factor (DBP-MAF) infusion on bone resorption in two osteopetrotic mutations. Bone 16(6):657-62.
38. Fang Y, van Meurs J B, Arp P, van Leeuwen J P, Hofman A, Pols H A, Uitterlinden A G 2009 Vitamin D binding protein genotype and osteoporosis. Calcif Tissue Int 85(2):85-93.
39. Sinotte M, Diorio C, Berube S, Pollak M, Brisson J 2009 Genetic polymorphisms of the vitamin D binding protein and plasma concentrations of 25-hydroxyvitamin D in premenopausal women. Am J Clin Nutr 89(2):634-40.
40. Engelman C D, Fingerlin T E, Langefeld C D, Hicks P J, Rich S S, Wagenknecht L E, Bowden D W, Norris J M 2008 Genetic and environmental determinants of 25-hydroxyvitamin D and 1,25-dihydroxyvitamin D levels in Hispanic and African Americans. J Clin Endocrinol Metab 93(9):3381-8.
41. Al-oanzi Z H, Tuck S P, Raj N, Harrop J S, Summers G D, Cook D B, Francis R M, Datta H K 2006 Assessment of vitamin D status in male osteoporosis. Clin Chem 52(2):248-54.
42. Lauridsen A L, Vestergaard P, Hermann A P, Brot C, Heickendorff L, Mosekilde L, Nexo E 2005 Plasma concentrations of 25-hydroxy-vitamin D and 1,25-dihydroxyvitamin D are related to the phenotype of Gc (vitamin D-binding protein): a cross-sectional study on 595 early postmenopausal women. Calcif Tissue Int 77(1):15-22.
43. Al-oanzi Z H, Tuck S P, Mastana S S, Summers G D, Cook D B, Francis R M, Datta H K 2008 Vitamin D-binding protein gene microsatellite polymorphism influences BMD and risk of fractures in men. Osteoporos Int 19(7):951-60.
44. Snijder M B, van Dam R M, Visser M, Deeg D J, Dekker J M, Bouter L M, Seidell J C, Lips P 2005 Adiposity in relation to vitamin D status and parathyroid hormone levels: a population-based study in older men and women. J Clin Endocrinol Metab 90(7):4119-23.
45. Cauley J A, Lui L Y, Ensrud K E, Zmuda J M, Stone K L, Hochberg M C, Cummings S R 2005 Bone mineral density and the risk of incident nonspinal fractures in black and white women. JAMA 293(17):2102-8.
46. van Driel M, Koedam M, Buurman C J, Hewison M, Chiba H, Uitterlinden A G, Pols H A, van Leeuwen J P 2006 Evidence for auto/paracrine actions of vitamin D in bone: 1alphahydroxylase expression and activity in human bone cells. FASEB J 20(13):2417-9.
47. Brent G A 1994 The molecular basis of thyroid hormone action. N Engl J Med 331(13):847-53.
48. van Hoof H J, Swinkels L M, Ross H A, Sweep C G, Benraad T J 1998 Determination of non-protein-bound plasma 1,25-dihydroxyvitamin D by symmetric (rate) dialysis. Anal Biochem 258(2):176-83.
49. Ginde A A, Mansbach J M, Camargo C A, Jr. 2009 Association between serum 25-hydroxyvitamin D level and upper respiratory tract infection in the Third National Health and Nutrition Examination Survey. Arch Intern Med 169(4):384-90.
50. Wactawski-Wende J, Kotchen J M, Anderson G L, Assaf A R, Brunner R L, O'Sullivan M J, Margolis K L, Ockene J K, Phillips L, Pottern L, Prentice R L, Robbins J, Rohan T E, Sarto G E, Sharma S, Stefanick M L, Van Horn L, Wallace R B, Whitlock E, Bassford T, Beresford S A, Black H R, Bonds D E, Brzyski R G, Caan B, Chlebowski R T, Cochrane B, Garland C, Gass M, Hays J, Heiss G, Hendrix S L, Howard B V, Hsia J, Hubbell F A, Jackson R D, Johnson K C, Judd H, Kooperberg C L, Kuller L H, LaCroix A Z, Lane D S, Langer R D, Lasser N L, Lewis C E, Limacher M C, Manson J E 2006 Calcium plus vitamin D supplementation and the risk of colorectal cancer. N Engl J Med 354(7):684-96.
51. Wang T J, Pencina M J, Booth S L, Jacques P F, Ingelsson E, Lanier K, Benjamin E J, D'Agostino R B, Wolf M, Vasan R S 2008 Vitamin D deficiency and risk of cardiovascular disease. Circulation 117(4):503-11.

Example 2

Bioavailable Vitamin D and Mineral Metabolism

Prior studies have yielded conflicting results regarding the association between 25-hydroxyvitamin D (25(OH)D) levels and mineral metabolism in end-stage renal disease (ESRD). Described herein are experiments testing the hypothesis that bioavailable vitamin D, the vitamin D fraction not bound to vitamin D binding protein (DBP), would associate more strongly with measures of mineral metabolism than total levels. Eighty nine patients with previously measured 25(OH)D and 1,25-dihydroxyvitamin D (1,25(OH)$_2$D) levels were identified from a cohort of incident U.S. dialysis patients. Stored serum samples were used to measure DBP, determine bioavailable 25(OH)D and 1,25(OH)$_2$D using previously validated formulae, and examine associations with measures of mineral metabolism and demographic factors. Both bioavailable 25(OH)D and bioavailable 1,25(OH)$_2$D were correlated with serum calcium (r=0.26, p=0.01 and r=0.23, p=0.02, respectively) whereas this association was absent for both total 25(OH)D (r=0.01, p=0.92) and total 1,25(OH)$_2$D (r=0.08, p=0.44). Racial differences in DBP and total 25(OH)D, but not bioavailable vitamin D, were observed. In univariate and multivariate regression analysis, only bioavailable 25(OH)D was associated with parathyroid hormone levels (p=0.007 and p=0.02, respectively). Accordingly, bioavailable 25(OH)D levels are better correlated with measures of mineral metabolism than total 25(OH)D levels in patients on hemodialysis.

Chronic kidney disease-associated mineral and bone disorder (CKD-MBD) is one of the most appreciated metabolic complications of CKD. As individuals progress toward end-stage renal disease (ESRD), declining renal 1a-hydroxylase activity leads to decreased conversion of 25-hydroxyvitamin D (25(OH)D) to the active 1,25-dihydroxyvitamin D (1,25(OH)$_2$D). These metabolic changes are believed to precipitate the hypocalcemia and secondary hyperparathyroidism that characterize CKD-MBD. Although 1,25(OH)$_2$D is thought to be the biologically active moiety, the majority of vitamin D circulates as 25(OH)D. (1) Low levels of 25(OH)D are common in ESRD; 79% of patients initiating dialysis have 25(OH)D levels below 30 ng/ml, and serum levels below this threshold are nearly universal among black ESRD patients. (2)

The free hormone hypothesis suggests that protein-bound hormones are relatively inactive while those liberated from binding proteins are free to exert biological activity. (3) For some hormones (e.g. testosterone), binding to albumin is considerably weaker than to a specific binding protein. Thus, albumin-bound hormone is often grouped with the free fraction and referred to as the "bioavailable" fraction. The majority (85-90%) of circulating 25(OH)D and 1,25(OH)$_2$D is tightly bound to vitamin D binding protein (DBP), with a smaller amount (10-15%) loosely bound to albumin. Less than 1% of circulating vitamin D exists in a free, unbound form. (4, 5) Described herein are experiments testing the hypothesis that the relationship between vitamin D and markers of mineral metabolism (e.g. PTH and calcium) in ESRD would be strengthened by use of DBP and albumin to determine bioavailable vitamin D levels. Given the patterns observed in other cohorts, it was further hypothesized that the lower 25(OH)D levels typically seen in black dialysis patients would be associated with lower and not necessarily lower bioavailable vitamin D levels in this group. (6, 7)

Results

Baseline characteristics of the 94 subjects included in this analysis, which are similar to those of a typical US hemodialysis population, are summarized in Table 5. None of the included subjects were recorded as receiving treatment with activated vitamin D, ergocalciferol, or cholecalciferol before initiating dialysis.

Mineral Metabolism and Vitamin D.

Figure 2:
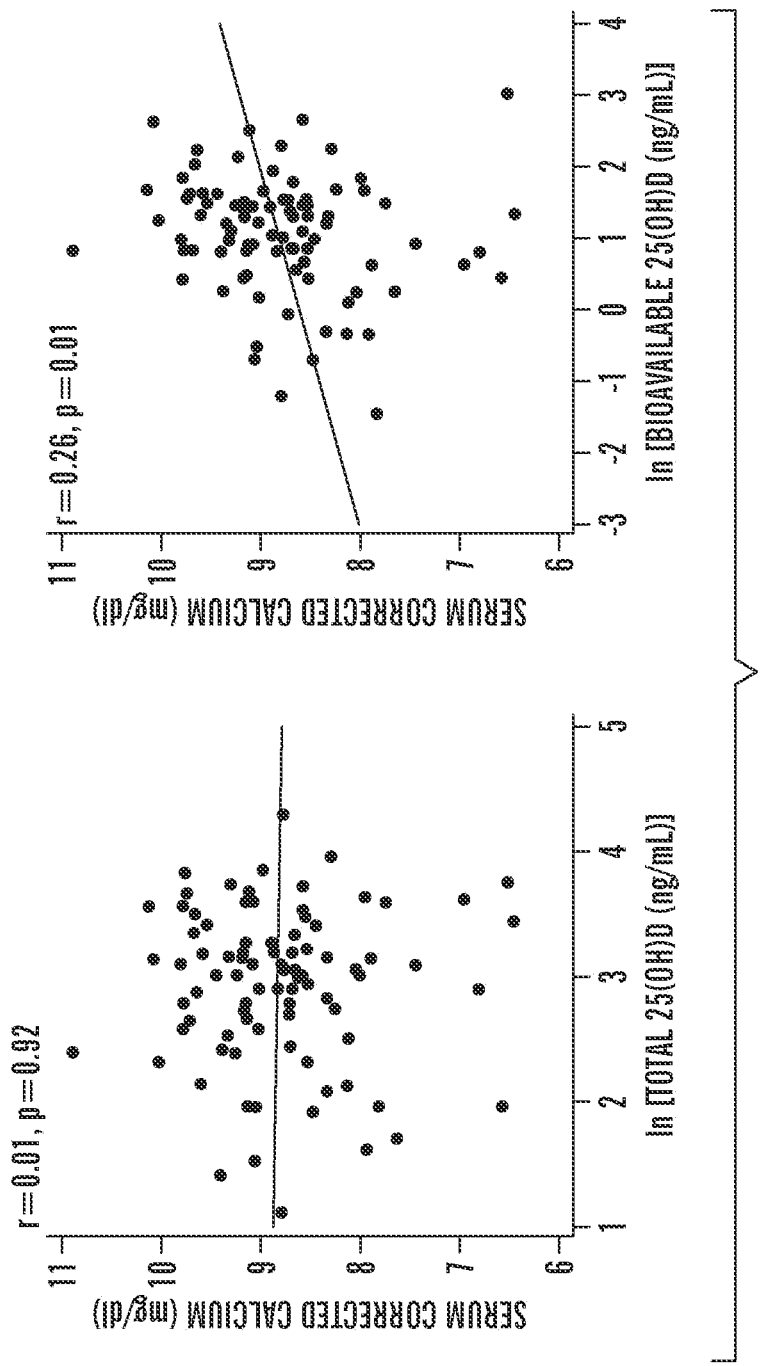
FIG. 2 depicts the relationship between total or bioavailable 25(OH)D and serum calcium. Total levels of 25(OH)D demonstrated no association with serum calcium levels (corrected for albumin) while bioavailable 25(OH)D levels were positively associated with serum calcium.

Baseline corrected calcium levels, measured within 14 days of chronic hemodialysis initiation, were not associated with total levels of either 25(OH)D (r=0.01, P=0.92) or 1,25 (OH)$_2$D (r=0.08, P=0.44). In contrast, calcium levels correlated positively with both bioavailable 25(OH)D (r=0.26, p=0.01) and bioavailable 1,25(OH)$_2$D (r=0.23, p=0.02). These relationships are plotted in FIG. 2. A single individual with the highest bioavailable 25(OH)D and bioavailable 1,25 (OH)$_2$D appeared to be an outlier with respect to the observed relationships, with both levels over 4 standard deviations above the mean. To examine the impact of this single data point, a sensitivity analysis was performed by repeating the analysis with this individual excluded. The relationship of calcium with bioavailable 25(OH)D (r=0.30, p=0.003) and bioavailable 1,25(OH)$_2$D (r=0.27, p=0.008) were both somewhat strengthened.

Phosphorus levels demonstrated no association with either total levels of 25(OH)D (r=0.14, P=0.19) or 1,25(OH)$_2$D (r=−0.01, P=0.94). Similarly, neither bioavailable 25(OH)D (r=−0.10, P=0.32) nor bioavailable 1,25(OH)$_2$D (r=−0.16, P=0.12) were significantly associated with phosphorus levels.

Alkaline phosphatase was not associated with either total or bioavailable forms of 25(OH)D or 1,25(OH)$_2$D (p>0.05 for all comparisons).

Figure 3:
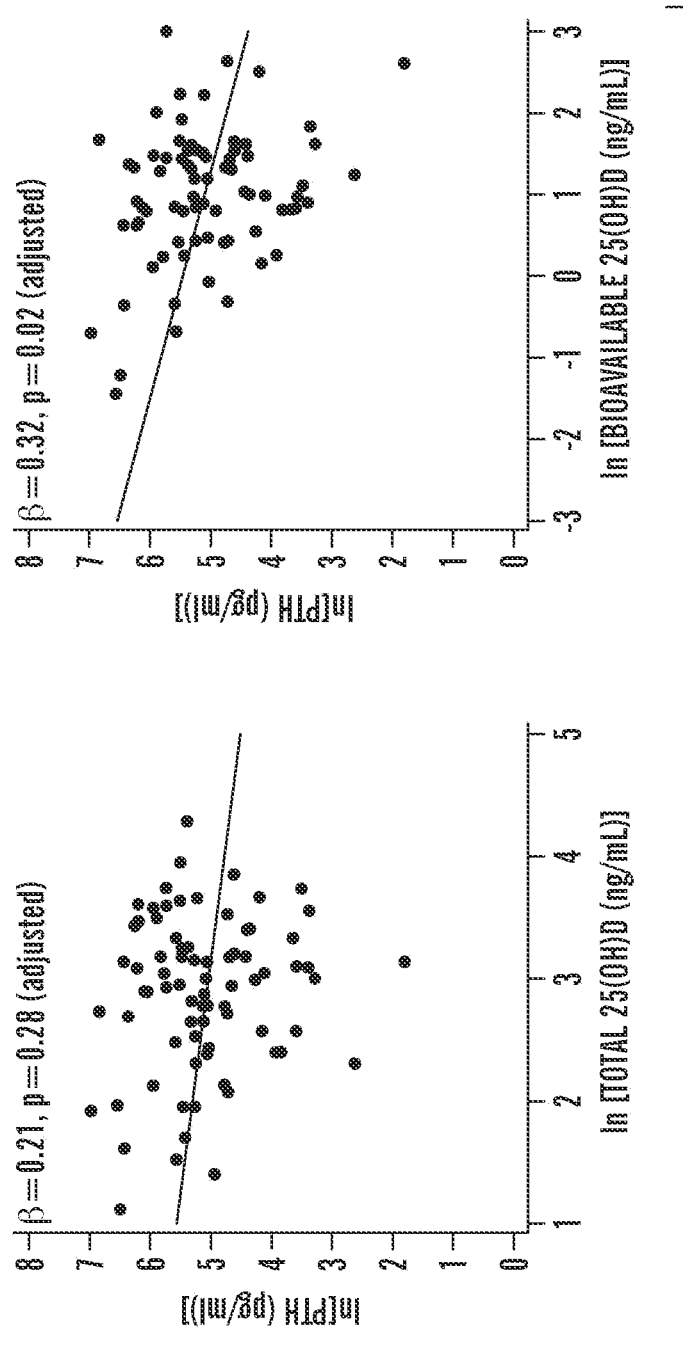
FIG. 3 depicts the relationship between total or bioavailable 25(OH)D and PTH. After adjustment for age, gender, race, and survival status at one year, bioavailable 25(OH)D was significantly negatively associated with PTH levels, while total 25(OH)D demonstrated no association with PTH.
Figure 4:
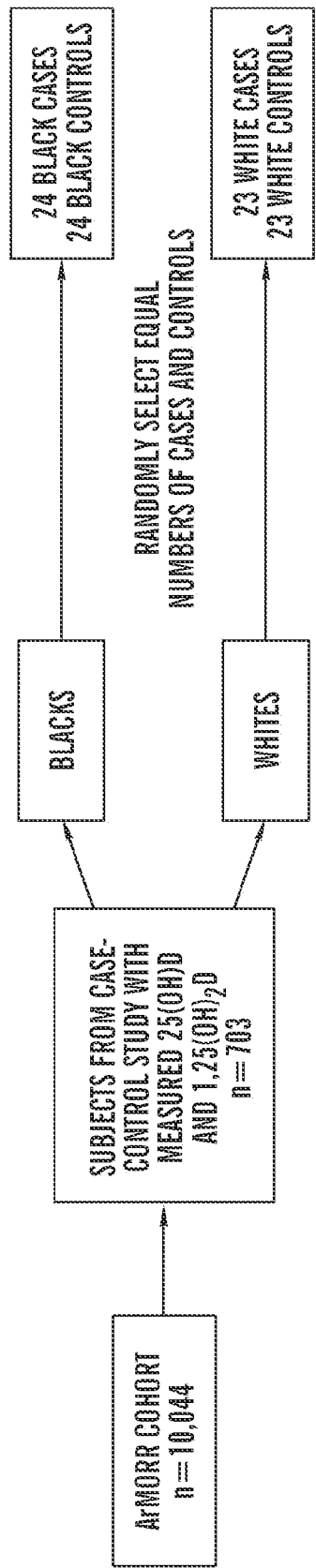
FIG. 4 depicts sample selection for Example 2. 25(OH)D and 1,25(OH)2D were previously measured as part of a case-control study within the ArMORR cohort. Equal numbers of cases (subjects who died within their first year on dialysis) and controls were randomly selected from each racial group.

The relationship between PTH and all four forms of vitamin D were examined in univariate and multivariate regression models. In univariate models, only bioavailable 25(OH)D was associated with PTH, with a −0.35 log decrease in PTH for each log increase in bioavailable 25(OH)D (p=0.01). In a multivariate model controlling for age, gender, race, and survival status at one year, this relationship remained unchanged ($\beta$=−0.32, p=0.02). A third model adding calcium, phosphorus, and bioavailable 1,25(OH)2D levels demonstrated similar results (Table 7). As with the calcium findings, both the unadjusted and adjusted coefficients became stronger when a single outlier was excluded (unadjusted: $\beta$=−0.40, p=0.003; adjusted: $\beta$=−0.36, p=0.01). In contrast, there was no significant association between total 25(OH)D and PTH (FIG. 3).

Patient Factors and Vitamin D.

Older individuals had higher total 25(OH)D levels (r=0.31, P=0.003) and bioavailable 25(OH)D (r=0.21, p=0.04). Neither total nor bioavailable 1,25(OH)$_2$D were associated with age. Female gender was associated with lower total 25(OH)D levels (median in men: 22.0 ng/dl, in women: 18.0 ng/dl; p=0.03). While females had numerically lower median total 1,25(OH)$_2$D and bioavailable 25(OH)D and 1,25(OH)$_2$D levels, none of these differences were statistically significant.

Black individuals had lower total 25(OH)D levels (median: 15.2 vs 23.2 ng/ml, p<0.001) but not bioavailable 25(OH)D levels (median: 3.8 vs. 2.8 ng/ml, p=0.21). The contrast in racial differences between these two forms of vitamin D was driven largely by lower DBP levels among blacks. This difference persisted even when examining only individuals who survived for one year on dialysis or those who died in this timeframe (Table 6). PTH levels did not differ significantly by race (median: 201 pg/ml [black] vs. 168 pg/ml [white], p=0.47). Neither total nor bioavailable 1,25(OH)$_2$D levels differed by race (p=0.07 and 0.49, respectively). Of note, we found no racial differences in systolic or diastolic blood pressure, diabetes, or BMI.

The study was not specifically powered to address whether systolic and diastolic blood pressure, BMI, and survival or a diagnosis of diabetic nephropathy or diabetes were associated with any form of vitamin D (data not shown).

Sensitivity Analysis.

Sensitivity analyses were performed to address the possibility that uremia might alter DBP's binding affinity with 25(OH)D or 1,25(OH)$_2$D. With DBP-binding coefficients that were 25% lower than those originally determined by Bikle, et al., (4, 5) bioavailable measures of both 25(OH)D (r=0.26, p=0.01) and 1,25(OH)$_2$D (r=0.22, p=0.03) remained associated with corrected calcium. Similar results were observed with 25% higher coefficients (bioavailable 25(OH)D:r=0.27, p=0.009; bioavailable 1,25(OH)$_2$D (r=0.24, p=0.02). Associations of bioavailable 25(OH)D with PTH remained statistically significant in both cases, with association coefficients changing less than 12% in either univariate or multivariate analyses.

Discussion

Using a retrospective cohort of incident dialysis patients, the relationship between measures of mineral metabolism (including serum calcium and PTH) and both total and bioavailable levels of vitamin D was examined. Described herein are results indicating that bioavailable 25(OH)D is associated with both corrected serum calcium levels and PTH, both of which are well-established measures of mineral metabolism in ESRD, while total 25(OH)D demonstrates no such associations. This data builds upon prior findings described elsewhere herein: analysis from two separate cohorts now support the hypothesis that bioavailable measures of vitamin D, which take into account binding of vitamin D to albumin and DBP, are more relevant to biological outcomes than are total levels, which are currently the standard measure of vitamin D status.

Some in vitro studies suggest that DBP-binding limits vitamin D activity in multiple target cells. (8, 9) Studies of DBP-null mice have shown that these animals display markedly reduced levels of 25(OH)D and 1,25(OH)$_2$D compared with wild-type mice, with a markedly reduced half-life. (10) Despite their low vitamin concentrations, when these mice are provided with a steady source of dietary vitamin D, they show no differences in serum calcium, phosphorus, alkaline phosphatase, and PTH compared to wild-type controls. These studies support the application of the free hormone hypothesis to vitamin D physiology, at least for some biological actions. Despite these findings, uptake of protein-bound hormone in cells expressing megalin appears to be important for some processes, so the biology underlying the findings described herein may be more complex than is immediately apparent and warrants further investigation. (11, 12)

Black patients were oversampled as the data presented in Example 1 suggested blacks have lower DBP levels than whites, an observation supported by the data described in this Example. As previously reported, the inventors and others observed that black race is associated with lower levels of total 25(OH)D. (2, 13) As might be expected from these two parallel racial differences (lower total 25(OH)D and lower DBP in blacks vs. whites), the levels of bioavailable 25(OH)D are similar, as described herein.

Despite similar bioavailable D levels between racial groups, and association between bioavailable 25(OH)D and PTH, black patients had numerically higher PTH levels than their white counterparts. Though this difference was not statistically significant in the sample used herein, larger samples from this cohort have found significantly higher levels of PTH in black individuals. (14) Bioavailable 25(OH)D did not differ by race, yet were negatively associated with PTH, suggesting that racial differences in PTH are not primarily driven by differences in 25(OH)D. Indeed, others have found that PTH levels in blacks are higher than those in whites, even in states of 25(OH)D sufficiency. (13)

Several studies have attempted to assess the metabolic consequences of low 25(OH)D levels in advanced CKD and ESRD, but have yielded conflicting results. Ergocalciferol, a form of nutritional vitamin D that can increase 25(OH)D levels, appears to affect parathyroid hormone (PTH) levels in stage 3, but not in stage 4, CKD. (15, 16) Moreover, some studies have demonstrated a significant association between 25(OH)D levels and PTH in ESRD, (17-19) while others have not. (20,21) Associations between 25(OH)D and serum calcium have been similarly mixed. (2, 17,22)

This contradictory data has led to confusion about the role that repleting 25(OH)D (e.g. with nutritional forms of vitamin D such as cholecalciferol or ergocalciferol) plays in the management of patients with ERSD. (23,24) In order to study the role of vitamin D insufficiency and identify patients who are most likely to benefit from repletion, it is critical to have a biologically relevant measure of vitamin D status. Notably, the experiments described herein failed to find any significant link between total or bioavailable 1,25(OH)$_2$D and relevant measures of mineral metabolism, echoing the general consensus that circulating serum levels of the active hormone are not useful as a measure of vitamin D status. (1)

A relationship between survival and vitamin D status was not found, though this sample had considerably less power to detect this relationship than prior studies, which have found that severe vitamin D insufficiency (typically defined levels <10 ng/ml) is associated with increased mortality. (19,25,26) None of the individuals in this analysis, who initiated dialysis in 2004 or 2005, had been treated with activated vitamin D analogs prior to initiating dialysis.

PTH is commonly used as a proxy for metabolic bone disease in dialysis patients, but has an imperfect association with bone disease. (27) Bone biopsies and non-invasive measures of bone density and structure were not available in this study and are potential targets for future analyses. As described in Example 1 herein, a relationship between bioavailable 25(OH)D and bone density in a healthy population, (6) has been demonstrated but it is not certain that this relationship will extend to the ESRD population given known alterations in mineral metabolism. Metabolic changes that accompany ESRD and/or dialysis, as well as genetic variants in DBP or other relevant proteins, have the potential to influence binding of 25(OH)D to DBP. Whereas the sensitivity analysis did not indicate that these factors are likely to affect the fundamental findings of this study, studies that directly measure bound and unbound fractions could improve upon the initial estimates and the equations used herein. Lastly, it is possible that measured 25(OH)D levels in this study were influenced by levels of 24,25(OH)$_2$D. Confirmation of the findings described herein with assays able to differentiate 25(OH)D, 24,25(OH)$_2$D, and 1,24,25(OH)$_3$D may further elucidate these biological relationships.

This study provides additional evidence to support the notion that bioavailable, rather than total, levels of vitamin D may be more relevant measures of vitamin D status with respect to its actions on mineral metabolism. While mineral metabolism has been the traditional focus of vitamin D actions, recent data suggest that its actions may be more widespread, with effects on the immune response, (28) hypertension, (29) and insulin sensitivity, (30), among others.

Methods

Accelerated Mortality on Renal Replacement (ArMORR) is a nationally representative prospective cohort study of incident chronic hemodialysis patients (n=10,044) who began renal replacement between Jul. 1, 2004 and Jul. 30, 2005 at one of 1,056 dialysis centers in the U.S. operated by Fresenius Medical Care, North America (FMC). (31) The ArMORR dataset contains a broad range of demographic and clinical data including co-existing medical conditions, laboratory results, as well as serum and plasma samples. Clinical data were collected prospectively, entered uniformly into a central database by practitioners at the point of care. All clinical data arriving at Fresenius undergo rigorous data quality assurance and quality control (QA/QC) auditing. Blood samples collected for clinical care were shipped to and processed by a central laboratory (Spectra East, Rockland, N.J., USA). After processing for routine clinical testing, remnant samples were shipped on ice to the ArMORR Investigators where the samples were aliquotted and stored in liquid nitrogen. This study was approved by the Institutional Review Board of the Massachusetts General Hospital, which waived the requirement for informed consent, and conducted in accordance with its ethical standards and the Declaration of Helsinki Study Population.

Between Jul. 1, 2004 and Jun. 30, 2005, 10,044 incident hemodialysis patients were prospectively enrolled into ArMORR. Subjects were identified who had 25(OH)D and 1,25(OH)$_2$D levels previously measured as part of a case-control survival study. (19) Based on prior results in a healthy population, we set a minimum sample size of 80 subjects. To ensure adequate power for racial comparisons, an approximately equal number of black (n=24) and white (n=23) patients were randomly selected from the controls, and an equal number of race-matched cases. Thus, the total sample size was n=94. Baseline laboratory values were measured from samples collected within 14 days of dialysis initiation.

Assays.

Total 25(OH)D and 1,25(OH)$_2$D were previously measured from thawed samples in duplicate using a commercially available radioimmunoassay (DiaSorin Inc, Stillwater, Minn., USA). The interassay coefficients of variation (CVs) for 25(OH)D were <3% at levels <30 ng/ml and for 1,25(OH)$_2$D were <6.5% at levels <32.5 pg/ml. Intact PTH (1-84) was measured using the Nichols Advantage Biointact-PTH assay by the centralized laboratory.

DBP was measured in duplicate in thawed serum samples by commercial enzyme linked immunosorbent assay (ELISA) (R&D Systems, Minneapolis, Minn., Catalog Number DVDBP0) according to the manufacturer's instructions. The assay was conducted after diluting serum samples 1 to 2,000 in Calibrator Diluent RD6-11 (R&D Systems Part Number 895489). Inter-assay CV was 8.5% at a concentration of 40 µg/ml. The assay recovered between 93 and 110% of a 100-200 µg/mL dose of exogenous DBP added to human serum samples containing between 25-200 µg/mL of endogenous DBP. There were no differences in the recovery of exogenous DBP in black patients or obese patients. The manufacturer reports no significant cross-reactivity with human albumin or vitamin D3. DBP levels were below the detection limit in 5 black patients who died within the first year of dialysis. These individuals were assigned a DBP value equal to the lowest detectable level (12.3 µg/dl).

Calculation of Bioavailable Vitamin D.

Equilibrium dialysis and centrifugal ultrafiltration dialysis have previously been used by some investigators to indirectly measure free vitamin D levels, allowing estimation of the binding affinity constants for 25(OH)D and 1,25(OH)$_2$D with DBP and albumin. (4, 5, 32) In these studies, calculated levels of free 25(OH)D and levels measured by centrifugal ultrafiltration were highly correlated (r=0.925). (5) Bioavailable and free vitamin D were calculated as described in Example 1 herein.

Bioavailable 1,25(OH)$_2$D levels were determined using the same approach using affinity constants previously derived by centrifugal ultrafiltration dialysis. (4) These affinity constants were previously validated in both healthy and cirrhotic individuals, (4, 5) but have not been directly assessed in hemodialysis patients. Therefore a sensitivity analysis of the main findings was performed using DBP binding coefficients for 25(OH)D and 1,25(OH)$_2$D that were 25% higher or 25% lower than previously measured values.

Statistical Analysis.

Prior to analysis, given the role of albumin as a binding protein for both vitamin D and calcium, serum calcium levels were corrected for albumin using the following equation: corrected calcium=total calcium+0.8*(4-albumin). (34) Spearman correlation analysis was performed to assess linear associations. Group comparisons of vitamin D levels were performed using the Wilcoxon rank sum test. To examine multivariable associations between bioavailable vitamin D and PTH, both variables (because of non-normal distribution) were natural-log transformed and analyzed using multivariate linear regression. All analyses were conducted using STATA Statistical Software (College Station, Tex.) version 11.

REFERENCES

1. Holick M F. Vitamin D deficiency. N Engl J. Med. 2007 Jul. 19; 357(3):266-281.
2. Bhan I, Burnett-Bowie S-A M, Ye J, Tonelli M, Thadhani R. Clinical measures identify vitamin D deficiency in dialysis. Clin J Am Soc Nephrol. 2010 March; 5(3):460-467.
3. Mendel C M. The free hormone hypothesis: a physiologically based mathematical model. Endocr Rev. 1989 August; 10(3):232-274.
4. Bikle D D, Siiteri P K, Ryzen E, Haddad J, Gee E. Serum Protein Binding of 1,25-Dihydroxyvitamin D: A Reevaluation by Direct Measurement of Free Metabolite Levels. J Clin Endocrinol Metab. 1985 Nov. 1; 61(5):969-975.
5. Bikle D D, Gee E, Halloran B, Kowalski M A, Ryzen E, Haddad J G. Assessment of the Free Fraction of 25-Hydroxyvitamin D in Serum and Its Regulation by Albumin and the Vitamin D-Binding Protein. J Clin Endocrinol Metab. 1986 Oct. 1; 63(4):954-959.
6. Powe C E, Ricciardi C, Berg A H, Erdenesanaa D, Collerone G, Ankers E, et al. Vitamin D-binding protein modifies the vitamin D-bone mineral density relationship. J Bone Miner Res. 2011 July; 26(7):1609-1616.
7. Powe C E, Seely E W, Rana S, Bhan I, Ecker J L, Karumanchi S A, et al. First trimester vitamin D, vitamin D binding protein, and subsequent preeclampsia. Hypertension. 2010 October; 56(4):758-763.
8. Chun R F, Lauridsen A L, Suon L, Zella L A, Pike J W, Modlin R L, et al. Vitamin D-binding protein directs monocyte responses to 25-hydroxy- and 1,25-dihydroxyvitamin D. J Clin Endocrinol Metab. 2010 July; 95(7):3368-3376.
9. Bikle D D, Gee E. Free, and not total, 1,25-dihydroxyvitamin D regulates 25-hydroxyvitamin D metabolism by keratinocytes. Endocrinology. 1989 February; 124(2): 649-654.
10. Safadi F F, Thornton P, Magiera H, Hollis B W, Gentile M, Haddad J G, et al. Osteopathy and resistance to vitamin D toxicity in mice null for vitamin D binding protein. J Clin Invest. 1999 January; 103(2):239-251.
11. Hammes A, Andreassen T K, Spoelgen R, Raila J, Hubner N, Schulz H, et al. Role of endocytosis in cellular uptake of sex steroids. Cell. 2005 Sep. 9; 122(5):751-762.
12. Lundgren S, Carling T, Hjälm G, Juhlin C, Rastad J, Pihlgren U, et al. Tissue distribution of human gp330/ megalin, a putative Ca(2+)-sensing protein. J. Histochem. Cytochem. 1997 March; 45(3):383-392.
13. Gutiérrez O M, Farwell W R, Kermah D, Taylor E N. Racial differences in the relationship between vitamin D, bone mineral density, and parathyroid hormone in the National Health and Nutrition Examination Survey. Osteoporosis Int. 2011 June; 22(6):1745-1753.
14. Wolf M, Betancourt J, Chang Y, Shah A, Teng M, Tamez H, et al. Impact of Activated Vitamin D and Race on Survival among Hemodialysis Patients. J Am Soc Nephrol. 2008 Apr. 9; 19(7):1379-1388.
15. Zisman A L, Hristova M, Ho L T, Sprague S M. Impact of Ergocalciferol Treatment of Vitamin D Deficiency on Serum Parathyroid Hormone Concentrations in Chronic Kidney Disease. Am J. Nephrol. 2007; 27(1):36-43.
16. Al-Aly Z, Qazi R A, González E A, Zeringue A, Martin K J. Changes in serum 25-hydroxyvitamin D and plasma intact PTH levels following treatment with ergocalciferol in patients with CKD. Am J Kidney Dis. 2007 Jul. 1; 50(1):59-68.
17. Jean G, Charra B, Chazot C. Vitamin D Deficiency and Associated Factors in Hemodialysis Patients. J Ren Nutr. 2008 September; 18(5):395-399.
18. Ravani P, Malberti F, Tripepi G, Pecchini P, Cutrupi S, Pizzini P, et al. Vitamin D levels and patient outcome in chronic kidney disease. Kidney Int. 2009 Jan. 1; 75(1):88-95.
19. Wolf M, Shah A, Gutierrez O, Ankers E, Monroy M, Tamez H, et al. Vitamin D levels and early mortality among incident hemodialysis patients. Kidney Int. 2007 Oct. 1; 72(8):1004-1013.
20. González E A, Sachdeva A, Oliver D A, Martin K J. Vitamin D insufficiency and deficiency in chronic kidney disease. A single center observational study. Am J. Nephrol. 2004 August; 24(5):503-510.
21. London G M, Guérin A P, Verbeke F H, Pannier B, Boutouyrie P, Marchais S J, et al. Mineral metabolism and arterial functions in end-stage renal disease: potential role of 25-hydroxyvitamin D deficiency. J Am Soc Nephrol. 2007 Feb. 1; 18(2):613-620.
22. London G M, Marty C, Marchais S J, Guerin A P, Metivier F, de Vernejoul M-C. Arterial calcifications and bone histomorphometry in end-stage renal disease. J Am Soc Nephrol. 2004 Jul. 1; 15(7):1943-1951.
23. Nigwekar S U, Bhan I, Thadhani R. Nutritional vitamin D in dialysis patients: what to D-iscern? Nephrology Dialysis Transplantation. 2011 March; 26(3):764-766.
24. Bhan I, Hewison M, Thadhani R. Dietary vitamin D intake in advanced CKD/ESRD. Semin Dial. 2010 June; 23(4): 407-410.
25. Drechsler C, Pilz S, Obermayer-Pietsch B, Verduijn M, Tomaschitz A, Krane V, et al. Vitamin D deficiency is associated with sudden cardiac death, combined cardiovascular events, and mortality in haemodialysis patients. Eur Heart J. 2010 September; 31(18):2253-2261.
26. Drechsler C, Verduijn M, Pilz S, Dekker F W, Krediet R T, Ritz E, et al. Vitamin D status and clinical outcomes in incident dialysis patients: results from the NECOSAD study. Nephrol Dial Transplant. 2011 March; 26(3):1024-1032.
27. Ott S M. Review article: Bone density in patients with chronic kidney disease stages 4-5. Nephrology. 2009 June; 14(4):395-403.
28. Bhan I, Camargo C A, Wenger J, Ricciardi C, Ye J, Borregaard N, et al. Circulating levels of 25-hydroxyvitamin D and human cathelicidin in healthy adults. J Allergy Clin Immunol. 2011 May; 127(5):1302-4.e1.
29. Forman J P, Giovannucci E, Holmes M D, Bischoff-Ferrari H A, Tworoger S S, Willett W C, et al. Plasma 25-hydroxyvitamin D levels and risk of incident hypertension. Hypertension. 2007 May; 49(5):1063-1069.
30. Chonchol M, Scragg R. 25-Hydroxyvitamin D, insulin resistance, and kidney function in the Third National Health and Nutrition Examination Survey. Kidney Int. 2007 Jan. 1; 71(2):134-139.
31. Gombart A F, Bhan I, Borregaard N, Tamez H, Camargo C A, Koeffler H P, et al. Low plasma level of cathelicidin antimicrobial peptide (hCAP18) predicts increased infectious disease mortality in patients undergoing hemodialysis. Clin. Infect. Dis. 2009 Feb. 15; 48(4):418-424.
32. van Hoof H J, Swinkels L M, Ross H A, Sweep C G, Benraad T J. Determination of non-protein-bound plasma 1,25-dihydroxyvitamin D by symmetric (rate) dialysis. Anal. Biochem. 1998 May 1; 258(2):176-183.
33. Vermeulen A, Verdonck L, Kaufman J M. A critical evaluation of simple methods for the estimation of free testosterone in serum. J Clin Endocrinol Metab. 1999 October; 84(10):3666-3672.
34. Correcting the calcium. Br Med J. 1977 Mar. 5; 1(6061):598.

Example 3

Bioavailable Vitamin D in Pregnant Women

A pilot study in pregnant women enrolled in the MOMS cohort was conducted to determine if VDBP modifies the relationship between first trimester 25(OH)D levels and subsequent development of preeclampsia or gestational diabetes. Although the sample sizes in pregnant women were small, total 25(OH)D levels were significantly lower among blacks (18.8 [10.8-24.2] ng/mL, n=9), Hispanics (21.4 [16.7-27.7] ng/mL n=61), and Asians (22.5 [14.8-29.7] ng/ml, n=8) compared to white non-Hispanics (32.1 [26.3-36.6] ng/mL, n=127; P<0.03 for all comparisons). VDBP levels were significantly lower in blacks (97.2 [73.6-361.2] µg/ml) compared to whites (504 [338-700] µg/ml, P<0.001). Bioavailable 25(OH)D levels were similar in white and black subjects.

Example 4

Bioavailable Vitamin D and Racial Variability

Black individuals consistently have low 25-hydroxy vitamin D (25[OH]D) levels[15-19] and are at especially high risk for poor outcomes linked to vitamin D sufficiency.[15] Paradoxically, blacks have higher BMD and a lower risk of osteoporosis than whites.[20] Although 25(OH)D is the marker currently considered most suitable for assessing vitamin D status,[2,21] studies have shown a weaker relationship of 25(OH)D to BMD in blacks and other minorities compared to whites.[18,19,22,23] Importantly, the BMD-vitamin D relationship in blacks needs clarification,[18-20] and questions about how to define clinically relevant vitamin D insufficiency, the impact of race on measures of vitamin D status, how to reliably identify who needs supplementation with vitamin D (and with how much) to favorably impact disease outcomes remain unanswered.[2,15]

The research described herein has the potential to redefine who is vitamin D deficient and to significantly improve diagnosis and the efficiency of strategies for prophylaxis and treatment. The hypothesis that invokes the free hormone hypothesis in regards to bioavailable vitamin D can be investigated using a large cohort of black and white subjects enrolled in the Healthy Aging in Neighborhoods of Diversity across the Life Span (HANDLS) study. Studies described in Examples 1, 2 and 3 herein in various populations (healthy volunteers, individuals with end-stage renal disease (ESRD), pregnant women) measured VDBP, total 25(OH)D and calculated free 25(OH)D. These results indicate that 25(OH)D levels are directly correlated with VDBP levels and inversely correlated with free 25(OH)D levels. The data also reveal substantial racial differences in VDBP levels. Blacks had 25-60% lower VDBP levels than whites, while free and bioavailable 25(OH)D levels were similar. In healthy adults, non-VDBP bound 25(OH)D levels were strongly associated with BMD, whereas total 25(OH)D levels and PTH were not.[23] After adjusting for race in patients with ESRD, both VDBP and free 25(OH)D (but not total 25(OH)D), were associated with PTH.[31] These correlations (or lack thereof) between unbound vs total 25(OH)D and BMD and racial differences in VDBP levels led to the hypothesis that VDBP modifies the relationship between BMD and 25(OH)D.[23] Total 25(OH)D may not faithfully reflect physiologically relevant vitamin D status, particularly in relation to BMD and questions the clinical relevance of 25(OH)D assays in all races.[33]

VDBP levels may be the previously unrecognized link that explains the BMD-vitamin D paradox in blacks. Using stored blood samples from black and white subjects enrolled in HANDLS (n~2,200), the following hypotheses can be tested: 1. Blacks have lower levels of VDBP and total 25(OH)D levels, but similar levels of free and bioavailable 25(OH)D as whites. 2. Free and bioavailable 25(OH)D levels are independently associated with BMD in blacks and whites, inversely and linearly associated with PTH levels, and these associations are stronger than those between total 25(OH)D and BMD.

Aim 1: To determine VDBP, total and bioavailable 25(OH)D, and PTH levels in blacks vs whites.

Aim 2: To test for associations between BMD, bioavailable 25(OH)D, and PTH compared to total 25(OH)D in blacks vs whites.

The studies described herein, (1) apply well-established mechanisms of hormone biology; (2) demonstrate that bioavailable/free 25(OH)D is more strongly associated with outcomes than total 25(OH)D; (3) can aid future clinical trial designs in which vitamin D insufficiency will be redefined; (4) aim to individualize diagnosis and treatment based on race to improve therapeutic and cost-efficiency of our limited health care resources, and (5) question current public health paradigms for clinical decision-making about who is vitamin D deficient, who should be treated, and who can avoid being treated.

25(OH)D Insufficiency is Even More Common in Blacks than in Whites.

According to current cutoffs defining vitamin D deficiency in terms of 25(OH)D, approximately 50% of African Americans in the US are either chronically or seasonally at risk.[48] Racial disparities in vitamin D status between blacks and whites may arise from insufficient dietary intake or impaired conversion of vitamin D by sunlight due to skin pigmentation.[16] Holick[48] reported that in Boston, 84% of black men and women >65 years old were vitamin D deficient at the end of the summer, which is typically when vitamin D levels are highest. Deficiency was attributed to several factors including insufficient milk intake because of lactose intolerance, decreased synthesis of vitamin D3 in the skin due to pigmentation, and avoidance of sun exposure to minimize skin pigmentation.[48] According to the 1988-1994 National Health and Nutrition Examination Survey (NHANES)III, 42% of black women (15-49 years old) were vitamin D deficient at the end of the winter compared to 4% of white women.[49] Concentrations in serum of 25(OH)D measured during different seasons showed substantially lower levels in blacks (adjusted for body weight and vitamin D intake) throughout all seasons and smaller seasonal increases during summer months than whites.[50] These racial differences are reinforced in more recent NHANES 2001-2006 data.[22,51] Table 9 summarizes several representative studies reporting vitamin D levels in blacks vs whites. In most studies, the discrepancy between races does not extend to 1,25 $(OH)_2D$ levels, which are generally similar in blacks and whites.[50,52]

As described in Example 2 herein, data from ArMORR (Accelerated Mortality in Renal Replacement which includes ESRD patients at the initiation of dialysis prior to any vitamin D replacement) demonstrated that mean 25(OH)D levels were 23.2±13.7 (SD) ng/mL in whites (n=653) and 16.9±10.9 in blacks (n=372) (P<0.05). Similar results were found from a randomly-selected race-matched sample from ArMORR in which total 25(OH)D was 27.3±15.3 ng/mL in whites (n=23) and 16.4±10.1 in blacks (n=24)(P=0.004).[31] Given that: (1) the incidence of vitamin D insufficiency is consistently higher in blacks than whites; (2) the range of total 25(OH)D cutoff levels used to define insufficiency is wide; and (3) correlation between 25(OH)D with mineral markers and BMD is lacking,[23,40] the public health implications of continued reliance on total 25(OH)D for diagnosis and treatment are broad. The marker used to diagnose and supplement vitamin D deficient states must be appropriate for racially diverse populations. Based on the data described in Example 2, it is hypothesized that total 25(OH)D may not be uniformly applicable to all races. The definition of vitamin D insufficiency needs to be revisited.

Improving the understanding of vitamin D status among different races is expected to have broadly significant therapeutic and public health implications. Specifically, by improving knowledge about vitamin D biology, the IOM's public health position on vitamin D replacement can be refined to consider race and VDBP levels when determining vitamin D targets.

The inventors have previously reported a curvilinear relationship between PTH and total 25(OH)D that PTH in older hospitalized patients.[40] PTH was inversely correlated to total 25(OH)D levels <15 ng/mL. A similar strong inverse correlation was observed in a large (n=825) cohort of incident dialysis patients.[43] At higher total 25(OH)D levels (≥15 ng/mL), the correlation with PTH was not as clear.[40] As described in Example 1, in younger healthy subjects whose mean total 25(OH)D levels were 25.7±11.1 ng/mL (64.2±27.7 nmol/L), PTH was not correlated with total, bioavailable 25(OH)D, or BMD. This suggests that the association between free or bioavailable 25(OH)D levels and BMD is not mediated via PTH in individuals whose vitamin D status is relatively normal. However, due to the relatively small sample size of the healthy cohort, these correlations may not have been evident. Example 2 indicates that, after adjusting for race, free 25(OH)D (but not total 25[OH]D) correlates with PTH.

The large HANDLS dataset (n~2,200) can be used to determine if PTH is better and more linearly correlated with free- or bioavailable 25(OH)D than with total 25(OH)D. Additionally, the question of whether racial differences exist among these variables can be explored. By following subjects with BMD measurements at baseline for changes over time in the HANDLS cohort, the measures of vitamin D which best predict changes in BMD in different racial groups can be identified.

Why do blacks have lower levels of vitamin D yet higher BMD than other races? Despite having lower levels of 25(OH)D, blacks have higher BMD[19,20] and a lower risk of osteoporotic fractures than whites.[20,58,59] Although factors other than vitamin D are likely to contribute, it has been hypothesized that blacks have adaptive responses that protect the skeleton even when 25(OH)D is low. 16 Skeletal resistance to parathyroid hormone (PTH) activity and bone-sparing adaptations that promote beneficial skeletal effects of active vitamin D (1,25 dihydroxyvitamin D [1,25(OH)$_2$D]) have been proposed to explain this paradox.[16] For example, moderately low 25(OH)D can induce PTH-stimulated synthesis of 1,25(OH)$_2$D in the kidney.[60,61] Using data from NHANES 2003-2006, Gutierrez and colleagues[22] observed that BMD decreased (p<0.01) with serum 25(OH)D and calcium intake among whites and Mexican-Americans, but not among blacks (p=0.2).[22] They proposed that relationships between 25(OH)D, BMD, and PTH differ by race. Other studies have also shown that the relationship between 25(OH)D and BMD in blacks is weaker than in whites or is nonexistent.[18,19]

Higher PTH levels have been reported in blacks than in non-blacks.[22,31] Lower PTH may be related to low 25(OH)D, an adaptation to minimize urinary calcium losses and increase 1,25(OH)$_2$D activity. However, racial differences in PTH level persist even when total 25(OH)D is high,[22] and PTH suppression by 25(OH)D may occur at a lower threshold in blacks versus non-blacks.[22,62] Thus, in addition to racial differences between BMD and total 25(OH)D levels, the relationships between PTH and free- and bioavailable 25(OH)D vs total 25(OH)D may also differ by race. It is proposed herein that the VDBP hypothesis will help explain or better understand these relationships.

Although the relationship of VDBP, 25(OH)D, and BMD has not been clearly established in humans, animal studies suggest a role for VDBP in modulating the rates of bioavailability, activation, and end-organ responsiveness of vitamin D metabolism,[66] as well as a role in the BMD-25(OH)D paradox in blacks. That is, despite having lower total 25(OH)D levels, free and bioavailable 25(OH)D levels in blacks may in fact be normal or even higher than normal, as a result of relatively low VDBP concentrations as explained by the free-hormone hypothesis. Conversely, skin with light pigment captures vitamin D from the environment more readily, and higher VDBP levels may be an adaptation for regulating bioavailable vitamin D. Genetic data are collected in HANDLS and phenotyping has been performed by the HANDLS investigators with results published in peer reviewed journals.[67,68]

The significance of circulating VDBP levels with regard to the biological activity of vitamin D in humans is unclear.[2,18,19,21,22,24-26,30] Several properties that influence the bioavailability of vitamin D are analogous to those of the lipid-soluble androgen hormone, testosterone (T). In the circulation, total T is 60% bound to sex hormone binding globulin (SHBG), whereas 38% is albumin-bound and 2% is available as free-T.[75] Non-SHBG-bound T and free T are the biologically active components of circulating T (bio-T).[76] The method used to calculate bio-T includes measured values of total T, albumin, SHBG and their binding constants into a mathematical model of tripartite binding. A strong correlation exists between measured bio-T and calculated bio-T.[77] Using similar methods, concentrations of free and bioavailable vitamin D may be calculated using measured affinity constants to VDBP and albumin, as described in Example 1 and elsewhere herein. Calculated free D values are highly correlated with measured values of free D, as validated by Bikle et al.[38,70] and can be used to estimate circulating free vitamin D concentrations.

Studies on the various circulating forms of vitamin D have shown that vitamin D is 85-90% bound to VDBP, 10-15% is albumin-bound, and only 1% circulates freely.[70] Given that the majority of vitamin D is bound to VDBP, what is the role of VDBP in vitamin D physiology? Multiple animal models have demonstrated that VDBP is important as a high affinity serum reservoir for Vitamin D. VDBP-deficient animals have no high affinity serum carrier for the vitamin; as a consequence of this their serum vitamin concentrations are significantly decreased, and without a high affinity carrier they rapidly excrete vitamin D in the urine. Together these events cause mice to quickly develop a vitamin insufficiency when put on diets low in Vitamin D.[66] Although these animals are prone to rapidly develop vitamin insufficiency in the absence of dietary vitamins, when dietary vitamin D is abundant, the animals are able to maintain calcium homeostasis and do not appear to suffer from hypovitaminosis.

In contrast, animals that express VDBP but are missing the receptors required for renal resorption of VDBP from glomerular ultrafiltrate display an even more dramatic phenotype. A significant amount of VDBP (and albumin) are filtered by the glomerulus.[72,78] The filtered VDBP and albumin are normally recovered in the proximal tubules, however, by megalin/cubulin receptor-mediated endocytosis. In the absence of megalin, vitamin D is sequestered by VDBP to the urine, producing rapid and complete vitamin insufficiency even when provided with a vitamin-enriched diet, and develop severe abnormalities in calcium homeostasis and bone disease.[72]

The conclusions drawn from these animal models support a model where VDBP and its endocytic receptors act as serum reservoirs and provide a mechanism for the prevention of urinary losses. Based upon tissue culture and animal model studies, it is unclear whether VDBP is involved in the intracellular delivery of 25(OH)D to its target tissues. The high affinity of extracellular VDBP for 25(OH)D may prevent spontaneous dissociation and diffusion into cells. Experiments in tissue culture have shown that when vitamin D-responsive osteoblasts or monocytes are treated with vitamin D, addition of VDBP in the media actually inhibits 25(OH)D endocytosis and intracellular signaling.[73,74] Furthermore, although VDBP-deficient mice have very low serum vitamin concentrations, if they are provided with sufficient vitamin D in their diet they do not suffer from problems with calcium homeostasis, and they accumulate normal amounts of 1,25 (OH)$_2$D in their tissues.[73]

Together, these biochemical, tissue culture, and animal model studies suggest that although VDBP helps to prevent insensible urinary losses, retain serum vitamin levels, and maintain stable vitamin D concentrations between meals, it is not necessary for intracellular delivery of 25(OH)D or its conversion to active 1,25(OH)$_2$D. If VDBP is not absolutely necessary for intracellular delivery of 25(OH)D, and since albumin-bound 25(OH)D is the second most abundant circulating form of the vitamin, an alternative pathway for vitamin D delivery to the proximal tubules of the kidney and other target tissues must be considered: endocytic delivery of albumin bound vitamin D. Albumin and VDBP are in the same protein family, and they both share megalin and cubilin as their endocytic receptors. The most important target for vitamin D delivery and its actions is the epithelium of the proximal convoluted tubule (PCT). Recent evidence has unexpectedly emerged that a large amount of albumin and VDBP are filtered through the glomerular basement membrane and then resorbed in the proximal tubule.[79,80] In the PCT, albumin is resorbed by cubulin-mediated endocytosis,[79] and VDBP is endocytosed by megalin binding (although cubilin may also play a role).[72,78] Megalin and cubilin are part of the same receptor complex, and thus albumin and VDBP share very similar endocytic pathways. The fact that both these proteins (and any vitamin bound to them) are delivered to the renal epithelium in such large amounts suggests that either one may be a vehicle of intracellular vitamin delivery. Once these proteins are inside, however, albumin may be the principal source of diffusible 25(OH)D given its low 25(OH)D affinity compared to VDBP. It has recently been demonstrated that the large amounts of endocytosed albumin are actually transported through the renal epithelium and back to the circulation intact by transcytosis.[81] Given the structural and evolutionary similarities between albumin and VDBP, and their shared endocytic receptors, it is hypothesized that VDBP also participates in transcytosis.

The transcytosis of albumin (and possibly VDBP) through renal epithelial cells described above thus saves these cells from the burden of having to degrade this mass in the lysosomes, which, based upon the estimated amounts of albumin flux would be toxic to the cells. This recent finding is significant to vitamin D bioavailability in megalin-expressing target tissues because transcytosis would also provide for an ideal autocrine mechanism for efficient intracellular delivery of vitamin D that can be regulated. As albumin transits through the cells, it would release 25(OH)D through spontaneous dissociation, providing a nearby source of vitamin D to intracellular VDBPs, CYP27B1 hydroxylase, and VDR receptors. In contrast, although VDBP should not release of much of its bound vitamin during transit through the tubular epithelium, it would ensure efficient recovery of 25(OH)D from the urine and its return to the circulation.

Given this alternative model of vitamin D physiology, because the majority of total serum vitamin D is bound to VDBP, and because VDBP-bound vitamin represents an inert serum reservoir for vitamin storage, although measurement of total 25(OH)D may indicate total body stores, serum concentrations of total 25(OH)D will often not reflect vitamin bioactivity or sufficiency. Non-VDBP bound bioavailable vitamin D, on the other hand, may be a more faithful indicator of vitamin D sufficiency. This model agrees with results from clinical studies described above herein and it provides a model that may explain the differences in 25(OH)D concentrations and differences in BMD between white and black subjects.

Comparing men with osteoporosis to men without osteoporosis, Al-oanzi and colleagues[24] found that total 25(OH)D$_3$ levels were similar in both groups, but VDBP levels were significantly higher (P<0.001) Calculated free 25(OH)D3 and 1,25(OH)$_2$D3 were significantly lower in men with vs without osteoporosis (p<0.00001).[24] Whereas total 25(OH)D3 levels provided only a crude estimate of vitamin D status, measurement of free hormones provided more biologically relevant information. As described herein in Example 1 (young healthy adults; n=49) BMD is not well-correlated with total 25(OH)D but that free and bioavailable 25(OH)D are much more strongly associated with BMD. Despite wide variation in VDBP concentrations in the study cohort, mean VDBP levels were significantly lower in nonwhite than in white subjects (2.87±2.04, 4.94±2.43, respectively; P<0.001). As demonstrated in Example 2 herein, a randomly selected group of racially-matched ESRD patients suggested that VDBP may also mediate vitamin D activity in ESRD. Lower VDBP levels were found in blacks vs whites. Serum calcium correlated with free 25(OH)D and 1,25(OH)$_2$D, but not with total 25[OH]D and free 25(OH)D and VDBP levels—but not total 25[OH]D—were significantly associated with PTH. As discussed in Example 3 herein, a study in pregnant women also revealed lower VDBP and total 25(OH)D levels in blacks vs whites, whereas bioavailable 25(OH)D was similar regardless of race.

On the basis of the data described herein, it is hypothesized that VDBP modifies the relationship of BMD and 25(OH)D. More specifically, decreased concentrations of VDBP in nonwhites may explain the lower average concentrations of total 25(OH)D that have been consistently reported herein and elsewhere. Because of lower VDBP levels, bioavailable vitamin D will be normal or even increased, perhaps explaining the apparent reduced risk of osteoporosis in blacks compared to whites.

The invention described herein incorporates innovative hypotheses and approaches that: 1. Apply mechanisms of hormone biology that are well-established in other steroid hormone research (e.g. testosterone and thyroid hormones) to explain the biological actions of vitamin D; 2. solves a complex problem that has puzzled clinicians for decades; 3. Is likely to impact the design of future clinical trials in which vitamin D insufficiency is redefined by decreased bioavailable vitamin D levels; 4. Advances the applicability of the 25[OH]D assay that has long been considered the gold-standard for determining vitamin D status and proposes a novel alternative (free/bioavailable D) that may solve perplexing inconsistencies in outcomes in different races that may be secondary to vitamin D status; 5, Advances a contemporary principle that diagnosis and treatment should be individualized based on, at least race and gender, to improve the therapeutic and cost-efficiency of limited health care resources.

Test Hypotheses in HANDLS Subjects.

Figure 5:
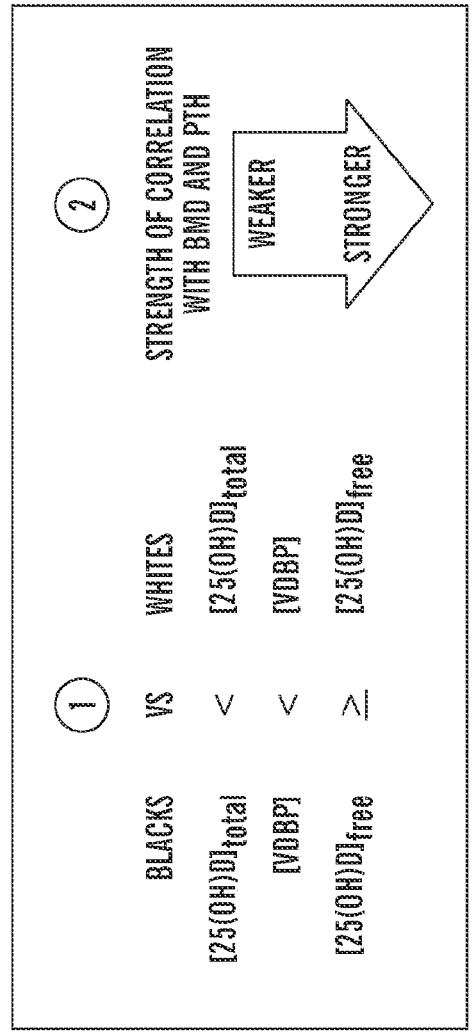
FIG. 5. Hypotheses tested in Example 4.

The hypotheses described below can be explored (FIG. 5) by measuring total 25(OH)D and VDBP levels in stored serum samples from black and white subjects with baseline BMD measurements enrolled in HANDLS:33 1. Blacks have lower levels of VDBP and total 25(OH)D levels, but similar levels of free and bioavailable25(OH)D as whites. 2. Free and bioavailable 25(OH)D levels are independently associated with BMD in blacks and whites, and are inversely and linearly associated with PTH levels, and the associations are stronger than those between total 25(OH)D and BMD.

Levels of free and bioavailable vitamin D can be calculated from total 25(OH)D, VDBP and serum albumin measurements as shown below.[38,70,76] Data will be examined using multivariate analyses for the presence of associations between BMD and free- and bioavailable 25(OH)D, and for associations between free- and bioavailable 25(OH)D and PTH in black vs white subjects. Adjustments for covariates such as: history of osteoporosis, age, sex, pre-menopausal status, smoking and alcohol use, oral vitamin D and calcium intake, use of bisphosphonates, exercise, and body mass index can be made.

The HANDLS Study.

The HANDLS study is being conducted as part of the National Institution of Aging Intramural Research Program (NIAIRP). Planned as a 20-year longitudinal study, HANDLS is designed to test hypotheses about aging and health disparities in minority and poor populations by evaluating differences in rates and risks for pathological conditions associated with aging within diverse racial, ethnic, and economic groups. Data on physical, genetic, biologic, demographic, psychosocial, and psychophysiological parameters from a fixed cohort of 3,722 black and white participants in higher and lower socioeconomic status are being collected.

Population being Studied.

HANDLS participants are a fixed cohort of community-dwelling black and white adults aged 30-64. Participants in HANDLS have been recruited from 12 pre-determined neighborhoods (groups of contiguous census tracts) comprising the geographic area of Baltimore city and South Baltimore. The population comprises a 4-way factorial cross of age (seven 5-year age bands between 30-64), sex, race, and socioeconomic status indexed by poverty status.

Variables Available.

The HANDLS database contains information obtained from household interviews of black and white participants about their health status, health service utilization, psychosocial factors, nutrition, neighborhood characteristics, and demographics. In addition, mobile medical research vehicles deployed every three years collect data (over ~20 years) from the same participants on: medical history and physical examination, dietary recall, cognitive evaluation, psychophysiology assessments including heart rate variability, arterial thickness, carotid ultrasonography, assessments of muscle strength and bone density, and laboratory measurements (blood chemistries, hematology, biomarkers of oxidative stress and biomaterials for genetic studies).

The serum levels of total 25(OH)D, VDBP, albumin, PTH can be examined and bioavailable 25(OH)D calculated in all HANDLS subjects with baseline BMD measurements (~2200). Associations between VDBP levels, total 25(OH)D, and PTH levels can be tested for. In addition to baseline assessments, 5 follow-up triennial assessments are being collected as part of HANDLS over ~20 years. At least one follow-up measure at Year 3 (and as many as possible for the duration of the funding period) for an exploratory evaluation of BMD and related outcomes (ie, osteoporosis, fractures).

Blood Available.

Approximately 2,200 participants of HANDLS have baseline BMD measurements and stored serum samples. Followup BMD data, and blood samples collected at Year 3 (and possibly Year 6 as funding allows) can be obtained to evaluate associations between BMD and related outcomes and total, bioavailable, and free 25(OH)D over time.

Analysis Techniques.

Stored serum samples from the HANDLS repository collected at baseline and at Years 3 and 6 (as feasible) can be used. Total 25(OH)D levels can be measured by high performance liquid chromatography/mass spectrophotometry. Albumin can be measured on standard automated platforms. VDBP can be measured using a commercially available ELISA (R&D Systems) as described in Example 1 herein. Interassay CVs and intra-assay CVs for this assay are 5.7% and 7.4% respectively.

In order to validate the calculated estimates of free 25(OH)D and test whether these methods are valid in both black and white subjects, free 25(OH)D can be measured directly in a subset of samples (n=200) as described previously.[82] Since blood sampling dates are captured, season can be included as a covariate in the modeling of vitamin D measurements.

The PTH assay can be performed using an electrochemiluminescence immunoassay "ECLIA" on the Cobas E601 analyzer (Roche diagnostics). The assay for determining intact PTH employs a sandwich test principle in which a biotinylated monoclonal antibody reacts with the N-terminal fragment (1-37) and a monoclonal antibody labeled with a ruthenium complex reacts with the C-terminal fragment (38-84). The test can performed using 300 μL of EDTA plasma, which provides more stable test results than serum.

Power Calculations.

To determine VDBP, total and bioavailable 25(OH)D, and PTH levels in black vs white subjects. Power was calculated assuming a 2-sided t-test with α=0.05 for differences in black vs white subjects for total 25(OH)D (primary variable of interest). Although no previous studies have explored this measure among different racial groups, bioavailable 25(OH)D is derived from total 25(OH)D and is a secondary variable of interest and it can constitute a reliable proxy. The weighted means and standard deviations were derived from 5 published reports[18,19,83-85] constituting a total of 14,402 whites and 7,790 blacks with clinical and demographic characteristics similar to what we expect from the HANDLS population (relatively healthy population, predominantly middle-aged). From these studies, an expected mean and standard deviation were derived for total 25(OH)D among whites and blacks (28.07±3.71 ng/mL and 17.88±12.28 ng/mL, respectively). The sample size of nearly 2,200 HANDLS subjects can be expected to be adequate to detect primary and secondary variables of interest with a power of 0.8, even with the possibility of invalid measurements and missing data (estimates at <5% of available observations).

To Test for Associations Between BMD, Bioavailable 25(OH)D, and PTH Compared to Total 25(OH)D in Black Vs White Subjects.

To obtain estimates for whole body BMD, a random sample of 40 subjects, stratified by race, was selected from all available HANDLS subjects with non-missing whole body BMD and total 25(OH)D measurements. Power was calculated assuming a 2-sided p-value with o=0.05. Based on preliminary analysis, r=0.29 between total 25(OH)D and whole body BMD in whites and r=0.24 among blacks was obtained. Assuming a correlation between bioavailable 25(OH)D and whole body BMD to be ~30% higher, based on findings from the MACS study, 23 the linear relation between these variables can be approximated to be r=0.38 among whites and r=0.31 among blacks. Based on these estimates, the reduced $R^2$ among whites and blacks ($R^2$=0.14 and R2=0.10, respectively) for multiple linear regression analyses was calculated. The sample size of nearly 2,200 HANDLS subjects is adequate to detect the primary and secondary variables of interest with a power of 0.8, even with the possibility of invalid measurements and missing data (estimates at <5% of available observations).

Statistical Analysis

Preliminary examination of VDBP, total, bioavailable 25(OH)D, and PTH levels include assessment of the plausibility of values through observed ranges. Measures of central tendency and dispersion can be documented. As initial examination of VDBP, total, bioavailable 25(OH)D, and PTH levels have shown highly, right-skewed distributions, these variables can be assessed for normality through use of visualization techniques such as quantile-quantile plots and testing by Shapiro-Wilkes tests both for the overall sample and stratified by race. If VDBP, total, bioavailable 25(OH)D, and PTH levels are found to be normally distributed, mean levels between black and white subjects can be compared through the use of two-samples t-tests. Otherwise, the distributions between black and white subjects will be compared through the use of nonparametric statistics such as Wilcoxon rank sum tests. Two-tailed p-values of <0.05 will be considered statistically significant.

BMD can be preliminarily be examined for plausibility of values and measures of central tendency and dispersion will be documented. The distribution of BMD can be inspected both through visualization and through formal statistical testing. Exploratory data analysis can be performed through the use of scatterplots to inspect the relationship between BMD, total 25(OH)D, bioavailable 25(OH)D, and PTH. If a linear relationship is found between variables, Pearson Product-Moment Correlation Coefficient or Spearman's Rank Correlation Coefficient (in the case of outliers) can be used to examine associations between BMD, total 25(OH)D, bioavailable 25(OH)D, and PTH. Based on the strength of the relationships found between bioavailable 25(OH)D, total 25(OH)D, and PTH and BMD, multivariable linear regression models can be constructed to determine the independent association of bioavailable 25(OH)D, total 25(OH)D, and PTH to BMD adjusting for other covariates, including history of osteoporosis, age, sex, pre-menopausal status, smoking and alcohol use, oral vitamin D and calcium intake, use of bisphosphonates, exercise, and body mass index. Seasonality can be explored in all models by controlling for month of data collection and if seasonality is found, a cyclic regression curve can be included in the models.

The relationships between covariates and BMD, vitamin D levels, and PTH can be explored through the use of independent samples t-tests (for binary covariates) and simple linear regression (for continuous covariates) as well as through visualization techniques including boxplots and scatterplot matrices. Predictive variables can be selected through the use of Least Angle Regression (LAR)[86] or Least Absolute Shrinkage and Selection Operator (LASSO)[87] since both have proved to be more reliable than the traditional stepwise variable selection method. Covariates central to our hypotheses or that have been shown in previous literature to be clinically relevant to 25(OH)D, total 25(OH)D, and PTH and BMD can be left in the models irrespective of selection. Model assessment can be performed through a variety of procedures. Collinearity can be assessed through correlations between covariates and the variance inflation factor (VIF). Residuals can be examined through standardized residual plots and normality can be tested by Shapiro-Wilk tests. Component plus residual plots will provide a means to investigate the linearity between continuous predictors with BMD controlling for the effects of other predictors in the model. The degree of overlap between LOESS curves and the regression line can be used to assess linearity of the predictors. Diagnostics of influential data points can be identified through Cook's distances (D) where observations with (Di>4/n) will be suspected of influence. A jack-knife approach can be used to compare models with and without influential observations and the percentage of error attributed to individual observations can be documented. Observations with high Cook's distances but biologically plausible values can be considered for inclusion in the final models. The final candidates of models can be compared for Akaike Information Criterion (AIC) value as well as adjusted Rsquared value.

Inclusion and formal testing of interactions between all covariates, with special attention paid to the interaction between race and socioeconomic status, can be incorporated into un-stratified multivariable models. Nonsignificant interaction terms can be dropped from final models. Significant interaction terms can be visually inspected through the use of Trellis graphs and the associations between covariates and BMD can be interpreted according to the level of the interactive predictor. Multivariable models cam be conducted stratified by race and will be analyzed in a similar manner with the exclusion of interaction terms including race.

As CVD has been linked to 25(OH)D status, exploratory analyses can be performed using available data to detect any relationships between bioavailable, total 25(OH)D, and PTH and carotid intimal medial thickness and blood pressure at baseline.

REFERENCES

For Example 4 and the Background of Invention Sections

1. Cauley J A, Lacroix A Z, Wu L, et al. Serum 25-hydroxyvitamin D concentrations and risk for hip fractures. Ann Intern Med 2008; 149:242-50.
2. Judd S E, Tangpricha V. Vitamin D deficiency and risk for cardiovascular disease. Am J Med Sci 2009; 338:40-4.
3. Martins D, Wolf M, Pan D, et al. Prevalence of cardiovascular risk factors and the serum levels of 25-hydroxyvitamin D in the United States: data from the Third National Health and Nutrition Examination Survey. Arch Intern Med 2007; 167:1159-65.
4. Wang T J, Pencina M J, Booth S L, et al. Vitamin D deficiency and risk of cardiovascular disease. Circulation 2008; 117:503-11.
5. Zittermann A, Schleithoff S S, Tenderich G, Berthold H K, Korfer R, Stehle P. Low vitamin D status: a contributing factor in the pathogenesis of congestive heart failure? J Am Coll Cardiol 2003; 41:105-12.
6. Ooms M E, Roos J C, Bezemer P D, van der Vijgh W J, Bouter L M, Lips P. Prevention of bone loss by vitamin D supplementation in elderly women: a randomized double-blind trial. J Clin Endocrinol Metab 1995; 80:1052-8.
7. Dawson-Hughes B, Harris S S, Krall E A, Dallal G E. Effect of calcium and vitamin D supplementation on bone density in men and women 65 years of age or older. N Engl J Med 1997; 337:670-6.
8. Dawson-Hughes B, Harris S S, Krall E A, Dallal G E, Falconer G, Green C L. Rates of bone loss in postmenopausal women randomly assigned to one of two dosages of vitamin D. Am J Clin Nutr 1995; 61:1140-5.
9. Jackson R D, LaCroix A Z, Gass M, et al. Calcium plus vitamin D supplementation and the risk of fractures. N Engl J Med 2006; 354:669-83.
10. Bischoff-Ferrari H A, Willett W C, Wong J B, Giovannucci E, Dietrich T, Dawson-Hughes B. Fracture prevention with vitamin D supplementation: a meta-analysis of randomized controlled trials. JAMA 2005; 293:2257-64.
11. Bischoff-Ferrari H A, Willett W C, Wong J B, et al. Prevention of nonvertebral fractures with oral vitamin D and dose dependency: a meta-analysis of randomized controlled trials. Arch Intern Med 2009; 169:551-61.
12. Chapuy M C, Arlot M E, Duboeuf F, et al. Vitamin D3 and calcium to prevent hip fractures in the elderly women. N Engl J Med 1992; 327:1637-42.
13. Wang L, Manson J E, Song Y, Sesso H D. Systematic review: Vitamin D and calcium supplementation in prevention of cardiovascular events. Ann Intern Med 2010; 152:315-23.
14. Autier P, Gandini S Vitamin D supplementation and total mortality: a meta-analysis of randomized controlled trials. Arch Intern Med 2007; 167:1730-7.
15. Fiscella K, Franks P. Vitamin D, race, and cardiovascular mortality: findings from a national US sample. Ann Fam Med 2010; 8:11-8.
16. Harris S S. Vitamin D and African Americans. J Nutr 2006; 136:1126-9.
17. Orwoll E, Nielson C M, Marshall L M, et al. Vitamin D deficiency in older men. J Clin Endocrinol Metab 2009; 94:1214-22.
18. Bischoff-Ferrari H A, Dietrich T, Orav E J, Dawson-Hughes B. Positive association between 25-hydroxyvitamin D levels and bone mineral density: a population-based study of younger and older adults. Am J Med 2004; 116:634-9.
19. Hannan M T, Litman H J, Araujo A B, et al. Serum 25-hydroxyvitamin D and bone mineral density in a racially and ethnically diverse group of men. J Clin Endocrinol Metab 2008; 93:40-6.
20. Cauley J A, Lui L Y, Ensrud K E, et al. Bone mineral density and the risk of incident nonspinal fractures in black and white women. JAMA 2005; 293:2102-8.

21. Thacher T D, Clarke B L. Vitamin D insufficiency. Mayo Clin Proc 2011; 86:50-60.
22. Gutierrez O M, Farwell W R, Kermah D, Taylor E N. Racial differences in the relationship between vitamin D, bone mineral density, and parathyroid hormone in the National Health and Nutrition Examination Survey. Osteoporos Int 2010; E-Pub ahead of print.
23. Powe C E, Ricciardi C, Berg A H, et al. Vitamin D-binding protein modifies the vitamin D-bone mineral density relationship. J Bone Miner Res 2011; 26:1609-16.
24. Al-oanzi Z H, Tuck S P, Raj N, et al. Assessment of vitamin D status in male osteoporosis. Clin Chem 2006; 52:248-54.
25. Lauridsen A L, Vestergaard P, Hermann A P, et al. Plasma concentrations of 25-hydroxy-vitamin D and 1,25-dihydroxy-vitamin D are related to the phenotype of Gc (vitamin D-binding protein): a cross-sectional study on 595 early postmenopausal women. Calcif Tissue Int 2005; 77:15-22.
26. Sinotte M, Diorio C, Berube S, Pollak M, Brisson J. Genetic polymorphisms of the vitamin D binding protein and plasma concentrations of 25-hydroxyvitamin D in premenopausal women. Am J Clin Nutr 2009; 89:634-40.
27. Constans J, Hazout S, Garruto R M, Gajdusek D C, Spees E K. Population distribution of the human vitamin D binding protein: anthropological considerations. Am J Phys Anthropol 1985; 68:107-22.
28. Fang Y, van Meurs J B, Arp P, et al. Vitamin D binding protein genotype and osteoporosis. Calcif Tissue Int 2009; 85:85-93.
29. Papiha S S, Allcroft L C, Kanan R M, Francis R M, Datta H K. Vitamin D binding protein gene in male osteoporosis: association of plasma DBP and bone mineral density with (TAAA)(n)-Alu polymorphism in DBP. Calcif Tissue Int 1999; 65:262-6.
30. Wang T J, Zhang F, Richards J B, et al. Common genetic determinants of vitamin D insufficiency: a genome-wide association study. Lancet 2010; 376:180-8.
31. Powe C E K S, Pham J L, Ye J, Ankers E D, Ricciardi C E, Thadhani R, Bhan I. Vitamin D Binding Protein Modifies Relationship between Vitamin D and Calcium in Dialysis. In: American Society of Nephrology Annual Meeting; Denver, Colo.; November 2010.
32. Powe C E. Vitamin D Binding Protein as a Modifier of Vitamin D Activity in Humans [MD Honors]. Cambridge: Harvard; 2011.
33. Institute of Medicine. Dietary Reference Intakes for Calcium and Vitamin D. In: http://www.iom.edu/~/media/Files/Report %20Files/2010/Dietary-Reference-Intakes-for-Calcium-and-Vitamin-D/Vitamin %20D %20 and %20Calcium %202010%20Report %20Brief.pdf, ed.; November 2010:1-4.
34. Holick M F. Vitamin D deficiency. N Engl J Med 2007; 357:266-81.
35. O'Riordan J L. Rickets in the 17th Century. Journal of Bone and Mineral Research 2006; 21:1506-10.
36. Gloth F M, 3rd, Gundberg C M, Hollis B W, Haddad J G, Jr., Tobin J D. Vitamin D deficiency in homebound elderly persons. Jama 1995; 274:1683-6.
37. Compher C W, Badellino K O, Boullata J I. Vitamin D and the bariatric surgical patient: a review. Obes Surg 2008; 18:220-4.
38. Bikle D D, Siiteri P K, Ryzen E, Haddad J G. Serum protein binding of 1,25-dihydroxyvitamin D: a reevaluation by direct measurement of free metabolite levels. J Clin Endocrinol Metab 1985; 61:969-75.
39. Matsuoka L Y, Ide L, Wortsman J, MacLaughlin J A, Holick M F. Sunscreens suppress cutaneous vitamin D3 synthesis. J Clin Endocrinol Metab 1987; 64:1165-8.
40. Thomas M K, Lloyd-Jones D M, Thadhani R I, et al. Hypovitaminosis D in medical inpatients. N Engl J Med 1998; 338:777-83.
41. Hamilton S A, McNeil R, Hollis B W, et al. Profound Vitamin D Deficiency in a Diverse Group of Women during Pregnancy Living in a Sun-Rich Environment at Latitude 32 degrees N. Int J Endocrinol 2010; 2010:917428.
42. Tangpricha V, Pearce E N, Chen T C, Holick M F. Vitamin D insufficiency among free-living healthy young adults. Am J Med 2002; 112:659-62.
43. Wolf M, Shah A, Gutierrez O, et al. Vitamin D levels and early mortality among incident hemodialysis patients. Kidney Int 2007; 72:1004-13.
44. Merewood A, Mehta S D, Grossman X, et al. Widespread vitamin D deficiency in urban Massachusetts newborns and their mothers. Pediatrics 2010; 125:640-7.
45. Wortsman J, Matsuoka L Y, Chen T C, Lu Z, Holick M F. Decreased bioavailability of vitamin D in obesity. Am J Clin Nutr 2000; 72:690-3.
46. Holick M F. MrOs is D-ficient. J Clin Endocrinol Metab 2009; 94:1092-3.
47. Vieth R, Bischoff-Ferrari H, Boucher B J, et al. The urgent need to recommend an intake of vitamin D that is effective. Am J Clin Nutr 2007; 85:649-50.
48. Holick M F. Sunlight and vitamin D for bone health and prevention of autoimmune diseases, cancers, and cardiovascular disease. Am J Clin Nutr 2004; 80:16785-885.
49. Nesby-O'Dell S, Scanlon K S, Cogswell M E, et al. Hypovitaminosis D prevalence and determinants among African American and white women of reproductive age: third National Health and Nutrition Examination Survey, 1988-1994. Am J Clin Nutr 2002; 76:187-92.
50. Harris S S, Dawson-Hughes B. Seasonal changes in plasma 25-hydroxyvitamin D concentrations of young American black and white women. Am J Clin Nutr 1998; 67:1232-6.
51. Diaz V A, Mainous A G, 3rd, Carek P J, Wessell A M, Everett C J. The association of vitamin D deficiency and insufficiency with diabetic nephropathy: implications for health disparities. J Am Board Fam Med 2009; 22:521-7.
52. Matsuoka L Y, Wortsman J, Chen T C, Holick M F. Compensation for the interracial variance in the cutaneous synthesis of vitamin D. J Lab Clin Med 1995; 126:452-7.
53. Wolf M, Betancourt J, Chang Y, et al. Impact of activated vitamin D and race on survival among hemodialysis patients. J Am Soc Nephrol 2008; 19:1379-88.
54. Bischoff-Ferrari H A, Giovannucci E, Willett W C, Dietrich T, Dawson-Hughes B. Estimation of optimal serum concentrations of 25-hydroxyvitamin D for multiple health outcomes. Am J Clin Nutr 2006; 84:18-28.
55. Parfitt A M. Osteomalacia and related disorders In: Avioli L V, Krane, S. M., ed. Metabolic bone disease. 3rd ed. San Diego, Calif.: Academic Press; 1998:327-86.
56. Sahota O. Osteoporosis and the role of vitamin D and calcium-vitamin D deficiency, vitamin D insufficiency and vitamin D sufficiency. Age Ageing 2000; 29:301-4.
57. Morris H A, Anderson P H. Autocrine and paracrine actions of vitamin D. Clin Biochem Rev 2010; 31:129-38.
58. Karagas M R, Lu-Yao G L, Barrett J A, Beach M L, Baron J A. Heterogeneity of hip fracture: age, race, sex, and geographic patterns of femoral neck and trochanteric fractures among the US elderly. Am J Epidemiol 1996; 143: 677-82.

59. Barrett J A, Baron J A, Karagas M R, Beach M L. Fracture risk in the U.S. Medicare population. J Clin Epidemiol 1999; 52:243-9.
60. Breslau N A. Normal and abnormal regulation of 1,25-(OH)2D synthesis. Am J Med Sci 1988; 296:417-25.
61. Need A G, Horowitz M, Morris H A, Nordin B C. Vitamin D status: effects on parathyroid hormone and 1,25-dihydroxyvitamin D in postmenopausal women. Am J Clin Nutr 2000; 71:1577-81.
62. Aloia J F, Chen D G, Chen H. The 25(OH)D/PTH threshold in black women. J Clin Endocrinol Metab 2010; 95:5069-73.
63. Braun A, Bichlmaier R, Cleve H. Molecular analysis of the gene for the human vitamin-D-binding protein (group-specific component): allelic differences of the common genetic GC types. Hum Genet 1992; 89:401-6.
64. Al-oanzi Z H, Tuck S P, Mastana S S, et al. Vitamin D-binding protein gene microsatellite polymorphism influences BMD and risk of fractures in men. Osteoporos Int 2008; 19:951-60.
65. Anderson L N, Cotterchio M, Cole D E, Knight J A. Vitamin D-Related Genetic Variants, Interactions with Vitamin D Exposure and Breast Cancer Risk among Caucasian Women in Ontario. Cancer Epidemiol Biomarkers Prev 2011.
66. Safadi F F, Thornton P, Magiera H, et al. Osteopathy and resistance to vitamin D toxicity in mice null for vitamin D binding protein. J Clin Invest 1999; 103:239-51.
67. Noren Hooten N, Abdelmohsen K, Gorospe M, Ejiogu N, Zonderman A B, Evans M K. microRNA expression patterns reveal differential expression of target genes with age. PLoS One 2010; 5:e10724.
68. Smith J G, Magnani J W, Palmer C, et al. Genome-Wide Association Studies of the PR Interval in African Americans. PLoS Genet 2011; 7:EPub: e1001304.
69. Mendel C M. The free hormone hypothesis: a physiologically based mathematical model. Endocr Rev 1989; 10:232-74.
70. Bikle D D, Gee E, Halloran B, Kowalski M A, Ryzen E, Haddad J G. Assessment of the free fraction of 25-hydroxyvitamin D in serum and its regulation by albumin and the vitamin D-binding protein. J Clin Endocrinol Metab 1986; 63:954-9.
71. Arnaud J, Constans J. Affinity differences for vitamin D metabolites associated with the genetic isoforms of the human serum carrier protein (DBP). Hum Genet 1993; 92:183-8.
72. Leheste J R, Melsen F, Wellner M, et al. Hypocalcemia and osteopathy in mice with kidney-specific megalin gene defect. FASEB J 2003; 17:247-9.
73. Zella L A, Shevde N K, Hollis B W, Cooke N E, Pike J W. Vitamin D-binding protein influences total circulating levels of 1,25-dihydroxyvitamin D3 but does not directly modulate the bioactive levels of the hormone in vivo. Endocrinology 2008; 149:3656-67.
74. Chun R F, Lauridsen A L, Suon L, et al. Vitamin D-binding protein directs monocyte responses to 25-hydroxy- and 1,25-dihydroxyvitamin D. J Clin Endocrinol Metab 2010; 95:3368-76.
75. Braunstein G D. In: Basic & Clinical Endocrinology. 5th ed. Stamford, Conn.: Appleton & Lange; 1997:422-452.
76. Vermeulen A, Verdonck L, Kaufman J M. A critical evaluation of simple methods for the estimation of free testosterone in serum. J Clin Endocrinol Metab 1999; 84:3666-72.
77. Emadi-Konjin P, Bain J, Bromberg I L. Evaluation of an algorithm for calculation of serum "bioavailable" testosterone (BAT). Clin Biochem 2003; 36:591-6.
78. Nykjaer A, Fyfe J C, Kozyraki R, et al. Cubilin dysfunction causes abnormal metabolism of the steroid hormone 25(OH) vitamin D(3). Proc Natl Acad Sci USA 2001; 98:13895-900.
79. Amsellem S, Gburek J, Hamard G, et al. Cubilin is essential for albumin reabsorption in the renal proximal tubule. J Am Soc Nephrol 2010; 21:1859-67.
80. Russo L M, Sandoval R M, McKee M, et al. The normal kidney filters nephrotic levels of albumin retrieved by proximal tubule cells: retrieval is disrupted in nephrotic states. Kidney Int 2007; 71:504-13.
81. Russo D, Corrao S, Miranda I, et al. Progression of coronary artery calcification in predialysis patients. Am J Nephrol 2007; 27:152-8.
82. van Hoof H J, Swinkels L M, Ross H A, Sweep C G, Benraad T J. Determination of non-protein-bound plasma 1,25-dihydroxyvitamin D by symmetric (rate) dialysis. Anal Biochem 1998; 258:176-83.
83. Gutierrez O M, Farwell W R, Kermah D, Taylor E N. Racial differences in the relationship between vitamin D, bone mineral density, and parathyroid hormone in the National Health and Nutrition Examination Survey. Osteoporos Int 2011; 22:1745-53.
84. Reis J P, Michos E D, von Muhlen D, Miller E R, 3rd. Differences in vitamin D status as a possible contributor to the racial disparity in peripheral arterial disease. Am J Clin Nutr 2008; 88:1469-77.
85. Cauley J A, Danielson M E, Boudreau R, et al. Serum 25 hydroxyvitamin (OH)D and clinical fracture risk in a multiethnic Cohort of women: The Women's health initiative (WHI). J Bone Miner Res 2011.
86. Efron B, Hastie T, Johnstone I, Tibshirani R. Least angle regression. Ann Stat 2004; 32:407-99.
87. Tibrishani R. Regression shrinkage and section via the lasso. J Royal Stat Soc 1996; 58:267-88.
88. Wolf M, Sandler L, Munoz K, Hsu K, Ecker J L, Thadhani R. First trimester insulin resistance and subsequent preeclampsia: a prospective study. J Clin Endocrinol Metab 2002; 87:1563-8.

TABLE 1

Characteristics of the Study Population (n = 49).
Data are presented as n (%) for categorical variables
and mean ± standard deviation for continuous variables.

|  | Mean ± SD n (%) |
|---|---|
| Age (years) | 23.5 ± 3.4 |
| Body Mass Index (kg/m$^2$) | 22.43 ± 2.96 |
| Sex |  |
| Male | 27 (55.1%) |
| Female | 22 (44.9%) |
| Race |  |
| White | 31 (63.3%) |
| Non-White | 18 (36.7%) |
| Exercise Amount |  |
| >120 minutes per week | 21 (42.9%) |
| ≤120 minutes per week | 26 (53.1%) |
| Unknown | 2 (4.1%) |
| Vitamin D Binding Protein (umol/L) | 4.19 ± 2.49 |
| Albumin (g/L) | 42.47 ± 3.94 |
| Serum Calcium (mmol/L) | 2.30 ± 0.19 |
| Parathyroid Hormone (ng/L) | 29.86 ± 8.25 |
| Dietary Calcium Intake (mg/day) | 925.85 ± 421.76 |
| Lumbar Spine Bone Mineral Density (g/cm$^2$) | 1.05 ± 0.14 |

TABLE 2

Serum Levels of Vitamin D. Total 25(OH)D levels were measured along with albumin and vitamin D binding protein (DBP). DBP-bound, albumin-bound, free, and bioavailable 25(OH)D (free and albumin bound) were calculated

|  | Mean ± SD |
|---|---|
| Total 25(OH)D (nmol/L) | 64.23 ± 27.70 |
| DBP-Bound 25(OH)D (nmol/L) | 54.66 ± 26.32 |
| Albumin-Bound 25(OH)D (nmol/L) | 9.55 ± 6.72 |
| Free 25(OH)D (pmol/L) | 25.37 ± 18.52 |
| Bioavailable 25(OH)D (nmol/L) | 9.58 ± 6.74 |

TABLE 3

Bone Mineral Density, DBP Levels, and 25(OH)D Levels in Select Subgroups. Values are reported as mean ± standard deviation. DBP = vitamin D binding protein. BMD = bone mineral density. OCP = oral contraceptive pill. Groups were compared using t-tests after natural log transformation of total 25(OH)D, DBP, bioavailable 25(OH)D levels and BMD.

|  | n | Total 25(OH)D (nmol/L) | Total DBP (umol/L) | Bioavailable 25(OH)D (nmol/L) | L-Spine BMD (g/cm$^2$) |
|---|---|---|---|---|---|
| Sex | | | | | |
| Male | 27 | 52.79 ± 19.31 | 3.90 ± 2.09 | 8.36 ± 5.36 | 1.04 ± 0.14 |
| Female | 22 | 78.28 ± 30.28 | 4.53 ± 2.92 | 11.08 ± 8.01 | 1.07 ± 0.13 |
| p-value | | <0.001 | 0.493 | 0.113 | 0.371 |
| OCP Use (Females Only) | | | | | |
| Yes | 7 | 107.33 ± 27.87 | 6.27 ± 3.76 | 12.83 ± 11.64 | 1.06 ± 0.21 |
| No | 15 | 64.73 ± 20.59 | 3.71 ± 2.12 | 10.26 ± 5.98 | 1.07 ± 0.08 |
| p-value | | <0.001 | 0.152 | 0.841 | 0.646 |
| Body Mass Index | | | | | |
| <25 kg/m$^2$ | 39 | 66.0 ± 26.9 | 4.63 ± 2.49 | 8.59 ± 5.28 | 1.04 ± 0.12 |
| ≥25 kg/m$^2$ | 10 | 57.2 ± 25.0 | 2.42 ± 1.61 | 13.43 ± 10.19 | 1.09 ± 0.19 |
| p-value | | 0.284 | 0.003 | 0.073 | 0.438 |
| Exercise | | | | | |
| ≥120 Minutes/Week | 21 | 73.33 ± 26.11 | 4.14 ± 2.56 | 11.76 ± 8.35 | 1.09 ± 0.13 |
| <120 Minutes/Week | 26 | 58.66 ± 27.97 | 4.20 ± 2.58 | 8.19 ± 4.85 | 1.03 ± 0.13 |
| p-value | | 0.038 | 0.863 | 0.089 | 0.165 |
| Race | | | | | |
| White | 31 | 68.84 ± 28.65 | 4.94 ± 2.43 | 7.84 ± 3.92 | 1.03 ± 0.10 |
| Non-White | 18 | 56.30 ± 24.76 | 2.87 ± 2.04 | 12.56 ± 9.29 | 1.08 ± 0.18 |
| p-value | | 0.138 | <0.001 | 0.065 | 0.346 |

TABLE 4

Bioavailable 25(OH)D Predicts Bone Mineral Density (BMD). Bioavailable 25(OH)D and BMD were natural log transformed prior to analysis. The coefficient (B) represents the average unit increase in ln BMD for each unit increase in ln bioavailable 25(OH)D. P-value is the statistical significance of the relationship between bioavailable 25(OH)D and BMD after controlling for potential confounders. Thus, the relationship between bioavailable 25(OH)D and BMD remains significant after adjusting for potential confounders.

| Model | B | P-value | Adjusted R$^2$ |
|---|---|---|---|
| Bioavailable 25(OH)D | 0.092 | 0.002 | 0.177 |
| Bioavailable 25(OH)D, age, sex, race, and BMI | 0.072 | 0.029 | 0.180 |

TABLE 5

Characteristics of the population (n = 94)

|  | Median (IQR) or n (%) |
|---|---|
| Age, years | 65 (50-74) |
| Male | 55 (59%) |
| Black race | 48 (51%) |
| Survived at least one year on dialysis | 47 (50%) |
| Body mass index | 25 (22-30) |
| Systolic blood pressure, mm Hg | 140 (123-153) |
| Diastolic blood pressure, mm Hg | 73 (61-81) |

TABLE 5-continued

Characteristics of the population (n = 94)

|  | Median (IQR) or n (%) |
|---|---|
| Total 25(OH)D, ng/ml | 20 (13-28) |
| Total 1.25(OH)$_2$D, ng/ml | 9.5 (5-16) |
| Parathyroid hormone, pg/ml | 190 (96-307) |
| Corrected Calcium, mg/dl | 8.9 (8.5-9.4) |
| Phosphorus, mg/dl | 4.2 (3-5.5) |
| Alkaline phosphatase, mg/dl | 82 (66-112.5) |
| Albumin, g/dl | 3.4 (3.0-3.8) |
| Vitamin D binding protein, μg/ml | 158 (69-217) |
| Bioavailable 25(OH)D, ng/ml | 3.4 (2.2-5.0) |
| Bioavailable 1.25(OH)$_2$D, pg/ml | 2.2 (1.1-3.8) |

TABLE 6

Race and vitamin D levels. Black individuals had lower total, but not bioavailable, 25(OH)D levels when compared with their white counterparts. Survivors are patients who survived for at least one year after initiating hemodialysis, while non-survivors died within this year. All values represent group medians.

|  | Blacks | Whites | p |
|---|---|---|---|
| Total 25(OH)D (ng/ml) | 15.1 | 23.1 | <0.001 |
| Bioavailable 25(OH)D (ng/ml) | 3.8 | 2.8 | 0.21 |
| Total 1.25(OH)$_2$D (pg/ml) | 8 | 11.5 | 0.07 |
| Bioavailable 1.25(OH)$_2$D (pg/ml) | 2.2 | 2.2 | 0.48 |
| DBP (μg/ml) | 75 | 189 | <0.001 |
| Survivors: DBP (μg/ml) | 88 | 195 | 0.004 |
| Non-survivors: DBP (μg/ml) | 58 | 183 | <0.001 |
| PTH (pg/ml) | 201 | 168 | 0.47 |

TABLE 7

PTH and bioavailable 25(OH) vitamin D. In univariate and multivariate analyses, bioavailable 25(OH) vitamin D levels were consistently associated with PTH (corresponding p values displayed). PTH and bioavailable vitamin D levels were log transformed prior to analysis, thus β = −0.36 suggests that a 25% increase in bioavailable 25(OH)D is associated with 7.7% decrease in PTH $((1.25^{-0.36} - 1)*100 = -7.7)$.

|  | β | p |
|---|---|---|
| Bioavailable 25(OH)D alone | −0.36 | 0.007 |
| Multivariate model adding age, gender, race | −0.33 | 0.02 |
| Multivariate model with above variables plus survival status at 1 year | −0.32 | 0.02 |
| Multivariate model with above variables plus calcium, phosphorus, bioavailable 1.25(OH)$_2$D | −0.39 | 0.02 |

TABLE 8

Calculation of bioavailable vitamin D levels

| Number | Equation |
|---|---|
| 1 | $[D_{DBP}] = [\text{Total Vitamin D}] - [D_{Alb}] - [D_{free}]$ |
| 2 | $[D_{Alb}] = K_{alb} \cdot [\text{Alb}] \cdot [D_{free}]$ |
| 3 | $[D_{free}] = [D_{DBP}] \div K_{DBP} \div [DBP_{free}]$ |
| 4 | $[DBP_{free}] = [\text{Total DBP}] - [D_{DBP}]$ |
| From equations 3 and 4 | |
| 5 | $[D_{free}] = [D_{DBP}] \div K_{DBP} \div ([\text{Total DBP}] - [D_{DBP}])$ |
| From equations 1 and 2 | |
| 6 | $[D_{DBP}] = [\text{Total Vitamin D}] - (K_{alb} \cdot [\text{Alb}] + 1) \cdot [D_{free}]$ |
| 7 | $[D_{free}] = \{[\text{Total Vitamin D}] - (K_{alb} \cdot [\text{Alb}] + 1) \cdot [D_{free}]\} \div K_{DBP} \div ([\text{Total DBP}] - \{[\text{Total Vitamin D}] - (K_{alb} \cdot [\text{Alb}] + 1) \cdot [D_{free}]\})$ |

This can be simplified to fit a second-degree polynomial ($ax^2 + bx + c = 0$) where $x = [D_{free}]$:

$a = K_{DBP} \cdot K_{alb} \cdot [\text{Alb}] + K_{DBP}$
$b = K_{DBP} \cdot [\text{Total DBP}] - K_{DBP} \cdot [\text{Total Vitamin D}] + K_{alb} \cdot [\text{Alb}] + 1$
$c = -[\text{Total Vitamin D}]$

| 8 | $[D_{free}] = [-b + \sqrt{b^2 - 4ac}] \div 2a$ |
|---|---|
| 9 | $[D_{bioavailable}] = [D_{free}] + [D_{Alb}] = (K_{alb} \cdot [\text{Alb}] + 1) \cdot [D_{free}]$ |

[Total Vitamin D] = total measured vitamin D concentration (either 25-OH or 1.25-(OH)$_2$ vitamin D)
[Alb] = measured albumin concentration
[Total DBP] = measured vitamin D binding protein concentration
[D$_{Alb}$] = concentration of albumin-bound vitamin D
[D$_{DBP}$] = concentration of DBP-bound vitamin D
[D$_{free}$] = concentration of free (unbound) D
[D$_{bioavailable}$] = concentration of Bioavailable D = [D$_{free}$] + [D$_{Alb}$]
$K_{alb}$ = affinity constant between vitamin D and albumin = $6 \times 10^5 M^{-1}$ (for 25-OH D) or $5.4 \times 10^4 M^{-1}$ (for 1.25-(OH)$_2$ D)
$K_{DBP}$ = affinity constant between vitamin D and DBF = $7 \times 10^8 M^{-1}$ (for 25-OH D) or $3.7 \times 10^7 M^{-1}$ (for 1.25-(OH)$_2$ D)

TABLE 9

Comparison of 25(OH)D insufficiency in blacks vs. whites based on current definitions

| Population | Age (years) | % 25(OH)D Deficient Blacks | % 25(OH)D Deficient Whites | 25(OH)D Cutoff Levels | Reference |
|---|---|---|---|---|---|
| NHANES 2001-2006 | >45 (82-85%) | 80 | 40 | <20 ng/mL | Diaz[51] |
| Older men (MrOS) | >65 | 65 | 23 | <20 ng/mL | Orwoll[17] |
|  |  | 22 | 2 | <10 ng/mL |  |
| Hemodialysis patients (ArMORR) | 63 ± 15 | 31 | 12 | <10 ng/mL | Wolf[43] |
| Men in BACH/Bone Survey | 30-79 | 44 | 11 | <21 ng/mL | Hannan[19] |

NHANES = National Health and Nutrition Examination Survey;
MrOS = Osteoporotic Fractures in Men Study;
ArMORR = Accelerated Mortality on Renal Replacement;
BACH = Boston Area Community Health

SEQUENCE LISTING

SEQ ID NO: 01 Human VDBP Isoform 1, variant 1 NCBI Ref: NP_000574
```
  1  mkrvlvllla vafghalerg rdyeknkvck efshlgkedf tslslvlysr kfpsgtfeqv
 61  sqlvkevvsl teaccaegad pdcydtrtsa lsakscesns pfpvhpgtae cctkeglerk
121  lcmaalkhqp qefptyvept ndeiceafrk dpkeyanqfm weystnygqa plsllvsytk
181  sylsmvgscc tsasptvcfl kerlqlkhls llttlsnrvc sqyaaygekk srlsnlikla
241  qkvptadled vlplaeditn ilskccesas edcmakelpe htvklcdnls tknskfedcc
301  qektamdvfv ctyfmpaaql pelpdvelpt nkdvcdpgnt kvmdkytfel srrthlpevf
361  lskvleptlk slgeccdved sttcfnakgp llkkelssfi dkgqelcady sentfteykk
421  klaerlkakl pdatptelak lvnkhsdfas nccsinsppl ycdseidael knil
```

SEQ ID NO: 02 Human VDBP Isoform 1, variant 2 NCBI Ref: NP_001191235
```
  1  mkrvlvllla vafghalerg rdyeknkvck efshlgkedf tslslvlysr kfpsgtfeqv
 61  sqlvkevvsl teaccaegad pdcydtrtsa lsakscesns pfpvhpgtae cctkeglerk
121  lcmaalkhqp qefptyvept ndeiceafrk dpkeyanqfm weystnygqa plsllvsytk
181  sylsmvgscc tsasptvcfl kerlqlkhls llttlsnrvc sqyaaygekk srlsnlikla
241  qkvptadled vlplaeditn ilskccesas edcmakelpe htvklcdnls tknskfedcc
301  qektamdvfv ctyfmpaaql pelpdvelpt nkdvcdpgnt kvmdkytfel srrthlpevf
361  lskvleptlk slgeccdved sttcfnakgp llkkelssfi dkgqelcady sentfteykk
421  klaerlkakl pdatptelak lvnkhsdfas nccsinsppl ycdseidael knil
```

SEQ ID NO: 03 Human VDBP Isoform 2 NCBI Ref: NP_001191236
```
  1  mlwswseerg gaarlsgrkm krvlvlllav afghalergr dyeknkvcke fshlgkedft
 61  slslvlysrk fpsgtfeqvs qlvkevvslt eaccaegadp dcydtrtsal sakscesnsp
121  fpvhpgtaec ctkeglerkl cmaalkhqpq efptyveptn deiceafrkd pkeyanqfmw
181  eystnygqap lsllvsytks ylsmvgscct sasptvcflk erlqlkhlsl lttlsnrvcs
241  qyaaygekks rlsnliklaq kvptadledv lplaeditni lskccesase dcmakelpeh
301  tvklcdnlst knskfedccq ektamdvfvc tyfmpaaqlp elpdvelptn kdvcdpgntk
361  vmdkytfels rrthlpevfl skvleptlks lgeccdveds ttcfnakgpl lkkelssfid
421  kgqelcadys entfteykkk laerlkaklp datptelakl vnkhsdfasn ccsinspply
481  cdseidaelk nil
```

SEQ ID NO: 04 Human preproalbumin NCBI Ref: NP_000468
```
  1  mkwvtfisll flfssaysrg vfrrdahkse vahrfkdlge enfkalvlia faqylqqcpf
 61  edhvklvnev tefaktcvad esaencdksl htlfgdklct vatlretyge madccakqep
121  ernecflqhk ddnpnlprlv rpevdvmcta fhdneetflk kylyeiarrh pyfyapellf
181  fakrykaaft eccqaadkaa cllpkldelr degkassakq rlkcaslqkf gerafkawav
241  arlsqrfpka efaevsklvt dltkvhtecc hgdllecadd radlakyice nqdsissklk
301  eccekpllek shciaevend empadlpsla adfveskdvc knyaeakdvf lgmflyeyar
361  rhpdysvvll lrlaktyett lekccaaadp hecyakvfde fkplveepqn likqncelfe
421  qlgeykfqna llvrytkkvp qvstptievs rnlgkvgsk cckhpeakrm pcaedylsvv
481  lnqlcvlhek tpvsdrvtkc cteslvnrrp cfsalevdet yvpkefnaet ftfhadictl
541  sekerqikkq talvelvkhk pkatkeqlka vmddfaafve kcckaddket cfaeegkklv
601  aasqaalgl
```

SEQ ID NO: 05 Human proalbumin
```
     rg vfrrdahkse vahrfkdlge enfkalvlia faqylqqcpf
```

```
                       edhvklvnev tefaktcvad esaencdksl htlfgdklct vatlretyge madccakqep ernecflqhk ddnpnlprlv rpevdvmcta fhdneetflk kylyeiarrh pyfyapellf fakrykaaft eccqaadkaa cllpkldelr degkassakq rlkcaslqkf gerafkawav arlsqrfpka efaevsklvt dltkvhtecc hgdllecadd radlakyice nqdsissklk eccekpllek shciaevend empadlpsla adfveskdvc knyaeakdvf lgmflyeyar rhpdysvvll lrlaktyett lekccaaadp hecyakvfde fkplveepqn likqncelfe qlgeykfqna llvrytkkvp qvstptlvev srnlgkvgsk cckhpeakrm pcaedylsvv lnqlcvlhek tpvsdrvtkc cteslvnrrp cfsalevdet yvpkefnaet ftfhadictl sekerqikkq talvelvkhk pkatkeqlka vmddfaafve kcckaddket cfaeegkklv aasqaalgl SEQ ID NO: 06 Human albumin
                       dahkse vahrfkdlge enfkalvlia faqylqqcpf edhvklvnev tefaktcvad esaencdksl htlfgdklct vatlretyge madccakqep ernecflqhk ddnpnlprlv rpevdvmcta fhdneetflk kylyeiarrh pyfyapellf fakrykaaft eccqaadkaa cllpkldelr degkassakq rlkcaslqkf gerafkawav arlsqrfpka efaevsklvt dltkvhtecc hgdllecadd radlakyice nqdsissklk eccekpllek shciaevend empadlpsla adfveskdvc knyaeakdvf lgmflyeyar rhpdysvvll lrlaktyett lekccaaadp hecyakvfde fkplveepqn likqncelfe qlgeykfqna llvrytkkvp qvstptivev srnlgkvgsk cckhpeakrm pcaedylsvv lnqlcvlhek tpvsdrvtkc cteslvnrrp cfsalevdet yvpkefnaet ftfhadictl sekerqikkg talvelvkhk pkatkeqlka vmddfaafve kcckaddket cfaeegkklv aasqaalgl
```

What is claimed herein:

1. A method for determining a level of bioavailable vitamin D and a level of free vitamin D in a subject, the method comprising:

performing assays on a blood sample obtained from the subject to determine a level of VDBP (vitamin D binding protein) polypeptide, albumin polypeptide and total vitamin D;

calculating a level of bioavailable vitamin D, wherein a level of bioavailable vitamin D is:

=(Kalb*[Alb]+1)*[Free Vitamin D]

and calculating a level of free vitamin D, wherein a level of free vitamin D is:

={-{$K_{DBP}$·[Total DBP]-$K_{DBP}$·[Total Vitamin D]+$K_{alb}$·[Alb]+1}+√{($K_{DBP}$·[Total DBP]-$K_{DBP}$·[Total Vitamin D]+$K_{alb}$·[Alb]+1)$^2$+4·($K_{DBP}$·$K_{alb}$·[Alb]+$K_{DBP}$)·([Total Vitamin D])}}÷(2·{$K_{DBP}$·$K_{alb}$·[Alb]+$K_{DBP}$}).

2. The method of claim 1, wherein a level of bioavailable vitamin D lower than 25% of the mean value of bioavailable vitamin D in a population of healthy subjects indicates that the subject has a vitamin D insufficiency, and the method includes administering a vitamin D insufficiency treatment to a subject who is determined to have a vitamin D insufficiency.

3. The method of claim 1, wherein the vitamin D is selected from the group consisting of: 25-hydroxyvitamin D and 1,25-dihydroxyvitamin D.

4. The method of claim 1, wherein the assays to determine the level of VDBP polypeptide or albumin polypeptide comprises use of a method selected from the group consisting of:

enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy.

5. The method of claim 1, wherein the assays to determine the level of total vitamin D comprises the use of a method selected from the group consisting of:

radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

6. The method of claim 2, wherein an insufficiency of vitamin D indicates an increased risk of a condition selected from the group consisting of:

decreased bone density; decreased bone mineral density; bone fractures; bone resorption; rickets; osteitis fibrosa cystica; fibrogenesis imperfect ossium; osteoschlerosis; osteoporosis; osteomalacia; elevated parathyroid hormone levels; parathyroid gland hyperplasia; secondary hyperparathyroidism; hypocalcemia; infection; cancer; psoriasis; cardiovascular disease; renal osteodystrophy; renal disease; end-stage renal disease; chronic kidney disease; chronic kidney disease-associated mineral and bone disorder; extraskeletal calcification; obesity; allergy, asthma; multiple sclerosis; muscle weakness; rheumatoid arthritis and diabetes.

7. The method of claim 2, wherein the treatment comprises administering a compound selected from the group consisting of:

calcitriol; dihydrotachysterol; doxercalciferol; paricalcitol; cholecalciferol and ergocalciferol.

8. The method of claim 1, wherein level of bioavailable vitamin D and the level of free vitamin D are calculated by a processor.

* * * * *